(12) United States Patent
Leonard et al.

(10) Patent No.: US 8,062,878 B2
(45) Date of Patent: Nov. 22, 2011

(54) METHODS FOR MICROBIAL PRODUCTION OF TERPENOIDS

(75) Inventors: Effendi Leonard, Emeryville, CA (US); Parayil K. Ajikumar, Cambridge, MA (US); Kristala Lanett Jones Prather, Cambridge, MA (US); Gregory Stephanopoulos, Winchester, MA (US); Kelly Thayer, Worcester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/615,985

(22) Filed: Nov. 10, 2009

(65) Prior Publication Data

US 2011/0111457 A1 May 12, 2011

(51) Int. Cl.
*C12N 1/00* (2006.01)
*C12N 1/20* (2006.01)
*C12P 1/00* (2006.01)

(52) U.S. Cl. .................. 435/243; 435/252.3; 435/41
(58) Field of Classification Search .......... None
See application file for complete search history.

(56) References Cited

U.S. PATENT DOCUMENTS

2002/0164736 A1 11/2002 Matsuda et al.
2007/0009996 A1* 1/2007 Matsuda et al. ............. 435/117

OTHER PUBLICATIONS

Ajikumar et al., Terpenoids: opportunities for biosynthesis of natural product drugs using engineered microorganisms. Mol Pharm. Mar.-Apr. 2008;5(2):167-90. Epub Mar. 21, 2008.
Huang et al., Engineering *Escherichia coli* for the synthesis of taxadiene, a key intermediate in the biosynthesis of taxol. Bioorg Med Chem. Sep. 2001;9(9):2237-42.
Kirby et al., Biosynthesis of plant isoprenoids: perspectives for microbial engineering. Annu Rev Plant Biol. 2009;60:335-55.
Leonard et al., Combining metabolic and protein engineering of a terpenoid biosynthetic pathway for overproduction and selectivity control. Proc Natl Acad Sci U S A. Aug. 3, 2010;107(31):13654-9. Epub Jul. 19, 2010.
Reiling et al., Mono and diterpene production in *Escherichia coli*. Biotechnol Bioeng. Jul. 2004;87(2):200-12.
Wang et al., Directed evolution of metabolically engineered *Escherichia coli* for carotenoid production. Biotechnol Prog. Nov.-Dec. 2000;16(6):922-6.

* cited by examiner

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to recombinant expression of terpenoid synthase enzymes and geranylgeranyl diphosphate synthase (GGPPS) enzymes in cells and the production of diterpenoids.

15 Claims, 12 Drawing Sheets

```
POSITION  GbLPS  AbAS  PaAS  PaISO
   593      M     I     I     I
   618      C     N     N     I
   619      L     F     F     F
   620      A     T     T     T
   696      L     Q     Q     L
   700      Y     Y     Y     H
   723      K     S     S     S
   727      A     A     A     S
   729      A     G     G     G
   731      V     V     V     L
   769      N     N     N     N
   777      E     E     E     E
   838      N     E     E     E
   854      G     T     T     T
   855      I     L     L     L
```

| MUTATION | 1 | 2 | 3 | PRODUCTIVITY (FOLD) |
|---|---|---|---|---|
| M593I | 83 | 12 | 5 | 3.7 |
| C618N | 91 | 9 | TA | 0.2 |
| L619F | 94 | 6 | TA | 1.5 |
| A620T | 87 | 11 | 2 | 1.3 |
| L696Q | 86 | 7 | 7 | 1.6 |
| Y700H | 71 | TA | 29 | 0.4 |
| K723S | 90 | 7 | 3 | 1.8 |
| A727S | ND | ND | ND | 0.0 |
| A729G | ND | ND | 100 | 0.02 |
| V731L | 100 | ND | ND | 0.08 |
| N769A | ND | ND | ND | 0.0 |
| E777A | ND | ND | ND | 0.0 |
| N838E | 92 | 6 | 2 | 2.2 |
| G854T | 79 | 14 | 7 | 1.4 |
| I855L | 90 | 7 | 3 | 0.7 |

Fig. 2C

```
EAS    (1)  ------------------------------------------------
LPS    (1)  MAGVLFANLPCSLQLSPKVPFRQSTNILIPFHKRSSFGFNAQHCVRSHLR
EAS    (1)  ------------------------------------------------
LPS   (51)  LRWNCVGIHASAAETRPDQLPQEERFVSRLNADYHPAVWKDDFIDSLTSP
EAS    (1)  ------------------------------------------------
LPS  (101)  NSHATSKSSVDETINKRIQTLVKEIQCMFQSMGDGETNPSAYDTAWVARI
EAS    (1)  ------------------------------------------------
LPS  (151)  PSIDGSGAPQFPQTLQWILNNQLPDGSWGEECIFLAYDRVLNTLACLLTL
EAS    (1)  ------------------------------------------------
LPS  (201)  KIWNKGDIQVQKGVEFVRKHMEEMKDEADNHRPSGFEVVFPAMLDEAKSL
EAS    (1)  -----MASAAVANYEEEIVRPVADFSPSLWGDQFLSFSIDNQVAEKYIYA
LPS  (251)  GLDLPYHLPFISQIHQKRQKKLQKIPLNVLHNHQTALLYSLEGLQDVVDW
EAS   (46)  QEIEALKEQTRSMLLATG---------RK--------------------
LPS  (301)  QEITNLQSRDGSFLSSPASTACVFMHTQNKRCLHFLNFVLSKFGDYVPCH
EAS   (66)  ----LADTLNLIDIIERLGISYHFEKEIDEILDQIYN---------QN--
LPS  (351)  YPLDLFERLWAVDTVERLGIDRYFKKEIKESLDYVYRYWDAERGVGWARC
EAS  (101)  SNCNDLCTSALQFRLLRQHGFNISPEIFSKFQDENG--K-FKESLASDVL
LPS  (401)  NPIPDVDDTAMGLRILRLHGYNVSSDVLENFRDEKGDFFCFAGQTQIGVT
EAS  (148)  GLLNLYEASHVRTHADDILEDALAFSTIHLESAAPH--------LKSPLR
LPS  (451)  DNLNLYRCSQVCFPGEKIMEEAKTFTTNHLQNALAKNNAFDKWAVKKDLP
EAS  (190)  EQVTHALEQCLHKGVPRVETRFFISSIYDKEQSK-----------NNVLL
LPS  (501)  GEVEYAIKYPWHRSMPRLEARSYIEQFGSNDVWLGKTVYKMLYVSNEKYL
EAS  (229)  RFAKLDFNLLQMLHQELAQVSRWWKDLDFVTTLPYARDRVVECYFWALG
LPS  (551)  ELAKLDFNMVQALHQKETQHIVSWWRESGFN-DLTFTRQRPVEMYFSVAV
EAS  (279)  VYFEPQYSQARVMLVKTISMISIVDDTFDAYGTVKELEAYTDAIQRWDIN
LPS  (600)  SMFEPEFAACRIAYAKTSCLAVILDDLYDTHGSLDDLKLFSEAVRRWDIS
EAS  (329)  EIDRLPD-YMKISYKAILDLYKDYEKELSSAGRSHIVCHAIERMKEVVRN
LPS  (650)  VLDSVRDNQLKVCFLGLYNTVNGFGKDGLKEQGRDVLGYLRKVWEGLLAS
EAS  (378)  YNVESTWFIEGYMPPVSEYLSNALATTTYYYLATTSYLG-MKSATEQDFE
LPS  (700)  YTKEAEWSAAKYVPTFNEYVENAKVSIALATVVLNSIFFTGELLPDYILQ
EAS  (427)  WLSKNPKILEASVIICRVIDDTATYEVEKSRGQIATGIECCMRDYG-IST
LPS  (750)  QVDLRSKFLHLVSLTGRLINDTKTYQAERNRGELVSSVQCYMRENPECTE
EAS  (476)  KEAMAKFQNMAETAWKDINEGLLRPTVSTEFLTPILNLARIVEVTYIHN
LPS  (800)  EEALSHVYGIIDNALKELNWELANPASNAPLCVRRLLFNTARVMQLFYMY
EAS  (526)  LDGYTHPEKVLKPHIINLLVDSIKI
LPS  (850)  RDGFGISDKEMKDHVSRTLFDPVA-
```

Fig. 7

SEQUENCE LISTING

```
<160> NUMBER OF SEQ ID NOS: 147

<210> SEQ ID NO 1
<211> LENGTH: 2705
<212> TYPE: DNA
<213> ORGANISM: Ginkgo biloba
<220> FEATURE:
<221> NAME/KEY: CDS
<222> LOCATION: (23)..(2644)
```

```
<400> SEQUENCE: 1
atatttgcct aaacctgcac aa atg gct ggg gtg ctc ttt gca aat ctg cct        52
                        Met Ala Gly Val Leu Phe Ala Asn Leu Pro
                         1               5                  10 tgc tca ctg caa ctc tct cca aaa gtt ccc ttc cgg caa tcc act aat        100
Cys Ser Leu Gln Leu Ser Pro Lys Val Pro Phe Arg Gln Ser Thr Asn
             15                  20                  25 att ctt att cct ttt cac aag aga tcc tca ttt gga ttt aat gca cag        148
Ile Leu Ile Pro Phe His Lys Arg Ser Ser Phe Gly Phe Asn Ala Gln
         30                  35                  40 cac tgc gtc cgt tct cac tta agg ctg aga tgg aat tgt gtc ggg att        196
His Cys Val Arg Ser His Leu Arg Leu Arg Trp Asn Cys Val Gly Ile
             45                  50                  55 cat gcc tca gct gca gag act cgt cca gat cag ctt cca cag gag gaa        244
His Ala Ser Ala Ala Glu Thr Arg Pro Asp Gln Leu Pro Gln Glu Glu
     60                  65                  70 cgc ttt gtg tcg aga ctt aat gcg gat tat cat cca gct gtc tgg aag        292
Arg Phe Val Ser Arg Leu Asn Ala Asp Tyr His Pro Ala Val Trp Lys
75                   80                  85                  90 gac gat ttc atc gac tct cta aca tcc cct aat tcc cac gcg aca tcg        340
Asp Asp Phe Ile Asp Ser Leu Thr Ser Pro Asn Ser His Ala Thr Ser
                 95                 100                 105 aaa tca agc gtc gat gag aca atc aat aaa aga atc cag aca ttg gtg        388
Lys Ser Ser Val Asp Glu Thr Ile Asn Lys Arg Ile Gln Thr Leu Val
            110                 115                 120 aag gaa atc cag tgc atg ttt cag tcc atg ggc gac ggt gaa acg aat        436
Lys Glu Ile Gln Cys Met Phe Gln Ser Met Gly Asp Gly Glu Thr Asn
        125                 130                 135 cca tct gca tat gat aca gct tgg gtg gca aga att ccg tca att gac        484
Pro Ser Ala Tyr Asp Thr Ala Trp Val Ala Arg Ile Pro Ser Ile Asp
    140                 145                 150 ggc tct ggt gca ccc caa ttt ccc caa acg ctt caa tgg att ctg aac        532
Gly Ser Gly Ala Pro Gln Phe Pro Gln Thr Leu Gln Trp Ile Leu Asn
155                 160                 165                 170 aat caa ctg cca gat ggc tcg tgg ggt gag gag tgc att ttt ctg gcg        580
Asn Gln Leu Pro Asp Gly Ser Trp Gly Glu Glu Cys Ile Phe Leu Ala
                175                 180                 185 tat gac aga gtt tta aac act ctc gcc tgc ctc ctc act ctc aaa ata        628
Tyr Asp Arg Val Leu Asn Thr Leu Ala Cys Leu Leu Thr Leu Lys Ile
            190                 195                 200 tgg aat aag ggc gac att caa gtg cag aaa ggg gtt gag ttt gtg aga        676
Trp Asn Lys Gly Asp Ile Gln Val Gln Lys Gly Val Glu Phe Val Arg
        205                 210                 215 aaa cac atg gaa gaa atg aag gac gaa gct gac aat cac agg cca agt        724
Lys His Met Glu Glu Met Lys Asp Glu Ala Asp Asn His Arg Pro Ser
    220                 225                 230 gga ttc gag gtc gtg ttt cct gca atg tta gat gaa gca aaa agc ttg        772
Gly Phe Glu Val Val Phe Pro Ala Met Leu Asp Glu Ala Lys Ser Leu
235                 240                 245                 250 gga ttg gat ctt cct tat cac ctc cct ttc atc tcc caa atc cac caa        820
Gly Leu Asp Leu Pro Tyr His Leu Pro Phe Ile Ser Gln Ile His Gln
                255                 260                 265 aag cgc cag aaa aag ctt caa aag att ccc ctc aat gtt ctt cat aac        868
Lys Arg Gln Lys Lys Leu Gln Lys Ile Pro Leu Asn Val Leu His Asn
            270                 275                 280 cat cag acg gcg ttg ctc tac tct ctg gag ggt ttg caa gat gtg gtg        916
His Gln Thr Ala Leu Leu Tyr Ser Leu Glu Gly Leu Gln Asp Val Val
        285                 290                 295 gac tgg caa gag atc aca aat ctt caa tca aga gac gga tca ttt tta        964
Asp Trp Gln Glu Ile Thr Asn Leu Gln Ser Arg Asp Gly Ser Phe Leu
```

```
Asp Trp Gln Glu Ile Thr Asn Leu Gln Ser Arg Asp Gly Ser Phe Leu
    300                 305                 310 agc tcc cct gca tct act gct tgt gtc ttc atg cac act caa aac aaa         1012
Ser Ser Pro Ala Ser Thr Ala Cys Val Phe Met His Thr Gln Asn Lys
315                 320                 325                 330 cga tgc ctc cac ttt ctc aac ttc gtg ctc agc aaa ttt ggc gac tac         1060
Arg Cys Leu His Phe Leu Asn Phe Val Leu Ser Lys Phe Gly Asp Tyr
                335                 340                 345 gtt cct tgc cat tac cca ctt gat cta ttt gaa cgc ctc tgg gct gtc         1108
Val Pro Cys His Tyr Pro Leu Asp Leu Phe Glu Arg Leu Trp Ala Val
            350                 355                 360 gat aca gtt gaa cgc ttg gga atc gat cgc tat ttc aag aaa gaa atc         1156
Asp Thr Val Glu Arg Leu Gly Ile Asp Arg Tyr Phe Lys Lys Glu Ile
        365                 370                 375 aaa gaa tct ctg gat tac gtt tat agg tac tgg gac gcc gaa aga ggc         1204
Lys Glu Ser Leu Asp Tyr Val Tyr Arg Tyr Trp Asp Ala Glu Arg Gly
    380                 385                 390 gtg gga tgg gca aga tgc aat cct att cct gat gtc gat gac act gcc         1252
Val Gly Trp Ala Arg Cys Asn Pro Ile Pro Asp Val Asp Asp Thr Ala
395                 400                 405                 410 atg ggt ctt aga atc ctg aga ctt cat gga tac aat gta tct tca gat         1300
Met Gly Leu Arg Ile Leu Arg Leu His Gly Tyr Asn Val Ser Ser Asp
                415                 420                 425 gtt ctg gag aat ttc aga gac gag aaa gga gac ttc ttt tgc ttt gcc         1348
Val Leu Glu Asn Phe Arg Asp Glu Lys Gly Asp Phe Phe Cys Phe Ala
            430                 435                 440 ggt caa acg caa att ggt gtg acc gat aat ctt aac ctt tat aga tgt         1396
Gly Gln Thr Gln Ile Gly Val Thr Asp Asn Leu Asn Leu Tyr Arg Cys
        445                 450                 455 tca caa gta tgt ttt ccg gga gaa aag ata atg gaa gaa gct aag acc         1444
Ser Gln Val Cys Phe Pro Gly Glu Lys Ile Met Glu Glu Ala Lys Thr
    460                 465                 470 ttc act aca aat cat ctc caa aat gct ctt gcc aaa aac aac gca ttt         1492
Phe Thr Thr Asn His Leu Gln Asn Ala Leu Ala Lys Asn Asn Ala Phe
475                 480                 485                 490 gat aag tgg gct gtc aag aag gat ctt cct gga gag gtg gag tat gct         1540
Asp Lys Trp Ala Val Lys Lys Asp Leu Pro Gly Glu Val Glu Tyr Ala
                495                 500                 505 ata aag tat ccg tgg cat aga agt atg cca aga ttg gag gca aga agt         1588
Ile Lys Tyr Pro Trp His Arg Ser Met Pro Arg Leu Glu Ala Arg Ser
            510                 515                 520 tac ata gag caa ttt gga tca aat gat gtc tgg ctg ggg aag act gtg         1636
Tyr Ile Glu Gln Phe Gly Ser Asn Asp Val Trp Leu Gly Lys Thr Val
        525                 530                 535 tat aag atg cta tat gtg agc aac gaa aaa tat ttg gag ctg gcc aaa         1684
Tyr Lys Met Leu Tyr Val Ser Asn Glu Lys Tyr Leu Glu Leu Ala Lys
    540                 545                 550 ttg gac ttc aat atg gtg cag gcc tta cac caa aag gag act caa cac         1732
Leu Asp Phe Asn Met Val Gln Ala Leu His Gln Lys Glu Thr Gln His
555                 560                 565                 570 att gtc agc tgg tgg aga gaa tcg gga ttc aat gat ctt aca ttc acc         1780
Ile Val Ser Trp Trp Arg Glu Ser Gly Phe Asn Asp Leu Thr Phe Thr
                575                 580                 585 cgc cag cgg cct gtg gaa atg tat ttc tca gtg gcg gtt agt atg ttt         1828
Arg Gln Arg Pro Val Glu Met Tyr Phe Ser Val Ala Val Ser Met Phe
            590                 595                 600 gag cca gaa ttc gct gct tgt aga att gcc tat gcc aag act tct tgc         1876
Glu Pro Glu Phe Ala Ala Cys Arg Ile Ala Tyr Ala Lys Thr Ser Cys
        605                 610                 615 ctc gca gtt att cta gac gat ctt tac gac acc cac gga tct ctg gat         1924
```

| | | | | | | | | | | | | | | | | |
|---|---|---|---|---|---|---|---|---|---|---|---|---|---|---|---|---|
| Leu | Ala | Val | Ile | Leu | Asp | Asp | Leu | Tyr | Asp | Thr | His | Gly | Ser | Leu | Asp | |
| | 620 | | | | 625 | | | | | 630 | | | | | | |

```
gat   ctt   aaa   ttg   ttc   tct   gaa   gcg   gtc   cga   aga   tgg   gat   atc   tct   gtg      1972
Asp   Leu   Lys   Leu   Phe   Ser   Glu   Ala   Val   Arg   Arg   Trp   Asp   Ile   Ser   Val
635                           640                           645                           650 ctg   gat   agc   gtt   cgg   gat   aat   cag   ttg   aaa   gtt   tgc   ttc   cta   ggg   ctg      2020
Leu   Asp   Ser   Val   Arg   Asp   Asn   Gln   Leu   Lys   Val   Cys   Phe   Leu   Gly   Leu
                          655                           660                           665 tac   aac   aca   gtg   aat   gga   ttt   gga   aaa   gat   gga   ctc   aag   gaa   caa   ggc      2068
Tyr   Asn   Thr   Val   Asn   Gly   Phe   Gly   Lys   Asp   Gly   Leu   Lys   Glu   Gln   Gly
                          670                           675                           680 cgt   gat   gtg   ctg   ggc   tat   ctt   cga   aaa   gta   tgg   gag   ggc   ttg   ctc   gca      2116
Arg   Asp   Val   Leu   Gly   Tyr   Leu   Arg   Lys   Val   Trp   Glu   Gly   Leu   Leu   Ala
                   685                           690                           695 tcg   tat   acc   aaa   gaa   gcc   gaa   tgg   tcg   gca   gca   aag   tat   gtg   ccg   aca      2164
Ser   Tyr   Thr   Lys   Glu   Ala   Glu   Trp   Ser   Ala   Ala   Lys   Tyr   Val   Pro   Thr
700                           705                           710 ttc   aac   gaa   tat   gtg   gaa   aat   gcc   aaa   gtg   tcc   ata   gca   ctt   gcg   aca      2212
Phe   Asn   Glu   Tyr   Val   Glu   Asn   Ala   Lys   Val   Ser   Ile   Ala   Leu   Ala   Thr
715                           720                           725                           730 gtc   gta   cta   aac   tca   atc   ttt   ttc   act   gga   gaa   tta   ctt   cct   gat   tac      2260
Val   Val   Leu   Asn   Ser   Ile   Phe   Phe   Thr   Gly   Glu   Leu   Leu   Pro   Asp   Tyr
                          735                           740                           745 att   tta   cag   caa   gta   gac   ctt   cgg   tcc   aaa   ttt   ctg   cat   ctt   gtg   tct      2308
Ile   Leu   Gln   Gln   Val   Asp   Leu   Arg   Ser   Lys   Phe   Leu   His   Leu   Val   Ser
                          750                           755                           760 ttg   act   gga   cga   cta   atc   aat   gac   acc   aag   act   tac   cag   gcc   gag   aga      2356
Leu   Thr   Gly   Arg   Leu   Ile   Asn   Asp   Thr   Lys   Thr   Tyr   Gln   Ala   Glu   Arg
                   765                           770                           775 aac   cgt   ggt   gaa   ttg   gtt   tcc   agc   gta   cag   tgc   tac   atg   agg   gaa   aat      2404
Asn   Arg   Gly   Glu   Leu   Val   Ser   Ser   Val   Gln   Cys   Tyr   Met   Arg   Glu   Asn
780                           785                           790 ccg   gag   tgc   aca   gag   gaa   gaa   gct   cta   agt   cat   gtt   tat   ggt   atc   atc      2452
Pro   Glu   Cys   Thr   Glu   Glu   Glu   Ala   Leu   Ser   His   Val   Tyr   Gly   Ile   Ile
795                           800                           805                           810 gac   aac   gca   ctg   aag   gaa   ttg   aat   tgg   gag   ttg   gcc   aac   cca   gcg   agc      2500
Asp   Asn   Ala   Leu   Lys   Glu   Leu   Asn   Trp   Glu   Leu   Ala   Asn   Pro   Ala   Ser
                          815                           820                           825 aat   gcc   cca   ttg   tgt   gtg   aga   aga   ctg   ctg   ttc   aac   act   gca   aga   gtg      2548
Asn   Ala   Pro   Leu   Cys   Val   Arg   Arg   Leu   Leu   Phe   Asn   Thr   Ala   Arg   Val
                   830                           835                           840 atg   cag   ctg   ttt   tat   atg   tac   aga   gat   ggc   ttt   ggt   atc   tct   gac   aaa      2596
Met   Gln   Leu   Phe   Tyr   Met   Tyr   Arg   Asp   Gly   Phe   Gly   Ile   Ser   Asp   Lys
                   845                           850                           855 gag   atg   aaa   gac   cat   gtc   agc   cga   act   ctt   ttc   gat   cct   gtg   gcg   tag      2644
Glu   Met   Lys   Asp   His   Val   Ser   Arg   Thr   Leu   Phe   Asp   Pro   Val   Ala
860                           865                           870 catactgata ttatatataa tattcatatt caatccaaaa aaaaaaaaaa aaaaaaaaa                                    2704 a                                                                                                  2705

<210> SEQ ID NO 2
<211> LENGTH: 873
<212> TYPE: PRT
<213> ORGANISM: Ginkgo biloba

<400> SEQUENCE: 2

Met Ala Gly Val Leu Phe Ala Asn Leu Pro Cys Ser Leu Gln Leu Ser
1               5                   10                  15

Pro Lys Val Pro Phe Arg Gln Ser Thr Asn Ile Leu Ile Pro Phe His
            20                  25                  30
```

```
Lys Arg Ser Ser Phe Gly Phe Asn Ala Gln His Cys Val Arg Ser His
             35                  40                  45

Leu Arg Leu Arg Trp Asn Cys Val Gly Ile His Ala Ser Ala Ala Glu
 50                  55                  60

Thr Arg Pro Asp Gln Leu Pro Gln Glu Glu Arg Phe Val Ser Arg Leu
 65                  70                  75                  80

Asn Ala Asp Tyr His Pro Ala Val Trp Lys Asp Asp Phe Ile Asp Ser
             85                  90                  95

Leu Thr Ser Pro Asn Ser His Ala Thr Ser Lys Ser Ser Val Asp Glu
            100                 105                 110

Thr Ile Asn Lys Arg Ile Gln Thr Leu Val Lys Glu Ile Gln Cys Met
            115                 120                 125

Phe Gln Ser Met Gly Asp Gly Glu Thr Asn Pro Ser Ala Tyr Asp Thr
            130                 135                 140

Ala Trp Val Ala Arg Ile Pro Ser Ile Asp Gly Ser Gly Ala Pro Gln
145                 150                 155                 160

Phe Pro Gln Thr Leu Gln Trp Ile Leu Asn Asn Gln Leu Pro Asp Gly
            165                 170                 175

Ser Trp Gly Glu Glu Cys Ile Phe Leu Ala Tyr Asp Arg Val Leu Asn
            180                 185                 190

Thr Leu Ala Cys Leu Leu Thr Leu Lys Ile Trp Asn Lys Gly Asp Ile
            195                 200                 205

Gln Val Gln Lys Gly Val Glu Phe Val Arg Lys His Met Glu Glu Met
            210                 215                 220

Lys Asp Glu Ala Asp Asn His Arg Pro Ser Gly Phe Glu Val Val Phe
225                 230                 235                 240

Pro Ala Met Leu Asp Glu Ala Lys Ser Leu Gly Leu Asp Leu Pro Tyr
            245                 250                 255

His Leu Pro Phe Ile Ser Gln Ile His Gln Lys Arg Gln Lys Lys Leu
            260                 265                 270

Gln Lys Ile Pro Leu Asn Val Leu His Asn His Gln Thr Ala Leu Leu
            275                 280                 285

Tyr Ser Leu Glu Gly Leu Gln Asp Val Val Asp Trp Gln Glu Ile Thr
            290                 295                 300

Asn Leu Gln Ser Arg Asp Gly Ser Phe Leu Ser Ser Pro Ala Ser Thr
305                 310                 315                 320

Ala Cys Val Phe Met His Thr Gln Asn Lys Arg Cys Leu His Phe Leu
            325                 330                 335

Asn Phe Val Leu Ser Lys Phe Gly Asp Tyr Val Pro Cys His Tyr Pro
            340                 345                 350

Leu Asp Leu Phe Glu Arg Leu Trp Ala Val Asp Thr Val Glu Arg Leu
            355                 360                 365

Gly Ile Asp Arg Tyr Phe Lys Lys Glu Ile Lys Glu Ser Leu Asp Tyr
            370                 375                 380

Val Tyr Arg Tyr Trp Asp Ala Glu Arg Gly Val Gly Trp Ala Arg Cys
385                 390                 395                 400

Asn Pro Ile Pro Asp Val Asp Thr Ala Met Gly Leu Arg Ile Leu
            405                 410                 415

Arg Leu His Gly Tyr Asn Val Ser Asp Val Leu Glu Asn Phe Arg
            420                 425                 430

Asp Glu Lys Gly Asp Phe Phe Cys Phe Ala Gly Gln Thr Gln Ile Gly
            435                 440                 445

Val Thr Asp Asn Leu Asn Leu Tyr Arg Cys Ser Gln Val Cys Phe Pro
```

```
                450             455             460
Gly Glu Lys Ile Met Glu Ala Lys Thr Phe Thr Thr Asn His Leu
465                 470                 475                 480

Gln Asn Ala Leu Ala Lys Asn Ala Phe Asp Lys Trp Ala Val Lys
                485                 490                 495

Lys Asp Leu Pro Gly Glu Val Glu Tyr Ala Ile Lys Tyr Pro Trp His
                500                 505                 510

Arg Ser Met Pro Arg Leu Glu Ala Arg Ser Tyr Ile Glu Gln Phe Gly
            515                 520                 525

Ser Asn Asp Val Trp Leu Gly Lys Thr Val Tyr Lys Met Leu Tyr Val
530                 535                 540

Ser Asn Glu Lys Tyr Leu Glu Leu Ala Lys Leu Asp Phe Asn Met Val
545                 550                 555                 560

Gln Ala Leu His Gln Lys Glu Thr Gln His Ile Val Ser Trp Trp Arg
                565                 570                 575

Glu Ser Gly Phe Asn Asp Leu Thr Phe Thr Arg Gln Arg Pro Val Glu
            580                 585                 590

Met Tyr Phe Ser Val Ala Val Ser Met Phe Glu Pro Glu Phe Ala Ala
        595                 600                 605

Cys Arg Ile Ala Tyr Ala Lys Thr Ser Cys Leu Ala Val Ile Leu Asp
610                 615                 620

Asp Leu Tyr Asp Thr His Gly Ser Leu Asp Leu Lys Leu Phe Ser
625                 630                 635                 640

Glu Ala Val Arg Arg Trp Asp Ile Ser Val Leu Asp Ser Val Arg Asp
                645                 650                 655

Asn Gln Leu Lys Val Cys Phe Leu Gly Leu Tyr Asn Thr Val Asn Gly
            660                 665                 670

Phe Gly Lys Asp Gly Leu Lys Glu Gln Gly Arg Asp Val Leu Gly Tyr
        675                 680                 685

Leu Arg Lys Val Trp Glu Gly Leu Leu Ala Ser Tyr Thr Lys Glu Ala
690                 695                 700

Glu Trp Ser Ala Ala Lys Tyr Val Pro Thr Phe Asn Glu Tyr Val Glu
705                 710                 715                 720

Asn Ala Lys Val Ser Ile Ala Leu Ala Thr Val Val Leu Asn Ser Ile
                725                 730                 735

Phe Phe Thr Gly Glu Leu Leu Pro Asp Tyr Ile Leu Gln Gln Val Asp
            740                 745                 750

Leu Arg Ser Lys Phe Leu His Leu Val Ser Leu Thr Gly Arg Leu Ile
        755                 760                 765

Asn Asp Thr Lys Thr Tyr Gln Ala Glu Arg Asn Arg Gly Glu Leu Val
770                 775                 780

Ser Ser Val Gln Cys Tyr Met Arg Glu Asn Pro Glu Cys Thr Glu Glu
785                 790                 795                 800

Glu Ala Leu Ser His Val Tyr Gly Ile Ile Asp Asn Ala Leu Lys Glu
                805                 810                 815

Leu Asn Trp Glu Leu Ala Asn Pro Ala Ser Asn Ala Pro Leu Cys Val
            820                 825                 830

Arg Arg Leu Leu Phe Asn Thr Ala Arg Val Met Gln Leu Phe Tyr Met
        835                 840                 845

Tyr Arg Asp Gly Phe Gly Ile Ser Asp Lys Glu Met Lys Asp His Val
850                 855                 860

Ser Arg Thr Leu Phe Asp Pro Val Ala
865                 870
```

<210> SEQ ID NO 3
<211> LENGTH: 1889
<212> TYPE: DNA
<213> ORGANISM: Taxus canadensis
<220> FEATURE:
<221> NAME/KEY: CDS
<222> LOCATION: (308)..(1489)

<400> SEQUENCE: 3

| | |
|---|---:|
| ggaagagcgg caatcattct gtcatttaaa ggttttctgc accgaaatcc tttaatttta | 60 |
| aggttttctg gaaggtgtgt gtgaaaattt gaagaaaatt aacaagactg taagtgtttt | 120 |
| tatatattta tgagctttgg tttacttggg tgttactgaa ttggaacata cgtgcatgtc | 180 |
| ggagcaaagc agcatatttg aaatttgtgg gtgttctttg aggtgtgttg cggatataga | 240 |
| tttgattgtt cagagttagt gtattttttt ttttgttgg ttagattaat tgggcaagtt | 300 |

| | | | | | | | | | | | | | | | |
|---|---|---|---|---|---|---|---|---|---|---|---|---|---|---|---:|
| atagaga | atg | gct | tac | acg | gca | atg | gca | gca | ggg | acc | caa | agc | ttg | caa | 349 |
| | Met | Ala | Tyr | Thr | Ala | Met | Ala | Ala | Gly | Thr | Gln | Ser | Leu | Gln | |
| | 1 | | | 5 | | | | | 10 | | | | | | |
| ctc | cgc | act | gtt | gct | tcc | tat | caa | gaa | tgc | aat | agt | atg | agg | agt | tgt | 397 |
| Leu | Arg | Thr | Val | Ala | Ser | Tyr | Gln | Glu | Cys | Asn | Ser | Met | Arg | Ser | Cys |
| 15 | | | | 20 | | | | | 25 | | | | | 30 | |
| ttt | aaa | ttg | aca | cct | ttt | aaa | agt | ttt | cat | gga | gtg | aat | ttc | aat | gtt | 445 |
| Phe | Lys | Leu | Thr | Pro | Phe | Lys | Ser | Phe | His | Gly | Val | Asn | Phe | Asn | Val |
| | | | 35 | | | | | 40 | | | | | 45 | | |
| ccc | tca | ctg | ggt | gct | gct | aat | tgt | gag | att | atg | ggt | cac | ctg | aaa | ctt | 493 |
| Pro | Ser | Leu | Gly | Ala | Ala | Asn | Cys | Glu | Ile | Met | Gly | His | Leu | Lys | Leu |
| | | 50 | | | | | 55 | | | | | 60 | | | |
| ggg | tca | ttg | cca | tat | aaa | caa | tgt | tcg | gtg | tca | tct | aaa | tcc | aca | aaa | 541 |
| Gly | Ser | Leu | Pro | Tyr | Lys | Gln | Cys | Ser | Val | Ser | Ser | Lys | Ser | Thr | Lys |
| | 65 | | | | | 70 | | | | | 75 | | | | |
| aca | atg | gcc | cag | ttg | gtt | gat | ttg | gct | gaa | aca | gag | aag | gcg | gag | gga | 589 |
| Thr | Met | Ala | Gln | Leu | Val | Asp | Leu | Ala | Glu | Thr | Glu | Lys | Ala | Glu | Gly |
| 80 | | | | | 85 | | | | | 90 | | | | | |
| aag | gat | att | gaa | ttt | gat | ttc | aac | gag | tat | atg | aag | tcc | aag | gct | gtg | 637 |
| Lys | Asp | Ile | Glu | Phe | Asp | Phe | Asn | Glu | Tyr | Met | Lys | Ser | Lys | Ala | Val |
| 95 | | | | 100 | | | | | 105 | | | | | 110 | |
| gca | gtg | gat | gcg | gca | ctg | gat | aag | gca | atc | cca | ctt | gaa | tat | cct | gaa | 685 |
| Ala | Val | Asp | Ala | Ala | Leu | Asp | Lys | Ala | Ile | Pro | Leu | Glu | Tyr | Pro | Glu |
| | | | 115 | | | | | 120 | | | | | 125 | | |
| aaa | ata | cat | gaa | tca | atg | agg | tat | tca | ctt | cta | gca | gga | ggt | aag | cgc | 733 |
| Lys | Ile | His | Glu | Ser | Met | Arg | Tyr | Ser | Leu | Leu | Ala | Gly | Gly | Lys | Arg |
| | | 130 | | | | | 135 | | | | | 140 | | | |
| gtc | agg | cct | gct | ctg | tgc | att | gca | gca | tgt | gag | ctt | gta | gga | ggg | agt | 781 |
| Val | Arg | Pro | Ala | Leu | Cys | Ile | Ala | Ala | Cys | Glu | Leu | Val | Gly | Gly | Ser |
| | 145 | | | | | 150 | | | | | 155 | | | | |
| cag | gac | ctt | gcc | atg | cca | act | gcc | tgt | gca | atg | gag | atg | att | cat | acc | 829 |
| Gln | Asp | Leu | Ala | Met | Pro | Thr | Ala | Cys | Ala | Met | Glu | Met | Ile | His | Thr |
| 160 | | | | | 165 | | | | | 170 | | | | | |
| atg | tct | ctg | att | cat | gat | gac | ttg | ccg | tgc | atg | gat | aat | gat | gat | ttc | 877 |
| Met | Ser | Leu | Ile | His | Asp | Asp | Leu | Pro | Cys | Met | Asp | Asn | Asp | Asp | Phe |
| 175 | | | | 180 | | | | | 185 | | | | | 190 | |
| aga | aga | ggg | aag | cca | aca | aat | cac | aag | gtc | ttt | gga | gag | gac | act | gct | 925 |
| Arg | Arg | Gly | Lys | Pro | Thr | Asn | His | Lys | Val | Phe | Gly | Glu | Asp | Thr | Ala |
| | | | 195 | | | | | 200 | | | | | 205 | | |
| gtt | ctt | gca | ggg | gac | gcc | ctg | ctt | tca | ttt | gca | ttt | gag | cat | att | gct | 973 |
| Val | Leu | Ala | Gly | Asp | Ala | Leu | Leu | Ser | Phe | Ala | Phe | Glu | His | Ile | Ala |
| | | 210 | | | | | 215 | | | | | 220 | | | |
| gtg | gct | aca | agc | aag | act | gtg | cct | agt | gat | agg | act | tta | agg | gtg | ata | 1021 |
| Val | Ala | Thr | Ser | Lys | Thr | Val | Pro | Ser | Asp | Arg | Thr | Leu | Arg | Val | Ile |
| | 225 | | | | | 230 | | | | | 235 | | | | |

```
tct gaa ttg ggt aag aca ata ggc tct caa ggg ctt gta ggg ggg cag    1069
Ser Glu Leu Gly Lys Thr Ile Gly Ser Gln Gly Leu Val Gly Gly Gln
    240             245                 250 gtg gtt gat att aca tcc gag ggg gat gct aat gtg gac ctg aaa acc    1117
Val Val Asp Ile Thr Ser Glu Gly Asp Ala Asn Val Asp Leu Lys Thr
255                 260                 265                 270 ctg gaa tgg att cat ata cac aag act gct gtg ctc ttg gaa tgt tca    1165
Leu Glu Trp Ile His Ile His Lys Thr Ala Val Leu Leu Glu Cys Ser
                275                 280                 285 gtt gtg agt gga ggg atc ctt ggt ggt gct aca gag gac gag att gcg    1213
Val Val Ser Gly Gly Ile Leu Gly Gly Ala Thr Glu Asp Glu Ile Ala
            290                 295                 300 aga att cgg cgg tac gcc cgg tgt gtg ggg ctt ctg ttt cag gtt gtg    1261
Arg Ile Arg Arg Tyr Ala Arg Cys Val Gly Leu Leu Phe Gln Val Val
305                 310                 315 gat gac ata ctt gat gtc act aaa tct tct gaa gaa ttg gga aag act    1309
Asp Asp Ile Leu Asp Val Thr Lys Ser Ser Glu Glu Leu Gly Lys Thr
        320                 325                 330 gca gga aag gat ttg ctt act gat aag gct act tat ccc aag ttg atg    1357
Ala Gly Lys Asp Leu Leu Thr Asp Lys Ala Thr Tyr Pro Lys Leu Met
335                 340                 345                 350 ggc ctg gag aaa gca aaa gaa ttt gcc gct gaa ttg gcg acg aga gcc    1405
Gly Leu Glu Lys Ala Lys Glu Phe Ala Ala Glu Leu Ala Thr Arg Ala
                355                 360                 365 aag gaa gag ctg tca tcc ttt gat cag ata aag gct gca cct ttg ttg    1453
Lys Glu Glu Leu Ser Ser Phe Asp Gln Ile Lys Ala Ala Pro Leu Leu
            370                 375                 380 ggt ctt gca gat tac att gca ttc agg caa aac tga gaacaaagct         1499
Gly Leu Ala Asp Tyr Ile Ala Phe Arg Gln Asn
        385                 390 gtaaagctat tcttacatat catctgtttt tttttgacat ctgctgaaaa ttagcaaata  1559
acttttcaa gtttgtatct cccctgaatc ataacgattc aggacatgag gtttctggta   1619
ccattgaaaa gggggcgctc attgtagttg ttttttagct aattccaacc tgttttctat  1679
gtttccactt tggatcaatt tgatgtgat tatgtttgta ggggtgacat tgttagactt   1739
gttacatgtc atcaaattgt ttttgcggc cttaacatgg ttttaacttt tcactagcaa   1799
taaggtggcc taaagtgttt atgtaatttt tcaatataga tagatatctt ttaacaaaaa  1859
aaaaaaaaaa aaaaaaaaaa aaaaaaaaaa                                   1889

<210> SEQ ID NO 4
<211> LENGTH: 393
<212> TYPE: PRT
<213> ORGANISM: Taxus canadensis

<400> SEQUENCE: 4

Met Ala Tyr Thr Ala Met Ala Ala Gly Thr Gln Ser Leu Gln Leu Arg
1               5                   10                  15

Thr Val Ala Ser Tyr Gln Glu Cys Asn Ser Met Arg Ser Cys Phe Lys
                20                  25                  30

Leu Thr Pro Phe Lys Ser Phe His Gly Val Asn Phe Asn Val Pro Ser
            35                  40                  45

Leu Gly Ala Ala Asn Cys Glu Ile Met Gly His Leu Lys Leu Gly Ser
        50                  55                  60

Leu Pro Tyr Lys Gln Cys Ser Val Ser Lys Ser Thr Lys Thr Met
65                  70                  75                  80

Ala Gln Leu Val Asp Leu Ala Glu Thr Glu Lys Ala Glu Gly Lys Asp
                85                  90                  95
```

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 5
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 5
cgtacgcaaa aacctctaac ctggccgtaa tcctgg                                  36

<210> SEQ ID NO 6
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 6

```
ccaggattac ggccaggtta gaggtttttg cgtacg                              36
```

<210> SEQ ID NO 7
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 7

```
gcaaaaacct cttgcttcgc cgtaatcctg gacgatc                             37
```

<210> SEQ ID NO 8
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 8

```
gatcgtccag gattacggcg aagcaagagg ttttgc                              37
```

<210> SEQ ID NO 9
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 9

```
gtaaagtttg ggagggccag ctggcctcct atac                                34
```

<210> SEQ ID NO 10
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 10

```
gtataggagg ccagctggcc ctcccaaact ttac                                34
```

<210> SEQ ID NO 11
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 11

```
gtatgtcgag aacgctagtg ttagcatcgc gctgg                               35
```

<210> SEQ ID NO 12
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 12

```
ccagcgcgat gctaacacta gcgttctcga catac                               35
```

<210> SEQ ID NO 13
<211> LENGTH: 35
<212> TYPE: DNA
<213> ORGANISM: Artificial Sequence
<220> FEATURE:

<223> OTHER INFORMATION: Synthetic Oligonucleotide

<400> SEQUENCE: 13
ctaaagttag catctcgctg gcgaccgttg ttctg    35

<210> SEQ ID NO 14
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 14
cagaacaacg gtcgccagcg agatgctaac tttag    35

<210> SEQ ID NO 15
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 15
ctaaagttag catcgcgctg gggaccgttg ttctg    35

<210> SEQ ID NO 16
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 16
cagaacaacg gtccccagcg cgatgctaac tttag    35

<210> SEQ ID NO 17
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 17
catcgcgctg gcgacccttg ttctgaactc    30

<210> SEQ ID NO 18
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 18
gagttcagaa caagggtcgc cagcgcgatg    30

<210> SEQ ID NO 19
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 19
ccggccgtct gattgccgac accaaaacct atcag    35

<210> SEQ ID NO 20

```
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 20
ctgataggtt ttggtgtcgg caatcagacg gccgg                              35

<210> SEQ ID NO 21
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 21
ccaaaaccta tcaggctgca cgtaaccgtg g                                  31

<210> SEQ ID NO 22
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 22
ccacggttac gtgcagcctg ataggttttg g                                  31

<210> SEQ ID NO 23
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 23
cgtcgtctgc tgttcgagac cgcgcgtgta atgc                               34

<210> SEQ ID NO 24
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 24
gcattacacg cgcggtctcg aacagcagac gacg                               34

<210> SEQ ID NO 25
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 25
gtaccgcgat ggcttcacca tcagcgataa agaaatg                            37

<210> SEQ ID NO 26
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 26
```

```
catttcttta tcgctgatgg tgaagccatc gcggtac                                37
```

<210> SEQ ID NO 27
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 27

```
ccgcgatggc ttcggcctca gcgataaag                                         29
```

<210> SEQ ID NO 28
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 28

```
ctttatcgct gaggccgaag ccatcgcgg                                         29
```

<210> SEQ ID NO 29
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 29

```
gtcagcgccc ggttgaagcg tacttttctg ttgcag                                 36
```

<210> SEQ ID NO 30
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 30

```
ctgcaacaga aaagtacgct tcaaccgggc gctgac                                 36
```

<210> SEQ ID NO 31
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 31

```
gtcagcgccc ggttgaatgt tacttttctg ttgcag                                 36
```

<210> SEQ ID NO 32
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 32

```
ctgcaacaga aaagtaacat tcaaccgggc gctgac                                 36
```

<210> SEQ ID NO 33
<211> LENGTH: 36
<212> TYPE: DNA
<213> ORGANISM: Artificial Sequence
<220> FEATURE:

<223> OTHER INFORMATION: Synthetic Oligonucleotide

<400> SEQUENCE: 33
gtcagcgccc ggttgaagac tacttttctg ttgcag            36

<210> SEQ ID NO 34
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 34
ctgcaacaga aagtagtct tcaaccgggc gctgac            36

<210> SEQ ID NO 35
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 35
gtcagcgccc ggttgaagag tacttttctg ttgcag            36

<210> SEQ ID NO 36
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 36
ctgcaacaga aagtactct tcaaccgggc gctgac            36

<210> SEQ ID NO 37
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 37
gtcagcgccc ggttgaattt tacttttctg ttgcag            36

<210> SEQ ID NO 38
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 38
ctgcaacaga aagtaaaat tcaaccgggc gctgac            36

<210> SEQ ID NO 39
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 39
gtcagcgccc ggttgaaggg tacttttctg ttgcag            36

<210> SEQ ID NO 40

```
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 40
ctgcaacaga aaagtaccct tcaaccgggc gctgac                              36

<210> SEQ ID NO 41
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 41
gtcagcgccc ggttgaacac tactttctg ttgcag                               36

<210> SEQ ID NO 42
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 42
ctgcaacaga aaagtagtgt tcaaccgggc gctgac                              36

<210> SEQ ID NO 43
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 43
gtcagcgccc ggttgaaatc tactttctg ttgcag                               36

<210> SEQ ID NO 44
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 44
ctgcaacaga aaagtagatt tcaaccgggc gctgac                              36

<210> SEQ ID NO 45
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 45
gtcagcgccc ggttgaaaaa tactttctg ttgcag                               36

<210> SEQ ID NO 46
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 46
```

```
ctgcaacaga aaagtatttt tcaaccgggc gctgac                                36
```

<210> SEQ ID NO 47
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 47

```
gtcagcgccc ggttgaattg tacttttctg ttgcag                                36
```

<210> SEQ ID NO 48
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 48

```
ctgcaacaga aaagtacaat tcaaccgggc gctgac                                36
```

<210> SEQ ID NO 49
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 49

```
gtcagcgccc ggttgaaaac tacttttctg ttgcag                                36
```

<210> SEQ ID NO 50
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 50

```
ctgcaacaga aaagtagttt tcaaccgggc gctgac                                36
```

<210> SEQ ID NO 51
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 51

```
gtcagcgccc ggttgaacag tacttttctg ttgcag                                36
```

<210> SEQ ID NO 52
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 52

```
ctgcaacaga aaagtactgt tcaaccgggc gctgac                                36
```

<210> SEQ ID NO 53
<211> LENGTH: 36
<212> TYPE: DNA
<213> ORGANISM: Artificial Sequence
<220> FEATURE:

<223> OTHER INFORMATION: Synthetic Oligonucleotide

<400> SEQUENCE: 53
gtcagcgccc ggttgaaccg tacttttctg ttgcag      36

<210> SEQ ID NO 54
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 54
ctgcaacaga aagtacggt tcaaccgggc gctgac      36

<210> SEQ ID NO 55
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 55
gtcagcgccc ggttgaaagg tacttttctg ttgcag      36

<210> SEQ ID NO 56
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 56
ctgcaacaga aagtacctt tcaaccgggc gctgac      36

<210> SEQ ID NO 57
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 57
gtcagcgccc ggttgaatcg tacttttctg ttgcag      36

<210> SEQ ID NO 58
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 58
ctgcaacaga aagtacgat tcaaccgggc gctgac      36

<210> SEQ ID NO 59
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 59
gtcagcgccc ggttgaaacg tacttttctg ttgcag      36

<210> SEQ ID NO 60

```
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 60
ctgcaacaga aaagtacgtt tcaaccgggc gctgac                              36

<210> SEQ ID NO 61
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 61
gtcagcgccc ggttgaagtg tacttttctg ttgcag                              36

<210> SEQ ID NO 62
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 62
ctgcaacaga aaagtacact tcaaccgggc gctgac                              36

<210> SEQ ID NO 63
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 63
gtcagcgccc ggttgaatgg tacttttctg ttgcag                              36

<210> SEQ ID NO 64
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 64
ctgcaacaga aaagtaccat tcaaccgggc gctgac                              36

<210> SEQ ID NO 65
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 65
gtcagcgccc ggttgaatat tacttttctg ttgcag                              36

<210> SEQ ID NO 66
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 66
```

```
ctgcaacaga aaagtaatat tcaaccgggc gctgac                              36
```

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 67

```
cctcttgcct gtgcgtaatc ctggacg                                        27
```

<210> SEQ ID NO 68
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 68

```
cgtccaggat tacgcacagg caagagg                                        27
```

<210> SEQ ID NO 69
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 69

```
cctcttgcct ggacgtaatc ctggacg                                        27
```

<210> SEQ ID NO 70
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 70

```
cgtccaggat tacgtccagg caagagg                                        27
```

<210> SEQ ID NO 71
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 71

```
cctcttgcct ggaagtaatc ctggacg                                        27
```

<210> SEQ ID NO 72
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 72

```
cgtccaggat tacttccagg caagagg                                        27
```

<210> SEQ ID NO 73
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 73
cctcttgcct gttcgtaatc ctggacg					27

<210> SEQ ID NO 74
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 74
cgtccaggat tacgaacagg caagagg					27

<210> SEQ ID NO 75
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 75
cctcttgcct gggcgtaatc ctggacg					27

<210> SEQ ID NO 76
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 76
cgtccaggat tacgcccagg caagagg					27

<210> SEQ ID NO 77
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 77
cctcttgcct gcacgtaatc ctggacg					27

<210> SEQ ID NO 78
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 78
cgtccaggat tacgtgcagg caagagg					27

<210> SEQ ID NO 79
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 79
cctcttgcct gatcgtaatc ctggacg					27

<210> SEQ ID NO 80

```
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 80
cgtccaggat tacgatcagg caagagg                                               27

<210> SEQ ID NO 81
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 81
cctcttgcct gaaagtaatc ctggacg                                               27

<210> SEQ ID NO 82
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 82
cgtccaggat tactttcagg caagagg                                               27

<210> SEQ ID NO 83
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 83
cctcttgcct gctcgtaatc ctggacg                                               27

<210> SEQ ID NO 84
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 84
cgtccaggat tacgagcagg caagagg                                               27

<210> SEQ ID NO 85
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 85
cctcttgcct gatggtaatc ctggacg                                               27

<210> SEQ ID NO 86
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 86
```
cgtccaggat taccatcagg caagagg                                              27

<210> SEQ ID NO 87
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 87
cctcttgcct gaacgtaatc ctggacg                                              27

<210> SEQ ID NO 88
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 88
cgtccaggat tacgttcagg caagagg                                              27

<210> SEQ ID NO 89
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 89
cctcttgcct gcccgtaatc ctggacg                                              27

<210> SEQ ID NO 90
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 90
cgtccaggat tacgggcagg caagagg                                              27

<210> SEQ ID NO 91
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 91
cctcttgcct gcaagtaatc ctggacg                                              27

<210> SEQ ID NO 92
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 92
cgtccaggat tacttgcagg caagagg                                              27

<210> SEQ ID NO 93
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 93
cctcttgcct gcgcgtaatc ctggacg              27

<210> SEQ ID NO 94
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 94
cgtccaggat tacgcgcagg caagagg              27

<210> SEQ ID NO 95
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 95
cctcttgcct gtccgtaatc ctggacg              27

<210> SEQ ID NO 96
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 96
cgtccaggat tacggacagg caagagg              27

<210> SEQ ID NO 97
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 97
cctcttgcct gaccgtaatc ctggacg              27

<210> SEQ ID NO 98
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 98
cgtccaggat tacggtcagg caagagg              27

<210> SEQ ID NO 99
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 99
cctcttgcct ggtcgtaatc ctggacg              27

<210> SEQ ID NO 100

```
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 100
cgtccaggat tacgaccagg caagagg                                          27

<210> SEQ ID NO 101
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 101
cctcttgcct gtgggtaatc ctggacg                                          27

<210> SEQ ID NO 102
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 102
cgtccaggat tacccacagg caagagg                                          27

<210> SEQ ID NO 103
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 103
cctcttgcct gtacgtaatc ctggacg                                          27

<210> SEQ ID NO 104
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 104
cgtccaggat tacgtacagg caagagg                                          27

<210> SEQ ID NO 105
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 105
ggcctgctgg cctccgctac caaggaagcg                                       30

<210> SEQ ID NO 106
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 106
```

```
cgcttccttg gtagcggagg ccagcaggcc                                    30
```

<210> SEQ ID NO 107
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 107

```
ggcctgctgg cctcctgtac caaggaagcg                                    30
```

<210> SEQ ID NO 108
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 108

```
cgcttccttg gtacaggagg ccagcaggcc                                    30
```

<210> SEQ ID NO 109
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 109

```
ggcctgctgg cctccgatac caaggaagcg                                    30
```

<210> SEQ ID NO 110
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 110

```
cgcttccttg gtatcggagg ccagcaggcc                                    30
```

<210> SEQ ID NO 111
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 111

```
ggcctgctgg cctccgaaac caaggaagcg                                    30
```

<210> SEQ ID NO 112
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 112

```
cgcttccttg gtttcggagg ccagcaggcc                                    30
```

<210> SEQ ID NO 113
<211> LENGTH: 30
<212> TYPE: DNA
<213> ORGANISM: Artificial Sequence
<220> FEATURE:

<223> OTHER INFORMATION: Synthetic Oligonucleotide

<400> SEQUENCE: 113
ggcctgctgg cctcctttac caaggaagcg        30

<210> SEQ ID NO 114
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 114
cgcttccttg gtaaaggagg ccagcaggcc        30

<210> SEQ ID NO 115
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 115
ggcctgctgg cctccggtac caaggaagcg        30

<210> SEQ ID NO 116
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 116
cgcttccttg gtaccggagg ccagcaggcc        30

<210> SEQ ID NO 117
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 117
ggcctgctgg cctcccatac caaggaagcg        30

<210> SEQ ID NO 118
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 118
cgcttccttg gtatgggagg ccagcaggcc        30

<210> SEQ ID NO 119
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 119
ggcctgctgg cctccattac caaggaagcg        30

<210> SEQ ID NO 120

```
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 120
cgcttccttg gtaatggagg ccagcaggcc                                    30

<210> SEQ ID NO 121
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 121
ggcctgctgg cctccaaaac caaggaagcg                                    30

<210> SEQ ID NO 122
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 122
cgcttccttg gttttggagg ccagcaggcc                                    30

<210> SEQ ID NO 123
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 123
ggcctgctgg cctccttaac caaggaagcg                                    30

<210> SEQ ID NO 124
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 124
cgcttccttg gttaaggagg ccagcaggcc                                    30

<210> SEQ ID NO 125
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 125
ggcctgctgg cctccatgac caaggaagcg                                    30

<210> SEQ ID NO 126
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 126
```

```
cgcttccttg gtcatggagg ccagcaggcc                                              30
```

<210> SEQ ID NO 127
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 127

```
ggcctgctgg cctccaatac caaggaagcg                                              30
```

<210> SEQ ID NO 128
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 128

```
cgcttccttg gtattggagg ccagcaggcc                                              30
```

<210> SEQ ID NO 129
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 129

```
ggcctgctgg cctcccctac caaggaagcg                                              30
```

<210> SEQ ID NO 130
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 130

```
cgcttccttg gtagggagg ccagcaggcc                                               30
```

<210> SEQ ID NO 131
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 131

```
ggcctgctgg cctccgaaac caaggaagcg                                              30
```

<210> SEQ ID NO 132
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 132

```
cgcttccttg gtttcggagg ccagcaggcc                                              30
```

<210> SEQ ID NO 133
<211> LENGTH: 30
<212> TYPE: DNA
<213> ORGANISM: Artificial Sequence
<220> FEATURE:

<223> OTHER INFORMATION: Synthetic Oligonucleotide

<400> SEQUENCE: 133
ggcctgctgg cctcccgtac caaggaagcg                                30

<210> SEQ ID NO 134
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 134
cgcttccttg gtacgggagg ccagcaggcc                                30

<210> SEQ ID NO 135
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 135
ggcctgctgg cctcctctac caaggaagcg                                30

<210> SEQ ID NO 136
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 136
cgcttccttg gtagaggagg ccagcaggcc                                30

<210> SEQ ID NO 137
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 137
ggcctgctgg cctccactac caaggaagcg                                30

<210> SEQ ID NO 138
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 138
cgcttccttg gtagtggagg ccagcaggcc                                30

<210> SEQ ID NO 139
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 139
ggcctgctgg cctccgttac caaggaagcg                                30

<210> SEQ ID NO 140

```
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 140
cgcttccttg gtaacggagg ccagcaggcc                                         30

<210> SEQ ID NO 141
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 141
ggcctgctgg cctcctggac caaggaagcg                                         30

<210> SEQ ID NO 142
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 142
cgcttccttg gtccaggagg ccagcaggcc                                         30

<210> SEQ ID NO 143
<211> LENGTH: 891
<212> TYPE: DNA
<213> ORGANISM: Artificial Sequence
<220> FEATURE:
<223> OTHER INFORMATION: Synthetic cDNA
<220> FEATURE:
<221> NAME/KEY: CDS
<222> LOCATION: (1)..(891)

<400> SEQUENCE: 143 atg ttt gat ttc aat gaa tat atg aaa tcg aaa gca gtt gca gtt gat          48
Met Phe Asp Phe Asn Glu Tyr Met Lys Ser Lys Ala Val Ala Val Asp
 1               5                  10                  15 gct gcg ctt gac aaa gcg att ccg ctg gaa tac cct gaa aag att cac          96
Ala Ala Leu Asp Lys Ala Ile Pro Leu Glu Tyr Pro Glu Lys Ile His
             20                  25                  30 gaa tcg atg cgc tat agt ctg ctg gct ggt ggc aaa cgc gtg cgc cca         144
Glu Ser Met Arg Tyr Ser Leu Leu Ala Gly Gly Lys Arg Val Arg Pro
         35                  40                  45 gct ctt tgc att gcg gca tgt gag ctg gta ggc ggt tcc cag gat ctg         192
Ala Leu Cys Ile Ala Ala Cys Glu Leu Val Gly Gly Ser Gln Asp Leu
     50                  55                  60 gct atg cca acg gcg tgc gca atg gaa atg atc cat aca atg tcc ctg         240
Ala Met Pro Thr Ala Cys Ala Met Glu Met Ile His Thr Met Ser Leu
 65                  70                  75                  80 atc cac gat gat ctg ccg tgt atg gat aat gat gac ttc cgc cgt gga         288
Ile His Asp Asp Leu Pro Cys Met Asp Asn Asp Asp Phe Arg Arg Gly
                 85                  90                  95 aaa ccg act aac cat aaa gta ttt ggc gag gac act gca gtg ttg gca         336
Lys Pro Thr Asn His Lys Val Phe Gly Glu Asp Thr Ala Val Leu Ala
            100                 105                 110 gga gac gcc ctg ttg agc ttt gcc ttt gaa cat att gcc gtc gcg acc         384
Gly Asp Ala Leu Leu Ser Phe Ala Phe Glu His Ile Ala Val Ala Thr
        115                 120                 125 tca aaa aca gtt cct tct gat cgt acc ctg cgc gtc atc agt gag tta         432
```

```
Ser Lys Thr Val Pro Ser Asp Arg Thr Leu Arg Val Ile Ser Glu Leu
    130                 135                 140 ggt aag acc att ggc agc cag ggg ctg gta ggc ggc cag gtc gtg gat      480
Gly Lys Thr Ile Gly Ser Gln Gly Leu Val Gly Gly Gln Val Val Asp
145                 150                 155                 160 atc acg tct gaa ggt gac gcg aat gtg gat ctt aag acc tta gag tgg      528
Ile Thr Ser Glu Gly Asp Ala Asn Val Asp Leu Lys Thr Leu Glu Trp
                165                 170                 175 att cac atc cat aaa acg gcc gtg ctg ctg gaa tgc tcg gtt gtg tcc      576
Ile His Ile His Lys Thr Ala Val Leu Leu Glu Cys Ser Val Val Ser
            180                 185                 190 ggt ggg atc ctg ggg ggc gcc act gag gac gaa atc gcc cgt att cgc      624
Gly Gly Ile Leu Gly Gly Ala Thr Glu Asp Glu Ile Ala Arg Ile Arg
        195                 200                 205 cgt tat gca cgg tgt gtg ggc ctc ttg ttt caa gtc gtg gat gat att      672
Arg Tyr Ala Arg Cys Val Gly Leu Leu Phe Gln Val Val Asp Asp Ile
    210                 215                 220 ctg gat gtg acg aaa tct agt gag gag ctc ggt aaa acc gcg ggc aag      720
Leu Asp Val Thr Lys Ser Ser Glu Glu Leu Gly Lys Thr Ala Gly Lys
225                 230                 235                 240 gat ctc ctg acc gac aag gcg acg tac ccg aaa ctg atg ggt ttg gaa      768
Asp Leu Leu Thr Asp Lys Ala Thr Tyr Pro Lys Leu Met Gly Leu Glu
                245                 250                 255 aag gct aag gag ttt gct gcc gaa tta gcg acc aga gcc aaa gaa gaa      816
Lys Ala Lys Glu Phe Ala Ala Glu Leu Ala Thr Arg Ala Lys Glu Glu
            260                 265                 270 ctc tct tct ttc gac cag atc aag gta gcg ccc ctt tta ggg ctc gcc      864
Leu Ser Ser Phe Asp Gln Ile Lys Val Ala Pro Leu Leu Gly Leu Ala
        275                 280                 285 gat tac att gcg ttt cgt cag ttg tga                                  891
Asp Tyr Ile Ala Phe Arg Gln Leu
    290                 295

<210> SEQ ID NO 144
<211> LENGTH: 296
<212> TYPE: PRT
<213> ORGANISM: Artificial Sequence
<220> FEATURE:
<223> OTHER INFORMATION: Synthetic Construct

<400> SEQUENCE: 144

Met Phe Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
                20                  25                  30

Glu Ser Met Arg Tyr Ser Leu Leu Ala Gly Gly Lys Arg Val Arg Pro
            35                  40                  45

Ala Leu Cys Ile Ala Ala Cys Glu Leu Val Gly Gly Ser Gln Asp Leu
        50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95

Lys Pro Thr Asn His Lys Val Phe Gly Glu Asp Thr Ala Val Leu Ala
            100                 105                 110

Gly Asp Ala Leu Leu Ser Phe Ala Phe Glu His Ile Ala Val Ala Thr
        115                 120                 125

Ser Lys Thr Val Pro Ser Asp Arg Thr Leu Arg Val Ile Ser Glu Leu
    130                 135                 140
```

Gly Lys Thr Ile Gly Ser Gln Gly Leu Val Gly Gly Gln Val Val Asp
145                 150                 155                 160

Ile Thr Ser Glu Gly Asp Ala Asn Val Asp Leu Lys Thr Leu Glu Trp
            165                 170                 175

Ile His Ile His Lys Thr Ala Val Leu Leu Glu Cys Ser Val Val Ser
        180                 185                 190

Gly Gly Ile Leu Gly Gly Ala Thr Glu Asp Glu Ile Ala Arg Ile Arg
    195                 200                 205

Arg Tyr Ala Arg Cys Val Gly Leu Leu Phe Gln Val Val Asp Asp Ile
210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu
            245                 250                 255

Lys Ala Lys Glu Phe Ala Ala Glu Leu Ala Thr Arg Ala Lys Glu Glu
        260                 265                 270

Leu Ser Ser Phe Asp Gln Ile Lys Val Ala Pro Leu Leu Gly Leu Ala
    275                 280                 285

Asp Tyr Ile Ala Phe Arg Gln Leu
290                 295

<210> SEQ ID NO 145
<211> LENGTH: 2505
<212> TYPE: DNA
<213> ORGANISM: Artificial Sequence
<220> FEATURE:
<223> OTHER INFORMATION: Synthetic cDNA
<220> FEATURE:
<221> NAME/KEY: CDS
<222> LOCATION: (1)..(2505)

<400> SEQUENCE: 145

```
atg gct cag cac tgc gtc cgt tcc cac ctg cgt ctg cgt tgg aat tgc        48
Met Ala Gln His Cys Val Arg Ser His Leu Arg Leu Arg Trp Asn Cys
1               5                   10                  15 gtt ggc atc cac gcg tct gct gct gaa act cgt ccg gat cag ctg ccg        96
Val Gly Ile His Ala Ser Ala Ala Glu Thr Arg Pro Asp Gln Leu Pro
                20                  25                  30 cag gaa gaa cgt ttt gtg agc cgt ctg aac gcg gac tac cac ccg gcg       144
Gln Glu Glu Arg Phe Val Ser Arg Leu Asn Ala Asp Tyr His Pro Ala
            35                  40                  45 gtg tgg aaa gat gat ttt atc gat tct ctg act tcc cca aac agc cat       192
Val Trp Lys Asp Asp Phe Ile Asp Ser Leu Thr Ser Pro Asn Ser His
        50                  55                  60 gcg acc tcc aaa agc tcc gtt gat gaa acc atc aac aaa cgc att cag       240
Ala Thr Ser Lys Ser Ser Val Asp Glu Thr Ile Asn Lys Arg Ile Gln
65                  70                  75                  80 act ctg gtg aag gag atc cag tgc atg ttc cag tcc atg ggt gat ggt       288
Thr Leu Val Lys Glu Ile Gln Cys Met Phe Gln Ser Met Gly Asp Gly
                85                  90                  95 gaa acc aat ccg tct gca tat gac acc gcg tgg gtg gct cgc att ccg       336
Glu Thr Asn Pro Ser Ala Tyr Asp Thr Ala Trp Val Ala Arg Ile Pro
                100                 105                 110 agc att gat ggt tcc ggt gcg ccg cag ttt ccg cag acg ctg caa tgg       384
Ser Ile Asp Gly Ser Gly Ala Pro Gln Phe Pro Gln Thr Leu Gln Trp
            115                 120                 125 atc ctg aac aac cag ctg cct gat ggt agc tgg ggt gaa gag tgc atc       432
Ile Leu Asn Asn Gln Leu Pro Asp Gly Ser Trp Gly Glu Glu Cys Ile
        130                 135                 140 ttc ctg gct tac gat cgc gtt ctg aac acg ctg gct tgt ctg ctg act       480
```

```
                        -continued

Phe Leu Ala Tyr Asp Arg Val Leu Asn Thr Leu Ala Cys Leu Leu Thr
145                 150                 155                 160 ctg aaa atc tgg aac aag ggt gac atc cag gta caa aaa ggc gtt gag      528
Leu Lys Ile Trp Asn Lys Gly Asp Ile Gln Val Gln Lys Gly Val Glu
                165                 170                 175 ttt gtg cgc aaa cac atg gaa gag atg aaa gat gaa gca gac aac cat      576
Phe Val Arg Lys His Met Glu Glu Met Lys Asp Glu Ala Asp Asn His
            180                 185                 190 cgt cca tct ggc ttc gaa gtg gta ttt cca gcg atg ctg gat gag gcg      624
Arg Pro Ser Gly Phe Glu Val Val Phe Pro Ala Met Leu Asp Glu Ala
        195                 200                 205 aaa agc ctg ggc ctg gat ctg ccg tac cac ctg ccg ttc atc agc cag      672
Lys Ser Leu Gly Leu Asp Leu Pro Tyr His Leu Pro Phe Ile Ser Gln
    210                 215                 220 atc cac caa aaa cgt cag aaa aag ctg cag aag atc ccg ctg aac gtc      720
Ile His Gln Lys Arg Gln Lys Lys Leu Gln Lys Ile Pro Leu Asn Val
225                 230                 235                 240 ctg cat aac cat caa act gct ctg ctg tac tct ctg gaa ggt ctg caa      768
Leu His Asn His Gln Thr Ala Leu Leu Tyr Ser Leu Glu Gly Leu Gln
                245                 250                 255 gat gtt gtg gac tgg cag gaa atc act aac ctg caa agc cgt gac ggt      816
Asp Val Val Asp Trp Gln Glu Ile Thr Asn Leu Gln Ser Arg Asp Gly
            260                 265                 270 agc ttt ctg agc tct ccg gca tct act gct tgt gtt ttt atg cac acc      864
Ser Phe Leu Ser Ser Pro Ala Ser Thr Ala Cys Val Phe Met His Thr
        275                 280                 285 cag aac aaa cgc tgc ctg cat ttc ctg aac ttc gtt ctg tct aag ttc      912
Gln Asn Lys Arg Cys Leu His Phe Leu Asn Phe Val Leu Ser Lys Phe
    290                 295                 300 ggt gat tac gta cct tgc cac tac ccg ctg gac ctg ttc gag cgt ctg      960
Gly Asp Tyr Val Pro Cys His Tyr Pro Leu Asp Leu Phe Glu Arg Leu
305                 310                 315                 320 tgg gcg gtt gat acg gtt gag cgt ctg ggc att gac cgt tac ttt aag     1008
Trp Ala Val Asp Thr Val Glu Arg Leu Gly Ile Asp Arg Tyr Phe Lys
                325                 330                 335 aaa gag atc aaa gag agc ctg gat tat gtt tac cgc tat tgg gac gcg     1056
Lys Glu Ile Lys Glu Ser Leu Asp Tyr Val Tyr Arg Tyr Trp Asp Ala
            340                 345                 350 gag cgt ggc gta ggt tgg gcg cgc tgt aac cca att ccg gac gtt gac     1104
Glu Arg Gly Val Gly Trp Ala Arg Cys Asn Pro Ile Pro Asp Val Asp
        355                 360                 365 gat acg gct atg ggt ctg cgc atc ctg cgc ctg cac ggt tac aac gta     1152
Asp Thr Ala Met Gly Leu Arg Ile Leu Arg Leu His Gly Tyr Asn Val
    370                 375                 380 agc tct gat gta ctg gag aac ttt cgc gac gaa aaa ggc gat ttc ttc     1200
Ser Ser Asp Val Leu Glu Asn Phe Arg Asp Glu Lys Gly Asp Phe Phe
385                 390                 395                 400 tgt ttc gcg ggt cag acc caa atc ggc gtt acc gac aac ctg aac ctg     1248
Cys Phe Ala Gly Gln Thr Gln Ile Gly Val Thr Asp Asn Leu Asn Leu
                405                 410                 415 tac cgc tgc tct cag gtt tgc ttc ccg ggt gag aaa atc atg gag gag     1296
Tyr Arg Cys Ser Gln Val Cys Phe Pro Gly Glu Lys Ile Met Glu Glu
            420                 425                 430 gct aaa acg ttc acg acc aac cat ctg cag aat gct ctg gcg aag aat     1344
Ala Lys Thr Phe Thr Thr Asn His Leu Gln Asn Ala Leu Ala Lys Asn
        435                 440                 445 aac gca ttt gac aaa tgg gcg gtt aaa aag gat ctg cca ggt gaa gtc     1392
Asn Ala Phe Asp Lys Trp Ala Val Lys Lys Asp Leu Pro Gly Glu Val
    450                 455                 460 gag tac gca att aag tac ccg tgg cat cgc agc atg ccg cgc ctg gaa     1440
```

```
                                        -continued

Glu Tyr Ala Ile Lys Tyr Pro Trp His Arg Ser Met Pro Arg Leu Glu
465                 470                 475                 480 gcg cgt tct tat atc gaa cag ttc ggt tct aac gac gtc tgg ctg ggc    1488
Ala Arg Ser Tyr Ile Glu Gln Phe Gly Ser Asn Asp Val Trp Leu Gly
                    485                 490                 495 aaa act gtt tac aaa atg ctg tac gtc tcc aac gaa aaa tac ctg gaa    1536
Lys Thr Val Tyr Lys Met Leu Tyr Val Ser Asn Glu Lys Tyr Leu Glu
            500                 505                 510 ctg gct aaa ctg gat ttc aac atg gta cag gca ctg cac cag aag gag    1584
Leu Ala Lys Leu Asp Phe Asn Met Val Gln Ala Leu His Gln Lys Glu
        515                 520                 525 acg cag cat atc gtt tct tgg tgg cgt gaa agc ggt ttc aac gac ctg    1632
Thr Gln His Ile Val Ser Trp Trp Arg Glu Ser Gly Phe Asn Asp Leu
    530                 535                 540 acc ttt acc cgt cag cgc ccg gtt gaa atg tac ttt tct gtt gca gta    1680
Thr Phe Thr Arg Gln Arg Pro Val Glu Met Tyr Phe Ser Val Ala Val
545                 550                 555                 560 agc atg ttc gaa cct gag ttc gct gct tgt cgt atc gcg tac gca aaa    1728
Ser Met Phe Glu Pro Glu Phe Ala Ala Cys Arg Ile Ala Tyr Ala Lys
                565                 570                 575 acc tct tgc ctg gcc gta atc ctg gac gat ctg tac gac acg cac ggt    1776
Thr Ser Cys Leu Ala Val Ile Leu Asp Asp Leu Tyr Asp Thr His Gly
            580                 585                 590 tcc ctg gat gac ctg aaa ctg ttc tct gaa gcg gtt cgt cgt tgg gat    1824
Ser Leu Asp Asp Leu Lys Leu Phe Ser Glu Ala Val Arg Arg Trp Asp
        595                 600                 605 atc agc gta ctg gac tct gtg cgc gat aac cag ctg aaa gtg tgc ttt    1872
Ile Ser Val Leu Asp Ser Val Arg Asp Asn Gln Leu Lys Val Cys Phe
    610                 615                 620 ctg ggt ctg tac aac acg gtg aac ggc ttc ggt aag gat ggt ctg aaa    1920
Leu Gly Leu Tyr Asn Thr Val Asn Gly Phe Gly Lys Asp Gly Leu Lys
625                 630                 635                 640 gaa cag ggt cgc gat gtc ctg ggt tac ctg cgt aaa gtt tgg gag ggc    1968
Glu Gln Gly Arg Asp Val Leu Gly Tyr Leu Arg Lys Val Trp Glu Gly
                645                 650                 655 ctg ctg gcc tcc tat acc aag gaa gcg gag tgg tcc gct gct aaa tat    2016
Leu Leu Ala Ser Tyr Thr Lys Glu Ala Glu Trp Ser Ala Ala Lys Tyr
            660                 665                 670 gtg ccg act ttc aac gag tat gtc gag aac gct aaa gtt agc atc gcg    2064
Val Pro Thr Phe Asn Glu Tyr Val Glu Asn Ala Lys Val Ser Ile Ala
        675                 680                 685 ctg gcg acc gtt gtt ctg aac tcc atc ttc ttc acc ggc gaa ctg ctg    2112
Leu Ala Thr Val Val Leu Asn Ser Ile Phe Phe Thr Gly Glu Leu Leu
    690                 695                 700 ccg gat tat att ctg cag caa gtt gac ctg cgt agc aaa ttt ctg cac    2160
Pro Asp Tyr Ile Leu Gln Gln Val Asp Leu Arg Ser Lys Phe Leu His
705                 710                 715                 720 ctg gtt tcc ctg acc ggc cgt ctg att aac gac acc aaa acc tat cag    2208
Leu Val Ser Leu Thr Gly Arg Leu Ile Asn Asp Thr Lys Thr Tyr Gln
                725                 730                 735 gct gaa cgt aac cgt ggt gag ctg gtg agc agc gtg cag tgc tac atg    2256
Ala Glu Arg Asn Arg Gly Glu Leu Val Ser Ser Val Gln Cys Tyr Met
            740                 745                 750 cgt gag aac ccg gag tgt acc gag gag gaa gct ctg tct cat gtt tac    2304
Arg Glu Asn Pro Glu Cys Thr Glu Glu Glu Ala Leu Ser His Val Tyr
        755                 760                 765 ggc att att gat aac gca ctg aaa gag ctg aac tgg gag ctg gcg aac    2352
Gly Ile Ile Asp Asn Ala Leu Lys Glu Leu Asn Trp Glu Leu Ala Asn
    770                 775                 780 cca gcg agc aac gct ccg ctg tgc gtt cgt cgt ctg ctg ttc aac acc    2400
```

```
              Pro Ala Ser Asn Ala Pro Leu Cys Val Arg Arg Leu Leu Phe Asn Thr
              785                 790                 795                 800 gcg cgt gta atg cag ctg ttc tac atg tac cgc gat ggc ttc ggc atc              2448
Ala Arg Val Met Gln Leu Phe Tyr Met Tyr Arg Asp Gly Phe Gly Ile
                    805                 810                 815 agc gat aaa gaa atg aaa gat cat gtg tct cgc acc ctg ttt gac ccg              2496
Ser Asp Lys Glu Met Lys Asp His Val Ser Arg Thr Leu Phe Asp Pro
                820                 825                 830 gta gca taa                                                                   2505
Val Ala <210> SEQ ID NO 146
<211> LENGTH: 834
<212> TYPE: PRT
<213> ORGANISM: Artificial Sequence
<220> FEATURE:
<223> OTHER INFORMATION: Synthetic Construct

<400> SEQUENCE: 146

Met Ala Gln His Cys Val Arg Ser His Leu Arg Leu Arg Trp Asn Cys
1               5                   10                  15

Val Gly Ile His Ala Ser Ala Glu Thr Arg Pro Asp Gln Leu Pro
            20                  25                  30

Gln Glu Glu Arg Phe Val Ser Arg Leu Asn Ala Asp Tyr His Pro Ala
        35                  40                  45

Val Trp Lys Asp Asp Phe Ile Asp Ser Leu Thr Ser Pro Asn Ser His
    50                  55                  60

Ala Thr Ser Lys Ser Ser Val Asp Glu Thr Ile Asn Lys Arg Ile Gln
65                  70                  75                  80

Thr Leu Val Lys Glu Ile Gln Cys Met Phe Gln Ser Met Gly Asp Gly
                85                  90                  95

Glu Thr Asn Pro Ser Ala Tyr Asp Thr Ala Trp Val Ala Arg Ile Pro
            100                 105                 110

Ser Ile Asp Gly Ser Gly Ala Pro Gln Phe Pro Gln Thr Leu Gln Trp
        115                 120                 125

Ile Leu Asn Asn Gln Leu Pro Asp Gly Ser Trp Gly Glu Glu Cys Ile
    130                 135                 140

Phe Leu Ala Tyr Asp Arg Val Leu Asn Thr Leu Ala Cys Leu Leu Thr
145                 150                 155                 160

Leu Lys Ile Trp Asn Lys Gly Asp Ile Gln Val Gln Lys Gly Val Glu
                165                 170                 175

Phe Val Arg Lys His Met Glu Glu Met Lys Asp Glu Ala Asp Asn His
            180                 185                 190

Arg Pro Ser Gly Phe Glu Val Val Phe Pro Ala Met Leu Asp Glu Ala
        195                 200                 205

Lys Ser Leu Gly Leu Asp Leu Pro Tyr His Leu Pro Phe Ile Ser Gln
    210                 215                 220

Ile His Gln Lys Arg Gln Lys Leu Gln Lys Ile Pro Leu Asn Val
225                 230                 235                 240

Leu His Asn His Gln Thr Ala Leu Leu Tyr Ser Leu Glu Gly Leu Gln
                245                 250                 255

Asp Val Val Asp Trp Gln Glu Ile Thr Asn Leu Gln Ser Arg Asp Gly
            260                 265                 270

Ser Phe Leu Ser Ser Pro Ala Ser Thr Ala Cys Val Phe Met His Thr
        275                 280                 285

Gln Asn Lys Arg Cys Leu His Phe Leu Asn Phe Val Leu Ser Lys Phe
    290                 295                 300
```

```
Gly Asp Tyr Val Pro Cys His Tyr Pro Leu Asp Leu Phe Glu Arg Leu
305                 310                 315                 320

Trp Ala Val Asp Thr Val Glu Arg Leu Gly Ile Asp Arg Tyr Phe Lys
            325                 330                 335

Lys Glu Ile Lys Glu Ser Leu Asp Tyr Val Tyr Arg Tyr Trp Asp Ala
            340                 345                 350

Glu Arg Gly Val Gly Trp Ala Arg Cys Asn Pro Ile Pro Asp Val Asp
        355                 360                 365

Asp Thr Ala Met Gly Leu Arg Ile Leu Arg Leu His Gly Tyr Asn Val
370                 375                 380

Ser Ser Asp Val Leu Glu Asn Phe Arg Asp Glu Lys Gly Asp Phe Phe
385                 390                 395                 400

Cys Phe Ala Gly Gln Thr Gln Ile Gly Val Thr Asp Asn Leu Asn Leu
                405                 410                 415

Tyr Arg Cys Ser Gln Val Cys Phe Pro Gly Glu Lys Ile Met Glu Glu
            420                 425                 430

Ala Lys Thr Phe Thr Thr Asn His Leu Gln Asn Ala Leu Ala Lys Asn
        435                 440                 445

Asn Ala Phe Asp Lys Trp Ala Val Lys Lys Asp Leu Pro Gly Glu Val
450                 455                 460

Glu Tyr Ala Ile Lys Tyr Pro Trp His Arg Ser Met Pro Arg Leu Glu
465                 470                 475                 480

Ala Arg Ser Tyr Ile Glu Gln Phe Gly Ser Asn Asp Val Trp Leu Gly
            485                 490                 495

Lys Thr Val Tyr Lys Met Leu Tyr Val Ser Asn Glu Lys Tyr Leu Glu
            500                 505                 510

Leu Ala Lys Leu Asp Phe Asn Met Val Gln Ala Leu His Gln Lys Glu
        515                 520                 525

Thr Gln His Ile Val Ser Trp Trp Arg Glu Ser Gly Phe Asn Asp Leu
530                 535                 540

Thr Phe Thr Arg Gln Arg Pro Val Glu Met Tyr Phe Ser Val Ala Val
545                 550                 555                 560

Ser Met Phe Glu Pro Glu Phe Ala Ala Cys Arg Ile Ala Tyr Ala Lys
                565                 570                 575

Thr Ser Cys Leu Ala Val Ile Leu Asp Asp Leu Tyr Asp Thr His Gly
            580                 585                 590

Ser Leu Asp Asp Leu Lys Leu Phe Ser Glu Ala Val Arg Arg Trp Asp
        595                 600                 605

Ile Ser Val Leu Asp Ser Val Arg Asp Asn Gln Leu Lys Val Cys Phe
610                 615                 620

Leu Gly Leu Tyr Asn Thr Val Asn Gly Phe Gly Lys Asp Gly Leu Lys
625                 630                 635                 640

Glu Gln Gly Arg Asp Val Leu Gly Tyr Leu Arg Lys Val Trp Glu Gly
                645                 650                 655

Leu Leu Ala Ser Tyr Thr Lys Glu Ala Glu Trp Ser Ala Ala Lys Tyr
            660                 665                 670

Val Pro Thr Phe Asn Glu Tyr Val Glu Asn Ala Lys Val Ser Ile Ala
        675                 680                 685

Leu Ala Thr Val Val Leu Asn Ser Ile Phe Phe Thr Gly Glu Leu Leu
690                 695                 700

Pro Asp Tyr Ile Leu Gln Gln Val Asp Leu Arg Ser Lys Phe Leu His
705                 710                 715                 720

Leu Val Ser Leu Thr Gly Arg Leu Ile Asn Asp Thr Lys Thr Tyr Gln
```

```
                        725                 730                 735
Ala Glu Arg Asn Arg Gly Glu Leu Val Ser Ser Val Gln Cys Tyr Met
                    740                 745                 750

Arg Glu Asn Pro Glu Cys Thr Glu Glu Ala Leu Ser His Val Tyr
                755                 760                 765

Gly Ile Ile Asp Asn Ala Leu Lys Glu Leu Asn Trp Glu Leu Ala Asn
            770                 775                 780

Pro Ala Ser Asn Ala Pro Leu Cys Val Arg Arg Leu Leu Phe Asn Thr
785                 790                 795                 800

Ala Arg Val Met Gln Leu Phe Tyr Met Tyr Arg Asp Gly Phe Gly Ile
                805                 810                 815

Ser Asp Lys Glu Met Lys Asp His Val Ser Arg Thr Leu Phe Asp Pro
            820                 825                 830

Val Ala

<210> SEQ ID NO 147
<211> LENGTH: 550
<212> TYPE: PRT
<213> ORGANISM: Nicotiana tabacum

<400> SEQUENCE: 147

Met Ala Ser Ala Ala Val Ala Asn Tyr Glu Glu Ile Val Arg Pro
1               5                   10                  15

Val Ala Asp Phe Ser Pro Ser Leu Trp Gly Asp Gln Phe Leu Ser Phe
                20                  25                  30

Ser Ile Asp Asn Gln Val Ala Glu Lys Tyr Ile Tyr Ala Gln Glu Ile
            35                  40                  45

Glu Ala Leu Lys Glu Gln Thr Arg Ser Met Leu Leu Ala Thr Gly Arg
        50                  55                  60

Lys Leu Ala Asp Thr Leu Asn Leu Ile Asp Ile Ile Glu Arg Leu Gly
65                  70                  75                  80

Ile Ser Tyr His Phe Glu Lys Glu Ile Asp Glu Ile Leu Asp Gln Ile
                85                  90                  95

Tyr Asn Gln Asn Ser Asn Cys Asn Asp Leu Cys Thr Ser Ala Leu Gln
            100                 105                 110

Phe Arg Leu Leu Arg Gln His Gly Phe Asn Ile Ser Pro Glu Ile Phe
        115                 120                 125

Ser Lys Phe Gln Asp Glu Asn Gly Lys Phe Lys Glu Ser Leu Ala Ser
130                 135                 140

Asp Val Leu Gly Leu Leu Asn Leu Tyr Glu Ala Ser His Val Arg Thr
145                 150                 155                 160

His Ala Asp Asp Ile Leu Glu Asp Ala Leu Ala Phe Ser Thr Ile His
                165                 170                 175

Leu Glu Ser Ala Ala Pro His Leu Lys Ser Pro Leu Arg Glu Gln Val
            180                 185                 190

Thr His Ala Leu Glu Gln Cys Leu His Lys Gly Val Pro Arg Val Glu
        195                 200                 205

Thr Arg Phe Phe Ile Ser Ser Ile Tyr Asp Lys Glu Gln Ser Lys Asn
    210                 215                 220

Asn Val Leu Leu Arg Phe Ala Lys Leu Asp Phe Asn Leu Leu Gln Met
225                 230                 235                 240

Leu His Lys Gln Glu Leu Ala Gln Val Ser Arg Trp Trp Lys Asp Leu
                245                 250                 255

Asp Phe Val Thr Thr Leu Pro Tyr Ala Arg Asp Arg Val Val Glu Cys
            260                 265                 270
```

```
Tyr Phe Trp Ala Leu Gly Val Tyr Phe Glu Pro Gln Tyr Ser Gln Ala
            275             280             285

Arg Val Met Leu Val Lys Thr Ile Ser Met Ile Ser Ile Val Asp Asp
        290             295             300

Thr Phe Asp Ala Tyr Gly Thr Val Lys Glu Leu Glu Ala Tyr Thr Asp
305             310             315             320

Ala Ile Gln Arg Trp Asp Ile Asn Glu Ile Asp Arg Leu Pro Asp Tyr
            325             330             335

Met Lys Ile Ser Tyr Lys Ala Ile Leu Asp Leu Tyr Lys Asp Tyr Glu
            340             345             350

Lys Glu Leu Ser Ser Ala Gly Arg Ser His Ile Val Cys His Ala Ile
            355             360             365

Glu Arg Met Lys Glu Val Val Arg Asn Tyr Asn Val Glu Ser Thr Trp
            370             375             380

Phe Ile Glu Gly Tyr Met Pro Pro Val Ser Glu Tyr Leu Ser Asn Ala
385             390             395             400

Leu Ala Thr Thr Thr Tyr Tyr Leu Ala Thr Thr Ser Tyr Leu Gly
                405             410             415

Met Lys Ser Ala Thr Glu Gln Asp Phe Glu Trp Leu Ser Lys Asn Pro
            420             425             430

Lys Ile Leu Glu Ala Ser Val Ile Ile Cys Arg Val Ile Asp Asp Thr
            435             440             445

Ala Thr Tyr Glu Val Glu Lys Ser Arg Gly Gln Ile Ala Thr Gly Ile
    450             455             460

Glu Cys Cys Met Arg Asp Tyr Gly Ile Ser Thr Lys Glu Ala Met Ala
465             470             475             480

Lys Phe Gln Asn Met Ala Glu Thr Ala Trp Lys Asp Ile Asn Glu Gly
                485             490             495

Leu Leu Arg Pro Thr Pro Val Ser Thr Glu Phe Leu Thr Pro Ile Leu
            500             505             510

Asn Leu Ala Arg Ile Val Glu Val Thr Tyr Ile His Asn Leu Asp Gly
            515             520             525

Tyr Thr His Pro Glu Lys Val Leu Lys Pro His Ile Ile Asn Leu Leu
    530             535             540

Val Asp Ser Ile Lys Ile
545             550
```

METHODS FOR MICROBIAL PRODUCTION OF TERPENOIDS

FIELD OF THE INVENTION

The invention relates to the production of one or more terpenoids through recombinant gene expression.

BACKGROUND OF THE INVENTION

The pharmaceutically important diterpene lactone ginkgolides are products of secondary metabolism in *Ginkgo biloba* (*G. biloba*) plants. With over 3000 publications on these compounds since 2001 and annual sales of ~$250 million in the US alone, *G. biloba* extract and its constituents are currently among the most studied and sold phytochemical worldwide[1]. Ginkgolides exhibit bioactivities as antagonists of platelet-activating factor, γ-aminobutyric acid (GABA), and glycine receptors, resulting in therapeutics that are administered for improvement in vascular function, inhibition of thrombosis and embolism, and neuroprotective function[2-5]. Moreover, their potential as cancer therapeutics is under investigation[6]. Currently, the availability of ginkgolides is limited because less than 5 p.p.m of products can be obtained from leaf extract'. Furthermore, the growth of *G. biloba* is also extremely slow. Scalable production routes via plant cell culture and chemical synthesis have been explored; however, they are still far from industrial application. Ginkgolides yield from plant cell culture is relatively low (~40 mg/L)[7] and synthetic methods require more than 20 steps[8].

The success of fermentation technology to produce many fine and commodity chemicals has inspired the heterologous production of several plant terpenoids using microbial hosts[9-13]. In plants, secondary metabolite pathways are genetically programmed and regulated (transcriptionally and post-translationally) so that these chemicals are only synthesized as needed[14, 15]. A particular branch pathway is not designed to overproduce a certain metabolite, but rather, so that the overall metabolism works in concert. A successful microbial production platform, on the other hand, requires that an imported pathway generate a high production yield. Metabolic engineering to increase flux through an engineered plant-derived pathway has been shown to improve terpenoid production[12, 13, 16].

SUMMARY OF THE INVENTION

The extent of product improvement through metabolic engineering is ultimately determined by the biosynthetic capacity of the heterologous pathway in the intracellular environment of the microbial host.[17] Described herein is a novel microbial platform for producing terpenoids and diterpenoids such as levopimaradiene, the key diterpenoid precursor of the ginkgolides. This system was constructed by "tuning" a heterologous pathway to confer overproduction in a microorganism. Codon-optimized *Taxus canadensis* (*T. canadensis*) geranylgeranyl diphosphate synthase (GGPPS) and *Ginkgo biloba* (*G. biloba*) levopimaradiene synthase (LPS) were introduced into *E. coli*. To improve precursor availability, copy number of the MEP pathway in the *E. coli* host was also increased to amplify isopentyl diphosphate (IPP) and dimethylallyl diphosphate (DMAPP), the substrates of GGPPS (FIG. 1*a*). Diterpenoids such as levopimaradiene were successfully synthesized and their production was optimized through the generation of mutations in the LPS and GGPPS enzymes.

Aspects of the invention relate to methods that include recombinantly expressing a terpenoid synthase enzyme and a geranylgeranyl diphosphate synthase (GGPPS) enzyme in a cell that overexpresses one or more components of the non-mevalonate (MEP) pathway. In some embodiments, the cell is a bacterial cell. In certain embodiments, the cell is an *Escherichia coli* cell. In other embodiments, the cell is a Gram-positive cell such as a *Bacillus* cell. In some embodiments, the cell is a yeast cell such as a *Saccharomyces* cell or a *Yarrowia* cell. In other embodiments, the cell is an algal cell or a plant cell.

In some embodiments, the terpenoid synthase enzyme is a diterpenoid synthase enzyme such as a levopimaradiene synthase (LPS) enzyme. In some embodiments, the LPS enzyme is a *Ginkgo biloba* enzyme. In certain embodiments, the LPS enzyme contains one or more mutations. For example, the mutations in the LPS enzyme can be at one or more of the residues selected from the group consisting of: M593, C618, A620, L696, Y700, K723, A729, V731, N838, and I855, corresponding to residues within the full-length, wild-type, *Ginkgo biloba* LPS enzyme, or one or more mutations in equivalent residues within a homologous LPS enzyme. For example, the LPS enzyme can contain one or more mutations selected from the group consisting of: M593I, M593L, C618N, L696Q, K723S, V731L, N838E, I855L, A729G, Y700H, Y700A, Y700C, Y700F, Y700M, Y700W, A620C, A620G, A620S, A620T and A620V, corresponding to mutations at residues within the full-length, wild-type, *Ginkgo biloba* LPS enzyme, or one or more equivalent mutations in a homologous LPS enzyme. In some embodiments, the LPS enzyme contains the mutation M593I and one of the mutations selected from the group consisting of Y700A, Y700C and Y700F, corresponding to mutations at residues within the full-length, wild-type, *Ginkgo biloba* LPS enzyme, or one or more equivalent mutations in a homologous LPS enzyme.

In some embodiments, the GGPPS enzyme is a *Taxus canadensis* enzyme. In certain embodiments, the GGPPS enzyme contains one or more mutations. For example, the GGPPS enzyme can contain a mutation at residue S239 and/or G295, corresponding to residues within the full-length, wild-type, *Taxus canadensis* GGPPS enzyme, or a mutation in one or both equivalent residues within a homologous GGPPS enzyme. In certain embodiments, the GGPPS enzyme contains the mutation S239C and/or G295D, corresponding to mutations at residues within the full-length, wild-type, *Taxus canadensis* GGPPS enzyme, or one or both equivalent mutations in a homologous GGPPS enzyme.

In some embodiments, the LPS enzyme contains the mutation M593I and/or Y700F, corresponding to residues within the full-length wild-type *Ginkgo biloba* LPS enzyme, or one or more equivalent mutations in a homologous LPS enzyme, and the GGPPS enzyme contains the mutation S239C and/or G295D, corresponding to residues within the full-length, wild-type, *Taxus canadensis* GGPPS enzyme, or one or more equivalent mutations in a homologous GGPPS enzyme.

The gene encoding for the terpenoid synthase enzyme and/or the gene encoding for the geranylgeranyl diphosphate synthase (GGPPS) enzyme can be expressed from one or more plasmids and/or can be incorporated into the genome of the cell. In some embodiments, the terpenoid synthase enzyme and/or the geranylgeranyl diphosphate synthase (GGPPS) enzyme is codon-optimized.

Aspects of the invention further include methods for culturing cells associated with the invention to produce a terpenoid. The terpenoids can have one or more cyclic structures. In some embodiments, the terpenoid is a diterpenoid such as levopimaradiene. Methods can further include recovering the terpenoid from the cell culture. In some embodiments, the terpenoid is recovered from the gas phase, while in other embodiments, an organic layer is added to the cell culture, and the terpenoid is recovered from the organic layer. In some embodiments, the cell produces a Taxol, a gibberellin, and/or a steviol glycoside.

Aspects of the invention relate to cells that overexpress one or more components of the non-mevalonate (MEP) pathway, and that recombinantly express a terpenoid synthase enzyme and a geranylgeranyl diphosphate synthase (GGPPS) enzyme. In some embodiments, the cell is a bacterial cell. In certain embodiments, the cell is an *Escherichia coli* cell. In other embodiments, the cell is a Gram-positive cell such as a *Bacillus* cell. In some embodiments, the cell is a yeast cell such as a *Saccharomyces* cell or a *Yarrowia* cell. In other embodiments, the cell is an algal cell or a plant cell.

In some embodiments, the terpenoid synthase enzyme is a diterpenoid synthase enzyme such as a levopimaradiene synthase (LPS) enzyme. In some embodiments, the LPS enzyme is a *Ginkgo biloba* enzyme. In certain embodiments, the LPS enzyme contains one or more mutations. For example, the mutations in the LPS enzyme can be at one or more of the residues selected from the group consisting of: M593, C618, A620, L696, Y700, K723, A729, V731, N838, and I855, corresponding to residues within the full-length, wild-type, *Ginkgo biloba* LPS enzyme, or one or more mutations in equivalent residues within a homologous LPS enzyme. For example, the LPS enzyme can contain one or more mutations selected from the group consisting of: M593I, M593L, C618N, L696Q, K723S, V731L, N838E, I855L, A729G, Y700H, Y700A, Y700C, Y700F, Y700M, Y700W, A620C, A620G, A620S, A620T and A620V, corresponding to mutations at residues within the full-length, wild-type, *Ginkgo biloba* LPS enzyme, or one or more equivalent mutations in a homologous LPS enzyme. In some embodiments, the LPS enzyme contains the mutation M593I and one of the mutations selected from the group consisting of Y700A, Y700C and Y700F, corresponding to mutations at residues within the full-length, wild-type, *Ginkgo biloba* LPS enzyme, or one or more equivalent mutations in a homologous LPS enzyme.

In some embodiments, the GGPPS enzyme is a *Taxus canadensis* enzyme. In certain embodiments, the GGPPS enzyme contains one or more mutations. For example, the GGPPS enzyme can contain a mutation at residue S239 and/or G295, corresponding to residues within the full-length, wild-type, *Taxus canadensis* GGPPS enzyme, or a mutation in one or both equivalent residues within a homologous GGPPS enzyme. In certain embodiments, the GGPPS enzyme contains the mutation S239C and/or G295D, corresponding to mutations at residues within the full-length, wild-type, *Taxus canadensis* GGPPS enzyme, or one or both equivalent mutations in a homologous GGPPS enzyme.

In some embodiments, the LPS enzyme contains the mutation M593I and/or Y700F, corresponding to residues within the full-length wild-type *Ginkgo biloba* LPS enzyme, or one or more equivalent mutations in a homologous LPS enzyme, and the GGPPS enzyme contains the mutation S239C and/or G295D, corresponding to residues within the full-length, wild-type, *Taxus canadensis* GGPPS enzyme, or one or more equivalent mutations in a homologous GGPPS enzyme.

The gene encoding for the terpenoid synthase enzyme and/or the gene encoding for the geranylgeranyl diphosphate synthase (GGPPS) enzyme can be expressed from one or more plasmids and/or can be incorporated into the genome of the cell. In some embodiments, the terpenoid synthase enzyme and/or the geranylgeranyl diphosphate synthase (GGPPS) enzyme is codon optimized.

In some embodiments, cells associated with the invention produce a terpenoid. The terpenoid can have one or more cyclic structures. In certain embodiments, the terpenoid is a diterpenoid such as levopimaradiene. In some embodiments, the cell produces a Taxol, a gibberellin, and/or a steviol glycoside.

Aspects of the invention relate to cells that recombinantly expresses a levopimaradiene synthase (LPS) enzyme, wherein the LPS enzyme contains a mutation at one or more of the residues selected from the group consisting of: M593, C618, A620, L696, Y700, K723, A729, V731, N838, and I855, corresponding to residues within the full-length, wild-type, *Ginkgo biloba* LPS enzyme, or one or more mutations in equivalent residues within a homologous LPS enzyme. In some embodiments, the LPS enzyme contains one or more mutations selected from the group consisting of: M593I, M593L, C618N, L696Q, K723S, V731L, N838E, I855L, A729G, Y700H, Y700A, Y700C, Y700F, Y700M, Y700W, A620C, A620G, A620S, A620T and A620V, corresponding to mutations at residues within the full-length, wild-type, *Ginkgo biloba* LPS enzyme, or one or more equivalent mutations in a homologous LPS enzyme. In certain embodiments, the LPS enzyme contains the mutation M593I and one of the mutations selected from the group consisting of Y700A, Y700C and Y700F, corresponding to mutations at residues within the full-length, wild-type, *Ginkgo biloba* LPS enzyme, or one or more equivalent mutations in a homologous LPS enzyme.

In some embodiments, the cell is a bacterial cell. In certain embodiments, the cell is an *Escherichia coli* cell. In other embodiments, the cell is a Gram-positive cell such as a *Bacillus* cell. In some embodiments, the cell is a yeast cell such as a *Saccharomyces* cell or a *Yarrowia* cell. In other embodiments, the cell is an algal cell or a plant cell. In certain embodiments, the LPS enzyme is codon optimized.

Aspects of the invention relate to cells that recombinantly expresses a geranylgeranyl diphosphate synthase (GGPPS) enzyme, wherein the GGPPS enzyme contains a mutation at residue S239 and/or G295, corresponding to residues within the full-length, wild-type, *Taxus canadensis* GGPPS enzyme, or a mutation in one or both equivalent residues within a homologous GGPPS enzyme. In some embodiments, the GGPPS enzyme contains the mutation S239C and/or G295D, corresponding to mutations at residues within the full-length, wild-type, *Taxus canadensis* GGPPS enzyme, or one or both equivalent mutations in a homologous GGPPS enzyme.

In some embodiments, the cell is a bacterial cell. In certain embodiments, the cell is an *Escherichia coli* cell. In other embodiments, the cell is a Gram-positive cell such as a *Bacillus* cell. In some embodiments, the cell is a yeast cell such as a *Saccharomyces* cell or a *Yarrowia* cell. In other embodiments, the cell is an algal cell or a plant cell. In certain embodiments, the LPS enzyme is codon-optimized. In certain embodiments, the GGPPS enzyme is codon-optimized.

Aspects of the invention relate to isolated levopimaradiene synthase (LPS) polypeptides that contains a mutation at one or more of the residues selected from the group consisting of: M593, C618, A620, L696, Y700, K723, A729, V731, N838, and I855, corresponding to residues within the full-length, wild-type, *Ginkgo biloba* LPS polypeptide (GenBank Accession No. AF331704). For example, the isolated LPS polypeptide can contain one or more mutations selected from the group consisting of: M593I, M593L, C618N, L696Q, K723S, V731L, N838E, I855L, A729G, Y700H, Y700A, Y700C, Y700F, Y700M, Y700W, A620C, A620G, A620S, A620T and A620V. In some embodiments, the isolated LPS polypeptide contains the mutation M593I and one of the mutations selected from the group consisting of Y700A, Y700C and Y700F. In certain embodiments, the isolated LPS polypeptide is codon-optimized. The invention also encompasses isolated nucleic acid molecule encoding any of the LPS polypeptide described herein, recombinant expression vectors comprising such nucleic acid molecules, and libraries including any of the LPS polypeptides or nucleic acid molecules described herein.

Aspects of the invention relate to isolated geranylgeranyl diphosphate synthase (GGPPS) polypeptides, wherein the GGPPS polypeptide contains a mutation at residue S239 and/ or G295, corresponding to residues within the full-length, wild-type, *Taxus canadensis* GGPPS polypeptide (GenBank Accession No. AF081514). In some embodiments, the isolated GGPPS polypeptide contains the mutation S239C and/ or the mutation G295D. In certain embodiments, the isolated GGPPS polypeptide is codon-optimized. The invention also encompasses isolated nucleic acid molecule encoding any of the GGPPS polypeptide described herein, recombinant expression vectors comprising such nucleic acid molecules, and libraries including any of the GGPPS polypeptides or nucleic acid molecules described herein.

These and other aspects of the invention, as well as various embodiments thereof, will become more apparent in reference to the drawings and detailed description of the invention.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 presents schematics of genetic pathways associated with aspects of the invention.

FIG. 2 presents schematics and tables depicting investigation of the putative LPS binding pocket. FIG. 2C presents a summary of LPS mutations and their impact with respect to product distribution and productivity of the engineered pathway. Trace amount (TA), not detected (ND). Numbers indicate percentage of each isomer.

FIG. 4 presents schematics and a graph depicting the generation of a GGPPS library based on stochastic mutation.

FIG. 5 presents graphs depicting the cultivation of an *E. coli* strain overexpressing the MEP pathway and the 'reprogrammed' plant-derived pathway constituting GGPPS S239C/G295D and LPS M593I/Y700F mutants.

FIG. 6 depicts GC-MS chromatograms of diterpenoid products from the engineered *E. coli* strain.

FIG. 7 presents an amino acid sequence alignment of EAS[53] (SEQ ID NO:147) and LPS[54] (SEQ ID NO:2).

DETAILED DESCRIPTION OF THE INVENTION

Figure 1A:
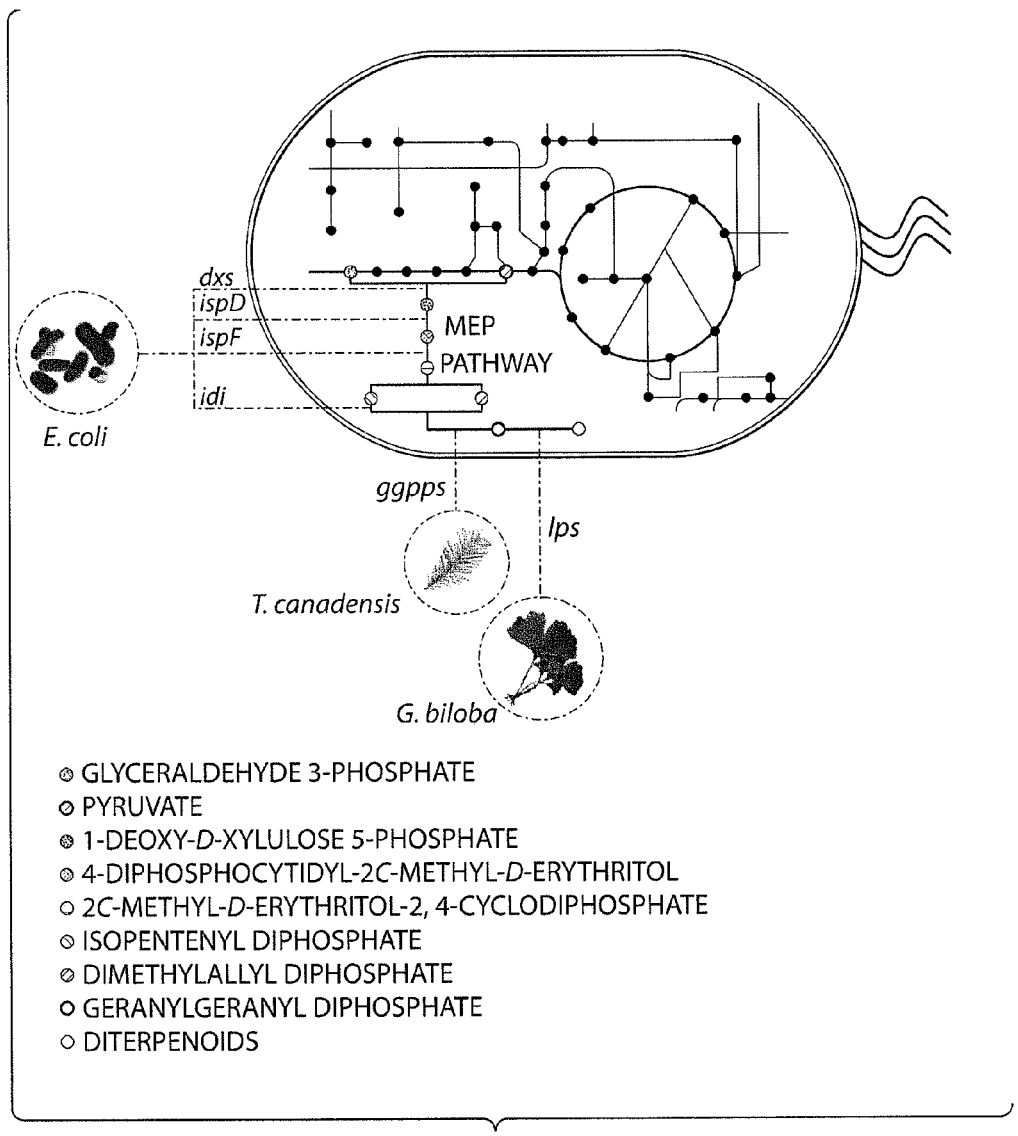
FIG. 1A depicts engineering of levopimaradiene synthesis in *E. coli*. A plant-derived pathway was constructed by introducing *T. canadensis* ggpps and *G. biloba* lps codon optimized genes. To amplify the endogeneous precursor pools of GGPPS substrates (IPP and DMAPP), copy numbers of rate-limiting steps (dxs, ispD, ispF, idi) in the MEP pathway were amplified by additional episomal expression.

Aspects of the invention relate to methods and compositions for the production of one or more terpenoids through recombinant gene expression in cells. Described herein is a novel microbial platform in which a terpenoid synthase enzyme, such as levopimaradiene synthase (LPS) and a geranylgeranyl diphosphate synthase (GGPPS) enzyme are recombinantly expressed in cells. Significantly, mutations in the LPS and GGPPS enzymes have been identified herein that lead to increased production of diterpenoids. This novel microbial platform represents an unexpectedly efficient new system for producing diterpenoids such as levopimaradiene, which has widespread therapeutic applications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing,"

"involving," and variations thereof herein, is meant to encompass the items listed thereafter and equivalents thereof as well as additional items.

Aspects of the invention relate to the production of terpenoids. As used herein, a terpenoid, also referred to as an isoprenoid, is an organic chemical derived from a five-carbon isoprene unit. Several non-limiting examples of terpenoids, classified based on the number of isoprene units that they contain, include: hemiterpenoids (1 isoprene unit), monoterpenoids (2 isoprene units), sesquiterpenoids (3 isoprene units), diterpenoids (4 isoprene units), sesterterpenoids (5 isoprene units), triterpenoids (6 isoprene units), tetraterpenoids (8 isoprene units), and polyterpenoids with a larger number of isoprene units. Terpenoids are synthesized through at least two different metabolic pathways: the mevalonic acid pathway and the MEP (2-C-methyl-D-erythritol 4-phosphate) pathway, also called the MEP/DOXP (2-C-methyl-D-erythritol 4-phosphate/1-deoxy-D-xylulose 5-phosphate) pathway, the non-mevalonate pathway and the mevalonic acid-independent pathway.

Described herein are methods for producing terpenoids, such as diterpenoids, in cells through recombinant gene expression of a terpenoid synthase (also referred to as terpene cyclase) enzyme, and a geranylgeranyl diphosphate synthase (GGPPS) enzyme. In some embodiments, a terpenoid synthase enzyme is a diterpenoid synthase enzyme. Several non-limiting examples of diterpenoid synthase enzymes include casbene synthase[54], taxadiene synthase[55], levopimaradiene synthase[49], abietadiene synthase[52], isopimaradiene synthase[52], ent-copalyl diphosphate synthase[56], syn-stemar-13-ene synthase[56], syn-stemod-13(17)-ene synthase[56], syn-pimara-7,15-diene synthase[56], ent-sandaracopimaradiene synthase[56], ent-cassa-12,15-diene synthase[56], ent-pimara-8 (14), 15-diene synthase[57], ent-kaur-15-ene synthase[57], ent-kaur-16-ene synthase[57], aphidicolan-16β-ol synthase[57], phyllocladan-16α-ol synthase[57], fusicocca-2,10(14)-diene synthase[57] and terpentetriene cyclase[58].

Figure 1B:
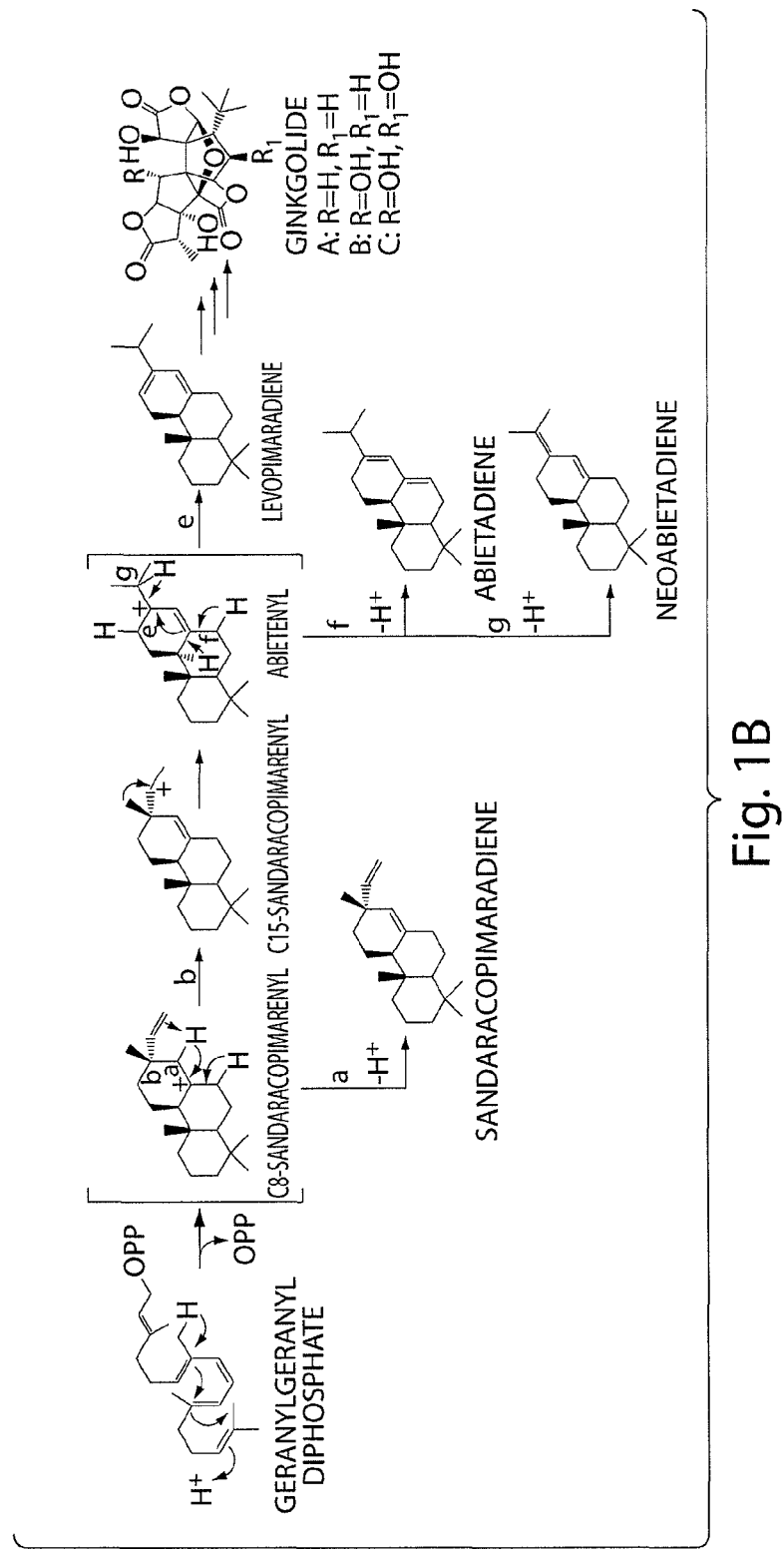
FIG. 1B depicts a general reaction mechanism of "LPS-type" enzymes. Levopimaradiene, the major product of *G. biloba* LPS, is the gateway precursor of ginkgolides. Co-products of LPS include abietadiene, neoabiatadiene, and sandaracopimaradiene that stem from the different deprotonation patterns throughout intermediates in the reaction cascade.

In some embodiments, the diterpenoid synthase enzyme is levopimaradiene synthase[49] (LPS), involved in production of levopimaradiene. In engineered systems described herein, levopimaradiene synthesis can be accompanied by production of one or more other diterpenoids such as abietadiene, sandaracopimaradiene, and neoabietadiene (trace) isomers (FIG. 1b). The GGPPS (geranylgeranyl diphosphate synthase) enzyme belongs to a prenyltransferase type family of enzymes that can accept multiple substrates (DMAPP, geranyl diphosphate (GPP), and farnesyl diphosphate (FPP)[27]). It should be appreciated that methods and compositions described herein can be used to produce a variety of different terpenoids.

According to aspects of the invention, cell(s) that recombinantly express one or more enzymes associated with the invention, and the use of such cells in producing diterpenoids such as levopimaradiene are provided. It should be appreciated that the genes encoding for the enzymes associated with the invention can be obtained from a variety of sources. In some embodiments, the gene encoding for LPS is a plant gene. For example, the gene encoding for LPS can be from a species of Ginkgo, such as Ginkgo biloba (G. biloba). In some embodiments, the gene encoding for GGPPS is a plant gene. For example, the gene encoding for GGPPS can be from a species of Taxus such as Taxus canadensis (T. canadensis). Sequences representing the wild-type DNA and protein for G. biloba LPS are provided by GenBank Accession No. AF331704 (SEQ ID NO:1) and AAS89668 (SEQ ID NO:2) respectively. Sequences representing the wild-type DNA and protein for T. canadensis GGPPS are represented by GenBank Accession No. AF081514 (SEQ ID NO:3) and AAD16018 (SEQ ID NO:4) respectively. It should be appreciated that any of the nucleic acids and/or polypeptides described herein can be codon-optimized and expressed recombinantly in a codon-optimized form. Codon-optimized DNA and protein sequences for T. canadensis GGPPS are provided by SEQ ID NOs:143 and 144 respectively. Codon-optimized DNA and protein sequences for G. biloba LPS are provided by SEQ ID NOs:145 and 146 respectively.

As one of ordinary skill in the art would be aware, homologous genes for these enzymes can be obtained from other species and can be identified by homology searches, for example through a protein BLAST search, available at the National Center for Biotechnology Information (NCBI) internet site. Genes associated with the invention can be cloned, for example by PCR amplification and/or restriction digestion, from DNA from any source of DNA which contains the given gene. In some embodiments, a gene associated with the invention is synthetic. Any means of obtaining a gene encoding for an enzyme associated with the invention is compatible with the instant invention.

Aspects of the invention include strategies to optimize production of a diterpenoid from a cell. Optimized production of a diterpenoid refers to producing a higher amount of a diterpenoid following pursuit of an optimization strategy than would be achieved in the absence of such a strategy. Optimization of production of a diterpenoid can involve modifying a gene encoding for an enzyme before it is recombinantly expressed in a cell. In some embodiments, such a modification involves codon optimization for expression in a bacterial cell. Codon usages for a variety of organisms can be accessed in the Codon Usage Database. Codon optimization, including identification of optimal codons for a variety of organisms, and methods for achieving codon optimization, are familiar to one of ordinary skill in the art, and can be achieved using standard methods.

In some embodiments, modifying a gene encoding for an enzyme before it is recombinantly expressed in a cell involves making one or more mutations in the gene encoding for the enzyme before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the enzyme, such as a substitution or deletion of one or more amino acids.

In some embodiments "rational design" is involved in constructing specific mutations in enzymes. As used herein, "rational design" refers to incorporating knowledge of the enzyme, or related enzymes, such as its three dimensional structure, its active site(s), its substrate(s) and/or the interaction between the enzyme and substrate, into the design of the specific mutation. Based on a rational design approach, mutations can be created in an enzyme which can then be screened for increased production of a diterpenoid.

For example, as described in Example 1, rational design was implemented in creating specific mutations in LPS. Although the crystal structure of LPS is not available, the tertiary folds of other related terpene cyclase enzymes are similar. The structure of one such enzyme, 5-epi-aristolochene synthase[30] (EAS) was used to examine the second active site of LPS. This process of constructing an atomic-resolution model of one protein (e.g., LPS) from its amino acid sequence and a three-dimensional structure of a related homologous protein (e.g., to EAS) is termed "homology modeling". Mutations in the second active site within other terpene cyclases impacts their plasticity[26, 31-33]. In the second active site of an LPS-type enzyme, the bicyclic (+)-copalyl diphosphate (CPP) intermediate (derived from the deprotonation of GGPP in the first active site) undergoes a diphosphate-ionization cyclization. The resulting C8-sandaracopimarenyl cation intermediate is further deprotonated at two alternative sites to release isopimaradiene or sandaracopimaradiene end products. This intermediate can also undergo intramolecular proton transfer and 1,2-methyl migration to yield abietenyl cation. Subsequent deprotonation of abietenyl cation at four possible sites then produce abietadiene, levopimaradiene, neoabietadiene, and palustradiene[28, 29].

Based on the structural data, mutations in LPS were generated in fifteen residues within a 10 Å solvation layer of the LPS model: M593, C618, L619, A620, L696, Y700, K723, A727, A729, V731, N769, E777, N838, G854 and I855 (See FIG. 2a). Amino acid residue numbers indicated herein for LPS are based on amino acid numbers in the full-length, wild-type G. biloba LPS polypeptide (GenBank Accession No. AAS89668). One of ordinary skill in the art would understand, based on protein alignments between G. biloba LPS and LPS from other species, how to determine equivalent residues in other species. It should be appreciated that mutations can also be generated in other residues that are further away from the LPS active site; selection of residues for making such mutations can also be guided by homology modeling. In creating amino acid substitutions within LPS, the sequences of phylogenetically-related enzymes, such as Abies grandis abietadiene synthase (AS), Picea abies abietadiene synthase (AS) and Picea abies isopimardiene synthase (ISO) can be examined and mutations in LPS can be created based, at least in part, on the sequences of these phylogenetically-related enzymes. Non-limiting examples of specific LPS mutations that can be used alone or in combination in methods associated with the invention include: M593I, M593L, M593C, M593S, M593T C618N, L619F, A620T, L696Q, Y700H, Y700F, Y700M, Y700W, K723S, A727S, A729G, V731L, N769A, E777A, N838E, G854T and I855L. It should be appreciated the methods and compositions of the invention also encompass other amino acid substitutions at these fifteen residues, as well as specific substitutions within other residues with proximity to active sites in LPS.

In some embodiments, the LPS enzyme contains a mutation in residue M593, alone or in combination with one or more other mutations. For example, the mutation can be M593I or a substitution with another hydrophobic residue such as leucine (M593L). In certain embodiments, the mutation in M593 can be M593C, M593S or M593T. Based on structural data, Met593 is located at the posterior of the binding pocket of LPS. Without wishing to be bound by any theory, hydrophobic amino acid substitutions at Met593 may improve the diterpenoid yield by disrupting hydrogen bonding at the end of the binding pocket, thus increasing the flexibility of the cavity to better fit the CPP substrate. Additionally, substitutions with large and/or bulky amino acids at Met593 may obstruct the cyclization pocket, reducing diterpenoid yield. Thus, in some embodiments, hydrophobic and/or small residues are preferred for substitution at Met593.

In some embodiments, the LPS enzyme contains a mutation in residue Y700, alone or in combination with one or more other mutations. For example, the mutation can be Y700H, Y700F, Y700M or Y700W. Based on structural data, Y700 is positioned at the entrance of the binding pocket of the enzyme, in close vicinity of a DDXXD magnesium binding motif. Without wishing to be bound by any theory, absence of a hydroxyl group in amino acids that are similar to tyrosine may allow the repositioning of the magnesium closer to the aspartate-rich region, potentially increasing reaction efficiency by improving the chelation of the diphosphate group.

In some embodiments, the LPS enzyme contains a mutation in residue A620, alone or in combination with one or more other mutations. In some embodiments, the mutation involves a substitution with a residue that is small and/or hydrophilic. In certain embodiments, the mutation can be A620C, A620G, A620S or A620T.

The LPS enzyme can contain one mutation or multiple mutations. In some embodiments, the LPS enzyme contains a mutation in M593 and a mutation in Y700. For example, the LPS enzyme can contain the following combinations of mutations: M593I and Y700F, M593I and Y700A, or M593I and Y700C. The LPS enzyme containing these mutations can also contain one or more other mutations.

In some embodiments, random mutagenesis is used for constructing specific mutations in enzymes. As described in Example 1, improved diterpenoid production was achieved in part through random mutagenesis of the GGPPS enzyme and screening for mutations within the enzyme that led to increased diterpenoid production. In some embodiments, the GGPPS enzyme has one or more of the follow mutations: A162V, G140C, L182M, F218Y, D160G, C184S, K367R, A151T, M185I, D264Y, E368D, C184R, L331I, G262V, R365S, A114D, S239C, G295D, I276V, K343N, P183S, I172T, D267G, I149V, T234I, E153D and T259A.

Figure 4A:
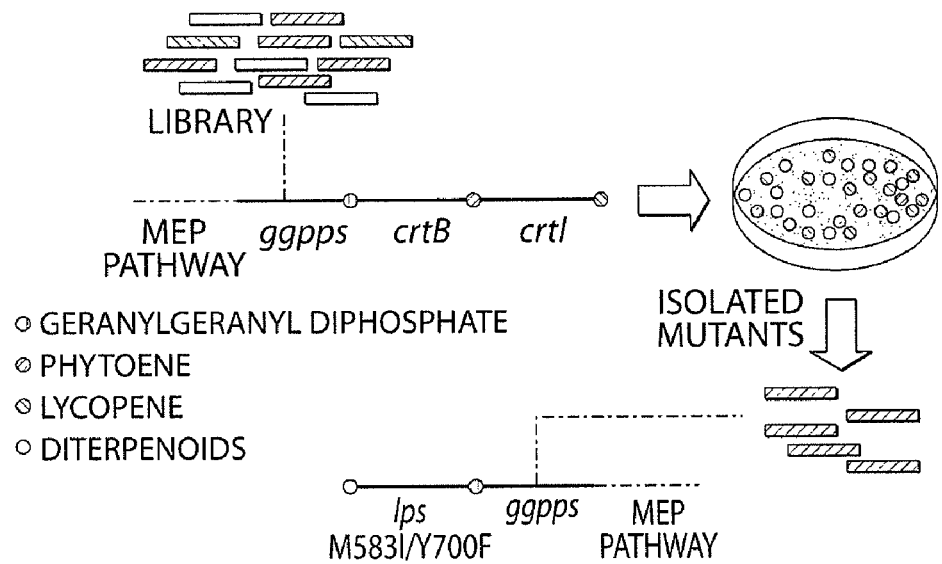
FIG. 4A shows the creation of a facile high-throughput screening assay by fusing a lycopene pathway (crtB and crtI) with ggpps libraries. Mutant ggpps genes that conferred improved lycopene production (red colonies) were isolated. These variants were then co-expressed with lps carrying M593I/Y700F mutations for diterpenoid production assay.
Figure 4B:
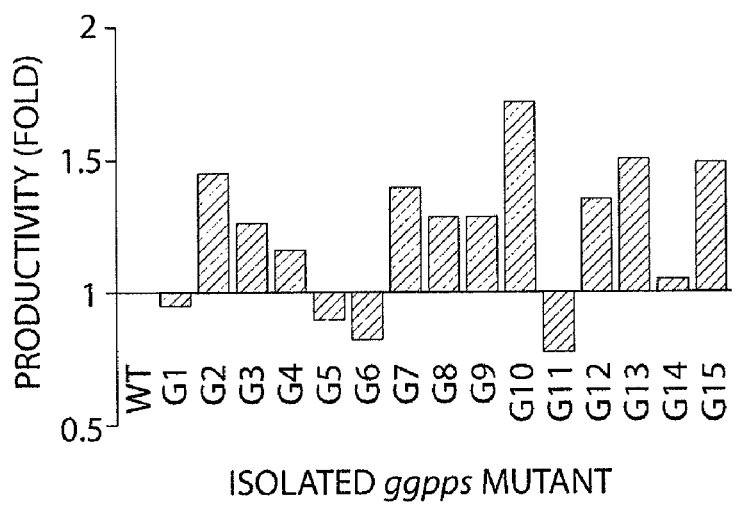
FIG. 4B shows the production phenotype of the pre-engineered *E. coli* strains co-expressing selected ggpps variants and lps M593I/Y700F. WT represents the strain expressing the wild-type ggpps and lps M593I/Y700F.
Figure 4C:
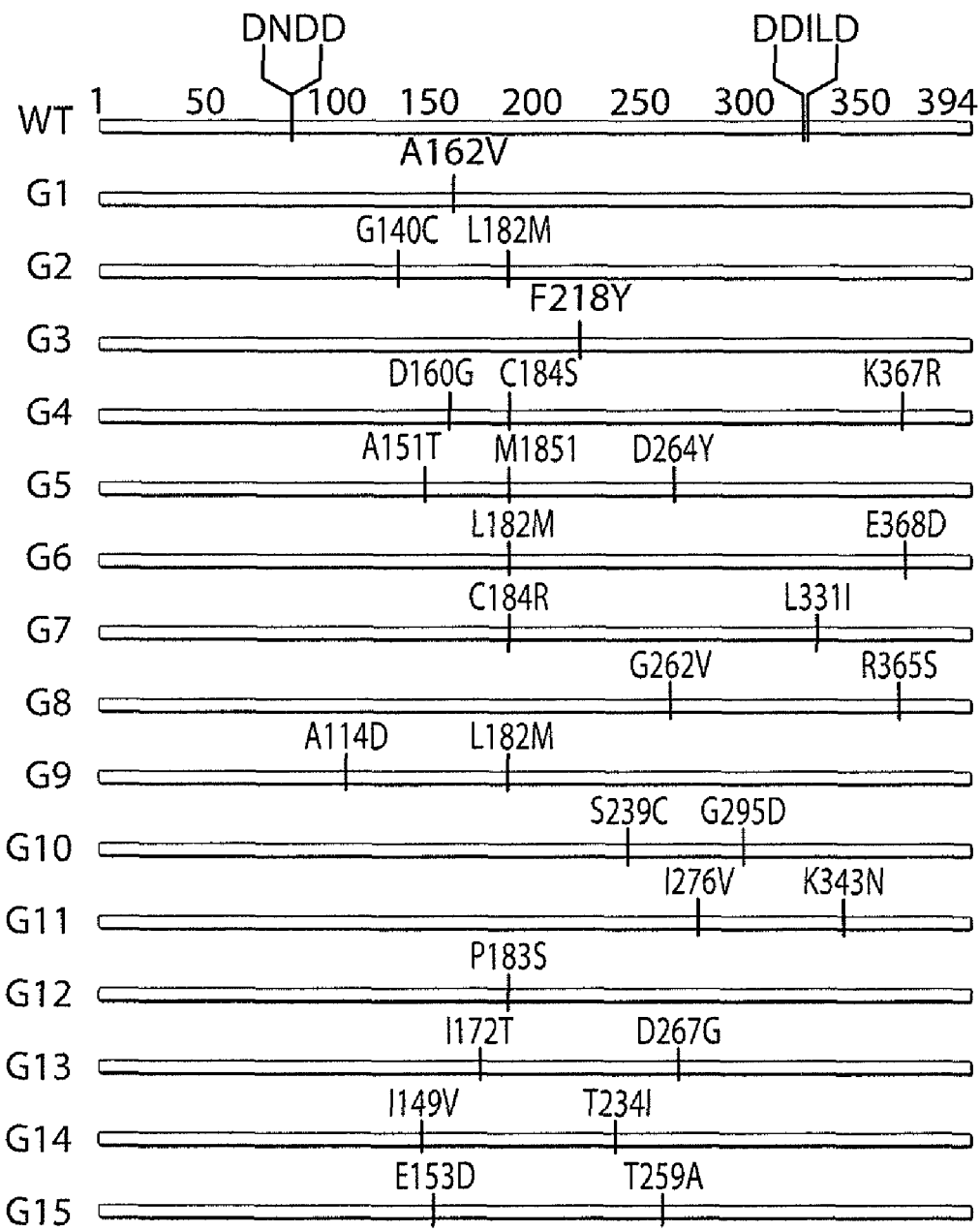
FIG. 4C shows the location and identification of mutations carried by the isolated ggpps variants.

In some embodiments, the GGPPS enzyme has a mutation in residue S239 and/or to residue G295. In certain embodiments, the GGPPS enzyme has the mutation S239C and/or G295D. Mutations in GGPPS that had beneficial effects on diterpenoid production were frequently found to be located between two highly conserved aspartate-rich domains: DDXXXXD and DDXXD (FIG. 4c). A structural analysis of E. coli FPP synthase suggested that the two aspartate-rich regions bind three $Mg^{2+}$ ions to facilitate the anchoring of the diphosphate groups of the IPP and DMAPP substrates[44]. Without wishing to be bound by any theory, due to the close proximity to the aspartate motifs and G295 replacement with aspartate, the S239 and/or G295 mutations may affect GGPPS catalysis by improving the binding efficiency of the magnesium ions needed for substrate anchoring.

Combination of a mutant LPS enzyme and a mutant GGPPS enzyme can be expressed in a cell to provide increased production of diterpenoid. In some embodiments, the cell expresses an LPS enzyme containing the mutations M593I and/or Y700F, and a GGPPS enzyme containing the mutations S239C and/or G295D. It should be appreciated that the choice of mutations will in some instances depend on the desired end product. For example, some mutations or combinations of mutations may be selected because they lead to an overall increase in diterpenoid production, while other mutations or combinations of mutations may be selected because they lead to an increase production of one or more specific diterpenoids, such as levopimaradiene, relative to production of other diterpenoids. For example, a cell expressing an LPS enzyme containing the mutation M593I and either Y700A or Y700C produced a selectivity for levopimaradiene of approximately 97%. A cell expressing both an LPS enzyme containing the mutations M593I and Y700F and a GGPPS enzyme containing the mutations S239C and G295D was found to improve titer of levopimaradiene by approximately 19 fold over wild-type.

In some embodiments, it may be advantageous to use a cell that has been optimized for production of a diterpenoid. For example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. For example, copy numbers of components at rate-limiting steps in the MEP pathway such as (dxs, ispD, ispF, idi) can be amplified, such as by additional episomal expression. In some embodiments, screening for mutations in components of the MEP pathway, or components of other pathways, that lead to enhanced production of a diterpenoid may be conducted through a random mutagenesis screen, or through screening of known mutations. In some embodiments, shotgun cloning of genomic fragments could be used to identify genomic regions that lead to an increase in production of a diterpenoid, through screening cells or organisms that have these fragments for increased production of a diterpenoid. In some cases one or more mutations may be combined in the same cell or organism.

In some embodiments, production of a diterpenoid in a cell can be increased through manipulation of enzymes that act in the same pathway as the enzymes associated with the invention. For example, in some embodiments it may be advantageous to increase expression of an enzyme or other factor that acts upstream of a target enzyme such as an enzyme associated with the invention. This could be achieved by overexpressing the upstream factor using any standard method.

A further strategy for optimization of protein expression is to increase expression levels of one or more genes associated with the invention through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops.

The invention also encompasses isolated LPS and GGPPS polypeptides containing mutations in residues described above, and isolated nucleic acid molecules encoding such polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

Isolated LPS polypeptides can contain mutations in one or more of the following residues: M593, C618, L619, A620, L696, Y700, K723, A727, A729, V731, N769, E777, N838, G854 and I855 (See FIG. 2a). Amino acid residue numbers indicated herein for LPS are based on amino acid numbers in the full-length, wild-type G. biloba LPS polypeptide (GenBank Accession No. AF331704). One of ordinary skill in the art would understand, based on protein alignments between G. biloba LPS and LPS from other species, how to determine equivalent residues in other species. Isolated LPS polypeptides from species other than G. biloba, with mutations in residues that are equivalent to the G. biloba residues described above, are also encompassed by the invention.

Non-limiting examples of isolated G. biloba LPS polypeptides that can be used alone or in combination in methods associated with the invention include isolated LPS polypeptides that contain one or more of the following mutations: M593I, M593L, M593C, M593S, M593T C618N, L619F, A620T, L696Q, Y700H, Y700F, Y700M, Y700W, K723S, A727S, A729G, V731L, N769A, E777A, N838E, G854T and I855L. Isolated LPS polypeptides from species other than G. biloba, with equivalent mutations are also encompassed by the invention.

In some embodiments, the isolated LPS polypeptide contains a mutation in residue M593, alone or in combination with one or more other mutations. For example, the mutation can be M593I or a substitution with another hydrophobic residue such as leucine (M593L). In certain embodiments, the mutation in M593 can be M593C, M593S or M593T. In some embodiments, the isolated LPS polypeptide contains a mutation in residue Y700, alone or in combination with one or more other mutations. For example, the mutation can be Y700H, Y700F, Y700M or Y700W. In some embodiments, the isolated LPS polypeptide contains a mutation in residue A620, alone or in combination with one or more other mutations. In some embodiments, the mutation involves a substitution with a residue that is small and/or hydrophilic. In certain embodiments, the mutation can be A620C, A620G, A620S or A620T. The isolated LPS polypeptide can contain one mutation or multiple mutations. In some embodiments, the isolated LPS polypeptide contains a mutation in M593 and a mutation in Y700. For example the isolated LPS polypeptide can contain the following combinations of mutations: M593I and Y700F, M593I and Y700A, or M593I and Y700C. The isolated LPS polypeptide containing these mutations can also contain one or more other mutations.

Isolated GGPPS polypeptides can contain mutations in one or more of the following residues: A162, G140, L182, F218, D160, C184, K367, A151, M185, D264, E368, C184, L331, G262, R365, A114, S239, G295, I276, K343, P183, I172, D267, I149, T234, E153 and T259. Amino acid residue numbers indicated herein for GGPPS are based on amino acid numbers in the full-length, wild-type T. canadensis GGPPS polypeptide (GenBank Accession No. AF081514). One of ordinary skill in the art would understand, based on protein alignments between T. canadensis GGPPS and GGPPS from other species, how to determine equivalent residues in other species. Isolated GGPPS polypeptides from species other than T. canadensis, with mutations in residues that are equivalent to the T. canadensis residues described above, are also encompassed by the invention.

Non-limiting examples of isolated T. canadensis GGPPS polypeptides that can be used alone or in combination in methods associated with the invention include isolated GGPPS polypeptides that contain one or more of the following mutations: A162V, G140C, L182M, F218Y, D160G, C184S, K367R, A151T, M185I, D264Y, E368D, C184R, L331I, G262V, R365S, A114D, S239C, G295D, I276V, K343P, P183S, I172T, D267G, I149V, T234I, E153D and T259A. Isolated GGPPS polypeptides from species other than T. canadensis, with equivalent mutations are also encompassed by the invention.

In some embodiments, the isolated GGPPS polypeptide contains a mutation in residue S239 and/or residue G295. In certain embodiments, the isolated GGPPS polypeptide has the mutation S239C and/or G295D. The isolated LPS polypeptide containing these mutations can also contain one or more other mutations.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell. It should be appreciated that some cells compatible with the invention may express an endogenous copy of one or more of the genes associated with the invention as well as a recombinant copy. In some embodiments, if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of a terpenoid, such as a diterpenoid.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of a terpenoid, such as a diterpenoid, is demonstrated in Example 1 using *E. coli*. The novel method for producing diterpenoids can also be expressed in other bacterial cells, fungi (including yeast cells), plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of terpenoids, such as diterpenoids. In some embodiments the concentration and amount of a supplemental component may be optimized. In some embodiments, how often the media is supplemented with one or more supplemental components, and the amount of time that the media is cultured before harvesting a terpenoid, such as a diterpenoid, is optimized.

According to aspects of the invention, high titers of a diterpenoid such as levopimaradiene, are produced through the recombinant expression of genes associated with the invention, in a cell. As used herein "high titer" refers to a titer in the milligrams per liter (mg $L^{-1}$) scale. The titer produced for a given product will be influenced by multiple factors including choice of media. In some embodiments the total diterpenoid titer is at least 10 mg $L^{-1}$. For example the titer may be 10, 20, 50, 75, 100, 125, 150, 175, 200, 225, 250, 275, 300, 350, 400, 450, 500, 550, 600, 650, 700, 750, 800, 850, 900 or more than 900 mg $L^{-1}$ including any intermediate values. In some embodiments, a cell that expresses an LPS enzyme containing the mutations M593I and Y700F, and a GGPPS enzyme containing the mutations S239C and G295D can produce a total diterpenoid titer of approximately 800 mg $L^{-1}$ in approximately 168 hours.

The liquid cultures used to grow cells associated with the invention can be housed in any of the culture vessels known and used in the art. In some embodiments large scale production in an aerated reaction vessel such as a stirred tank reactor can be used to produce large quantities of terpenoids, such as diterpenoids, that can be recovered from the cell culture. In some embodiments, the terpenoid is recovered from the gas phase of the cell culture, for example by adding an organic layer such as dodecane to the cell culture and recovering the terpenoid from the organic layer.

Diterpenoids, such as levopimaradiene, produced through methods described herein have widespread applications. Levopimaradiene is a key diterpenoid precursor of ginkgolides which can be administered for a variety of therapeutic purposes including improving vascular function, inhibiting thrombosis and embolism, neuroprotective functions, and cancer treatment. Terpenoid pathways also lead to compounds used in flavors, cosmetics, and biofuels. Furthermore, methods described herein to search for mutations in LPS can be applied to other diterpenoid synthases such as taxadiene synthase. GGPPS mutations described herein can also be applied to synthesis of precursors for other plant diterpenoids including cancer therapeutics such as Taxol, plant growth hormones such as gibberellins and food products such as the natural sweetener steviol glycoside.

EXAMPLES

Example 1

Harnessing the Evolvability of a Terpenoid Biosynthetic Pathway for Overproduction and Selectivity Control Introduction The engineering of secondary metabolite biosynthesis in heterologous microorganisms is a promising approach to produce drug precursors in a scalable manner. However, secondary metabolite pathways are typically low-yielding and produce side products. Herein, these limitations were addressed by harnessing the evolvability of a plant-derived terpenoid pathway to efficiently synthesize levopimaradiene, the gateway precursor of the bioactive ginkgolides. Variants of geranylgeranyl diphosphate synthase and levopimaradiene synthase were created to uncover mutations that confer divergent phenotypes in *Escherichia coli*. Sequence space explorations by random and rational mutagenesis identified combinations of mutations that increased levopimaradiene synthesis up to 19-fold over the wild-type pathway, and reduced the abietadiene and sandaracopimaradiene isomers. In bench-scale controlled culture conditions, strains harboring the highest-producing pathway variant resulted in ~700 mg/L levopimaradiene. This pathway reprogramming framework should expedite engineered biosynthesis applications for large-scale pharmaceutical production, and facilitate the overproduction of other chemicals hitherto only derived from natural resources.

Results

Probing the LPS Putative Binding Pocket by Phylogenetic-Based Mutations

Figure 6A:
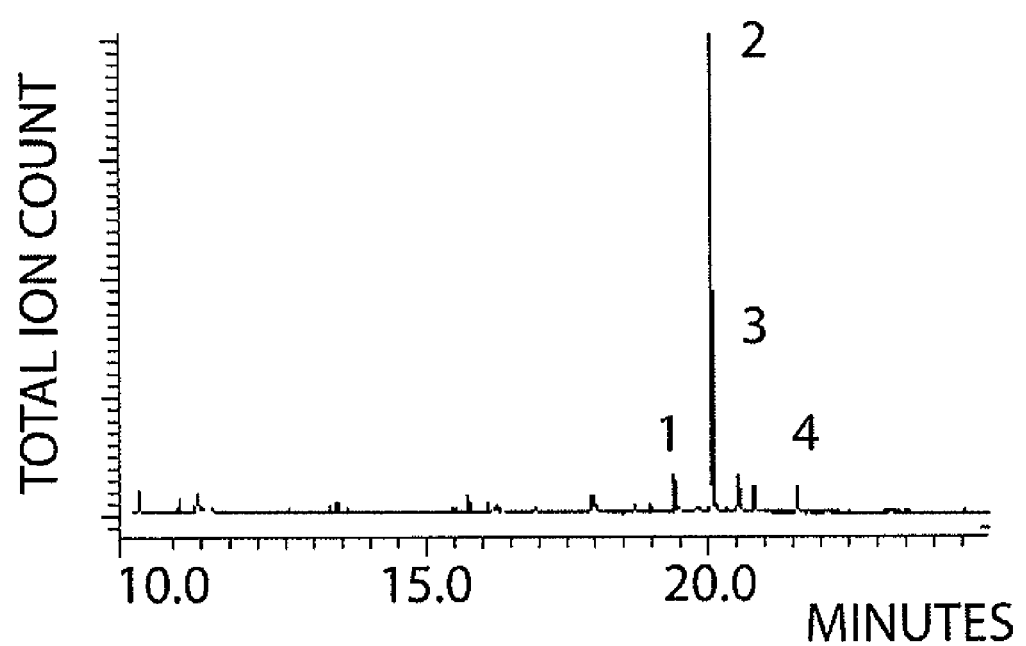
FIG. 6A shows total ion chromatogram and retention time of the diterpenoids secreted in the culture media used to cultivate the pre-engineered *E. coli* strain expressing the wild type GGPPS and LPS.
Figure 6B:
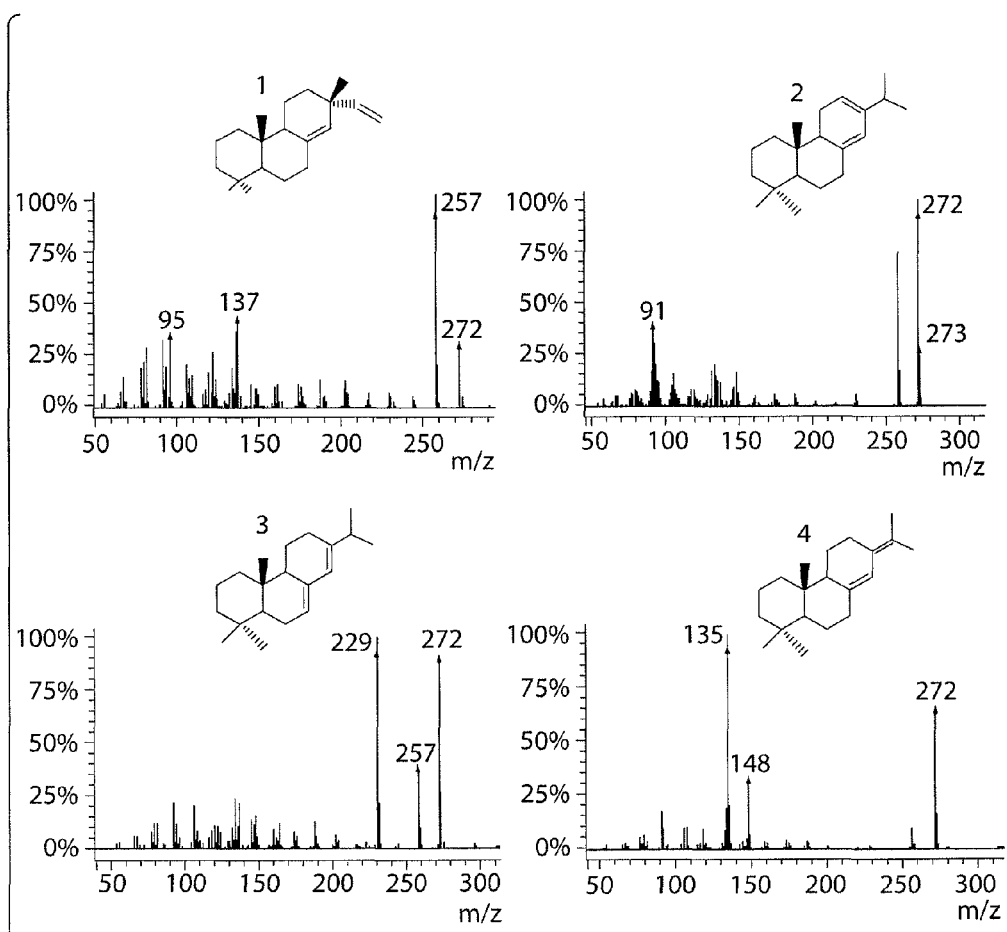
FIG. 6B shows GC-MS spectra of the product peaks corresponding to sandaracopimaradiene (1), levopimaradiene (2), abietadiene (3), and neoabietadiene (4) as previously reported in the literature[51,52].

The simultaneous expression of the wild-type GGPPS and LPS in a pre-engineered *E. coli* strain overexpressing the MEP pathway resulted in the production of ~27 mg/L diterpenoid mixture in a 2-mL culture. In this product mixture, levopimaradiene (87%) was accompanied by abietadiene (11%), sandaracopimaradiene (2%), and neoabietadiene (trace amounts), as identified by gas chromatography-mass spectroscopy (GC-MS) (FIG. 1b, FIG. 6b). This wild-type phenotype provided the baseline comparison used in the selection of evolved pathway variants. The principal challenge in exploring the evolvability of LPS through the generation of large mutant libraries is the lack of a suitable high-throughput screen. Therefore, a structure-guided method was implemented herein to allow the identification of tunable residues within LPS. The crystal structure of LPS is currently not available. However, because the tertiary folds of terpene cyclases are similar, the only available structure of one such enzyme, that of 5-epi-aristolochene synthase[30] (EAS), was used to thread the putative second active site of LPS.

The second active site was focused on because mutations in this site within other terpene cylases impacted their 'plasticity'[26, 31-33]. In the second active site of an "LPS-type" enzyme, the bicyclic (+)-copalyl diphosphate (CPP) intermediate (derived from the deprotonation of GGPP in the first active site) undergoes a diphosphate-ionization cyclization. The resulting C8-sandaracopimarenyl cation intermediate is further deprotonated at two alternative sites to release isopimaradiene or sandaracopimaradiene end products. However, this intermediate can also undergo intramolecular proton transfer and 1,2-methyl migration to yield abietenyl cation. Subsequent deprotonation of abietenyl cation at four possible sites then produce abietadiene, levopimaradiene, neoabietadiene, and palustradiene[28,29].

Figures 2A, 2B:
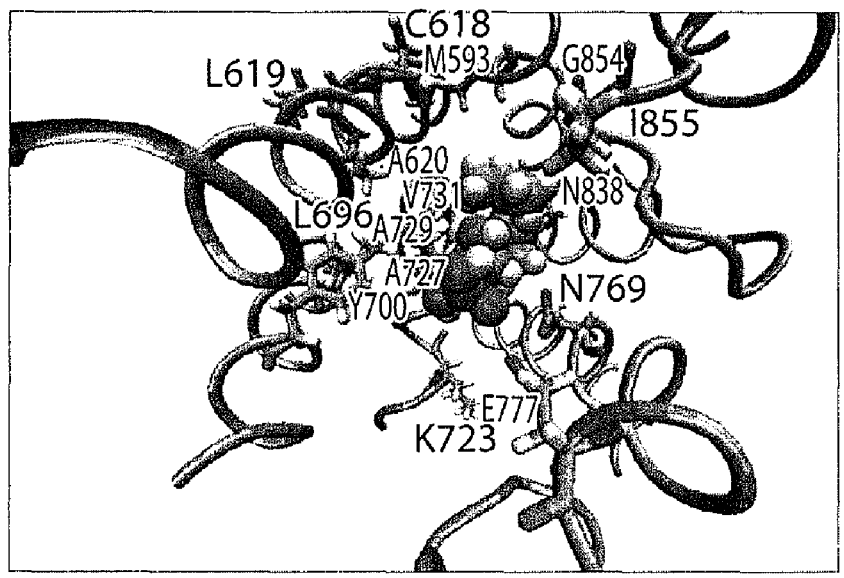
FIG. 2A shows the homology structural model for LPS second active site. Fifteen residues within 10 Å, which were targeted for phylogenetic-based mutational analysis, are shown. The substrate in the binding pocket is farnesyl hydroxyphosphonate.
FIG. 2B shows a comparison of selected residues in *G. biloba* LPS (GbLPS) with those in *A. grandis* and *P. abies* abietadiene synthase (AbAS and PaAS), and *P. abies* isopimaradiene synthase (PaISO). Residues in GbLPS that are also found in any one of the paralogous enzymes are indicated.

To allow sufficient sampling of the three dimensional space, fifteen residues within the 10 Å solvation layer of the LPS model were probed (FIG. 2a). Although residues far from the binding pocket may contribute to enzyme evolvability, consideration of these residues increases the library size to a degree that is experimentally intractable. Amino acid substitutions within related enzymes (phylogenetically-based mutation)[26, 34] were used to perturb the selected fifteen residues of LPS. These residues were replaced with those derived from paralogous "LPS-type" enzymes that are functionally different from LPS (FIG. 2b), namely *Abies grandis* abietadiene synthase (AS), *Picea abies* AS, and *P. abies* isopimardiene synthase (ISO). In AS, abietadiene, levopimaradiene, and neoabietadiene are synthesized in almost equal proportion[32]. On the other hand, ISO produces only isopimaradiene[31]. Mutations of M593I, C618N, L619F, A620T, L696Q, K723S, A729G, N838E, G854T, and I855L were created based on residues in *A. grandis* and *P. abies* AS, whereas Y700H, A727S and V731L were created based on *P. abies* ISO. Alanine was used to replace Asn769 and Glu777 because these amino acids are conserved throughout LPS, AS, and ISO (FIG. 2c).

The pre-engineered *E. coli* expressing the wild-type GGPPS provided an in vivo screening system for titer and product distribution changes by the LPS mutations. The profiles of diterpenoid product distribution resulting from expressing LPS mutants M593I, C618N, L619F, A620T, L696Q, K723S, V731L, N838E, G854T, and I855L were observed to be similar to expression of wild type LPS (FIG. 2c). Hence, with respect to LPS product selectivity, these mutations were rendered neutral or close to neutral. Diterpenoid productivities resulting from expressing LPS mutants L619F, A620T and G854T were also not significantly changed compared to wild-type LPS (within 50%). However, diterpenoid production levels were notably altered by expressing mutants M593I, C618N, L696Q, K723S, V731L, N838E, and I855L (FIG. 2c). The highest total diterpenoid production increase (~3.7-fold) was mediated by expressing LPS M593I. In all cases, expression of these mutants did not significantly affect product distribution. Expression of LPS mutant Y700H, however, resulted in a significant alteration of diterpenoid product distribution by abolishing abietadiene synthesis and increasing sandaracopimaradiene proportion (FIG. 2c). Although a single mutation in *P. abies* AS, corresponding to Tyr700, did not result in product selectivity changes in vitro, it promoted product selectivity shift when combined with other mutations[31]; hence Tyr700 may play an important role in mediating the evolvability of "LPS-type" enzymes. Additionally, the expression of the A729G mutant resulted in the exclusive production of sandaracopimaradiene; however, it was concomitant with a reduction of productivity by ~98% (FIG. 2). Finally, diterpenoid production was not observed in systems expressing LPS A727S, N769A, and E777A variants. These residues fell within ~4.7 Å from substrate in the homology model; therefore, it was not surprising that the mutations were deleterious to LPS activity given the close proximity to the substrate.

Mutational Enrichment of Tunable LPS Residues

The previous results pointed to mutations in LPS that significantly affected production phenotype, namely M593I and Y700H. Although the preliminary mutation of Ala729 imparted product selectivity changes, it was excluded from further analysis because even a conservative replacement such as glycine was deleterious. From analyzing the structural model, Met593 was observed to be located at the posterior of the binding pocket, whereas Tyr700 is positioned at the entrance (in close vicinity of the DDXXD magnesium binding motif). To obtain the complete LPS evolvability profile by these residues, all amino acids were sampled through saturation mutagenesis. Additionally, the effects of expressing the saturation mutagenesis library of Ala620 was explored because a mutation at this position in *A. grandis* AS changed its product selectivity in vitro[32].

Figure 3A:
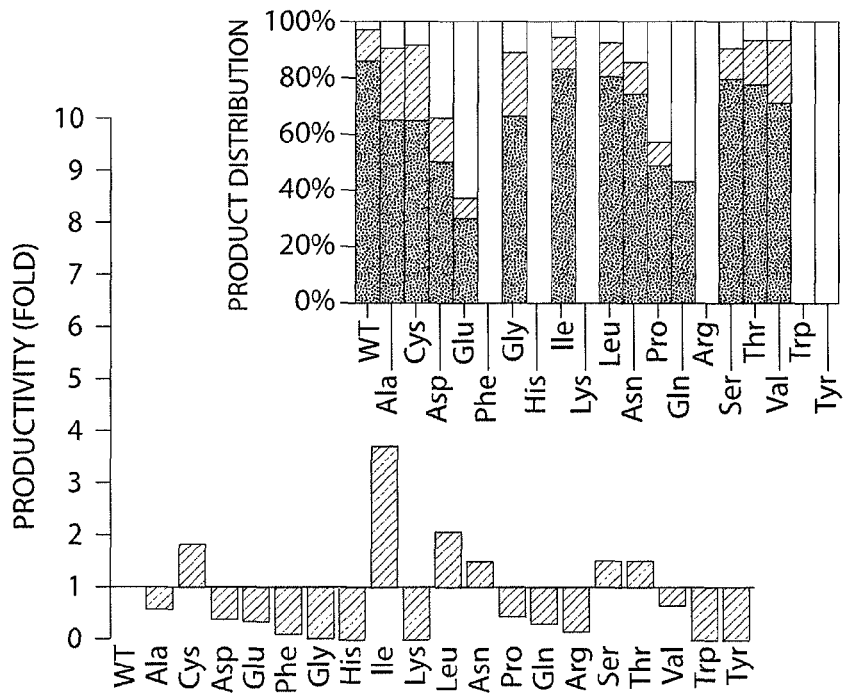
FIG. 3 presents graphs depicting characteristics (productivity and product distribution) of the pre-engineered strains expressing wild-type ggpps and lps saturation mutagenesis library of: Met593 (FIG. 3A), Tyr700 (FIG. 3B), Ala620 (FIG. 3C), and Tyr700 (FIG. 3D) using lps M593I. In the product distribution charts, dark gray bars, light gray bars, and white bars represent proportions of levopimaradiene, abietadiene, and sandaracopimaradiene, respectively in the product mixture. Two toned (white and very light gray) bars represent nil production. WT represents the pre-engineered strain expressing wild type ggpps and lps.

From the saturation mutagenesis library of Met593, two substitutions were found that conferred significant productivity improvement (FIG. 3a). In addition to isoleucine which was discovered in the phylogenetic-based mutation, the replacement with another hydrophobic residue similar in size as methionine, i.e. leucine, increased diterpenoid productivity by ~2-fold without significantly changing product distribution (FIG. 3a). Based on the structural significance of this position, this productivity improvement appeared to be caused by the disruption of H-bonding at the end of the binding pocket, thus increasing the flexibility of the cavity to better fit the CPP substrate. Therefore, the M593I mutation likely resulted in the highest production increase (~3.7-fold) because isoleucine is the most hydrophobic amino acid[35]. Substitutions with much smaller residues than methionine only yielded moderate production improvement (less than 2-fold in the case of cysteine, serine, and threonine), and were disruptive in the case of alanine, glycine, and valine. Furthermore, substitutions with amino acids longer than five heavy atoms and those with bulky rings such as phenylalanine, tyrosine, and tryptophan also consistently decreased or abolished activity. These trends are consistent with the requirement for the substrate to have an unobstructed cyclization pocket, as the center of the bend is proximal to this residue. Moreover, replacements with hydrophilic amino acids[36] such as aspartic acid, glutamic acid, lysine, and arginine also generally reduced productivity because their ability to form their own H-bonding may reduce the capacity of the binding pocket.

Figure 3B:
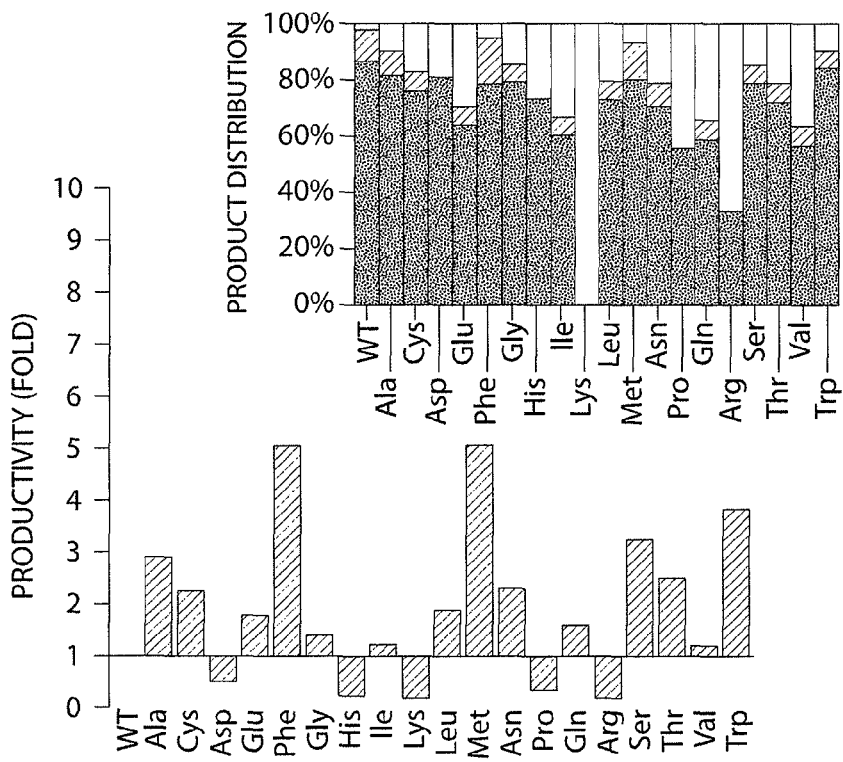

The replacement of Tyr700 with phenylalanine, methionine, and tryptophan improved to productivity up- to ~5-fold (FIG. 3b). The reaction cascade toward the formation of abietenyl cation requires an energetically unfavorable transition from a tertiary to a secondary carbocation[29]. Therefore, it was postulated that the latter species is stabilized by the ionic interaction with the paired diphosphate anion that is chelated by the magnesium ion[32]. Tyr700 is located within close proximity to the magnesium binding site, thus the absence of the hydroxyl group in amino acids that are similar to tyrosine may allow the repositioning of the magnesium closer to the aspartate-rich region; hence, increasing reaction efficiency by improving the chelation of the diphosphate group. A few mutations, i.e. replacements with aspartic acid, histidine, proline, arginine, and lysine, abolished abietadiene synthesis in the product mixture, and conferred a decrease in productivity (FIG. 3b). The replacement with positively charged residues or a helix breaker (proline) might cause a misalignment of the diphosphate anion that impaired catalysis or prevented the deprotonation of abietenyl cation at carbon position f (FIG. 1b) to create abietadiene.

Figure 3C:
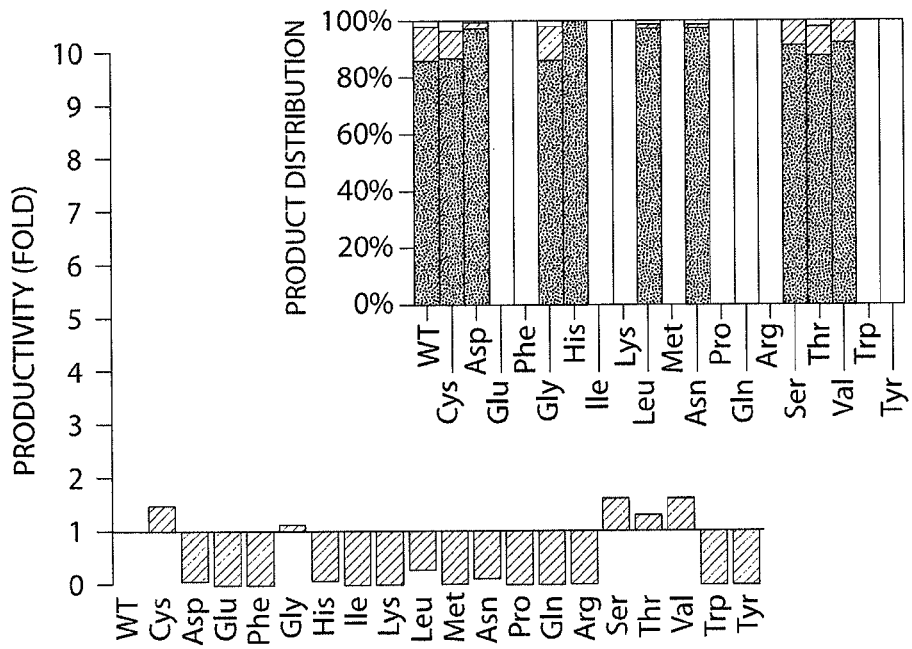

Finally, the sampling of all amino acid substitutions of Ala620 revealed that only replacement with residues similar to alanine (small or hydrophilic) (cysteine, glycine, serine, and threonine) as well as valine retained LPS activity; whereas other substitutions were destructive or deleterious (FIG. 3c). A few destructive mutations (replacements with aspartic acid, leucine, asparagine) also destabilized abietenyl deprotonation to yield abietadiene. Therefore, Ala620 in LPS did not appear to control product selectivity and productivity in LPS, yet it was important for catalysis.

Combinatorial LPS Mutations

Figure 3D:
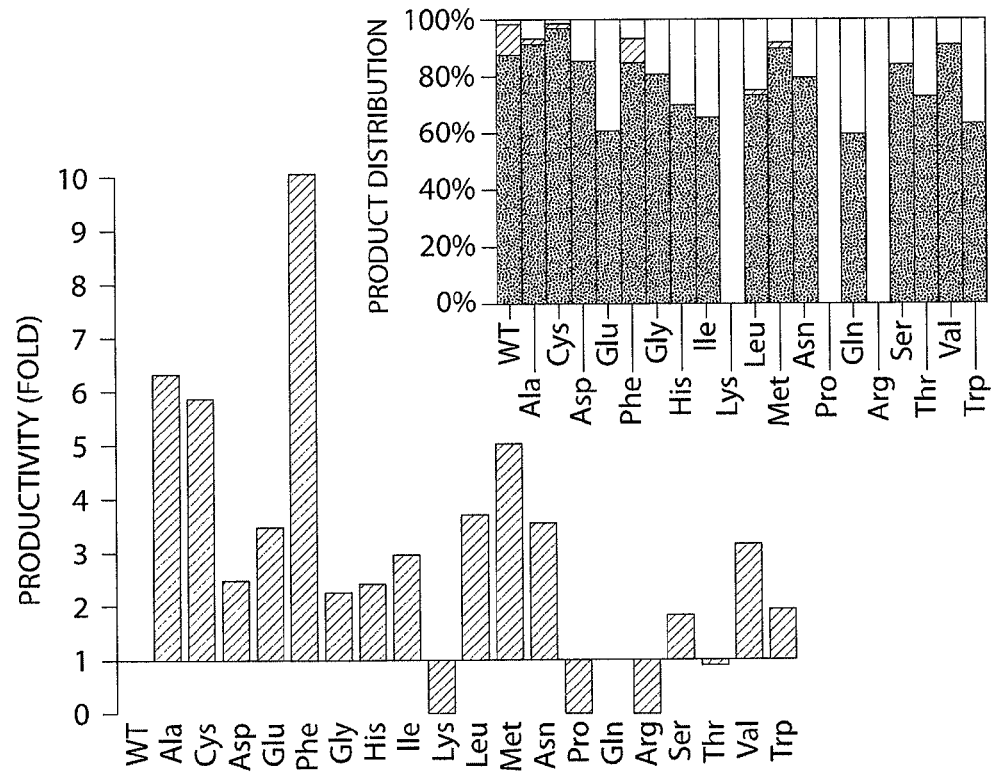

In laboratory experiments, the beneficial effect of single mutations are often additive[33, 37, 38]. Therefore, the production improvement resulting from expressing the LPS M593I variant encouraged investigation of the effect of this beneficial mutation in combination with saturation mutagenesis of Tyr700. As shown in FIG. 3d, this combination successfully integrated the advantageous properties of the individual mutations, resulting in one variant (M593I/Y700F) that increased diterpenoid titer by 10-fold over the expression of the wild-type enzyme without significant changes in product distribution. Interestingly, the expression of most LPS variants carrying the double mutations resulted in the reduction of abietadiene proportion (FIG. 3d). In two variants, M593I/Y700A and M593I/Y700C, the reduction of abietadiene was complemented by an increase in levopimaradiene, resulting in mixtures that contained up to 97% levopimaradiene. The combinations of M593I with to Y700A and Y700C also conferred productivity improvement by ~6.3- and ~5.8-fold, respectively. Thus, it appeared that these mutations facilitated the stabilization of the intermediates that led to favoring abietenyl intermediate formation yet prevented proton extraction from route f (FIG. 1b). It is noteworthy that using the M593I mutant LPS as a parent for the subsequent saturation-mutagenesis only conferred three variants that decreased or abolished diterpenoid productivity (FIG. 3d). In contrast, previous saturation mutagenesis of Tyr700 resulted in five pathway variants that decreased/abolished diterpenoid production (FIG. 3b). Although a single M593I mutation was rendered neutral with respect to product selectivity, this mutation restored LPS activity upon subsequent defective mutations by aspartic acid and histidine replacement at residue 700. Thus M593I appeared to facilitate subsequent mutational robustness, a paradigm of neutral genetic drift[39].

Random Mutagenesis of GGPPS

The generation of a high-producing pathway was extended by the creation of a GGPPS library. As an up-stream enzyme of LPS, GGPPS catalyzes the formation of the linear polyprenyl ($C_{20}$) diphosphate starter unit by the sequential elongation of IPP with the allylic monomer. Concomitant with diterpenoid production increase, methyl jasmonate elicitation in Taxus cell culture elevated GGPPS expression level together with the respective downstream cyclase[40]. These results suggested that together with the cyclase, GGPPS is an important target in the diterpenoid pathway for increasing productivity. To optimize levopimaradiene production, T. canadensis GGPPS was incorporated into the pathway assembly because this enzyme has high specificity toward FPP to synthesize GGPP.

Although the structural information of a plant GGPPS from an angiosperm origin is available[41], the crystal structure for a gymnosperm GGPPS has not been solved. Furthermore, the folding similarity of gymnosperm GGPPS enzymes and their angiosperm analogs are not known. Despite catalyzing essentially the same enzymatic reaction, GGPPS enzymes are known to exhibit wide structural diversity among organisms[41]. Therefore, based on secondary structure analysis[42], the notable division of gymnosperm from angiosperm GGPPS enzymes may imply significant tertiary fold differences. The lack of a suitable structural guide prompted us to devise a stochastic mutational approach to evolve T. canadensis GGPPS. To enable a facile high-throughput screening method for isolating improved GGPPS variants, we utilized a lycopene biosynthetic pathway consisting of crtB and crtI as a colorimetric reporter (FIG. 4a). In this system, the expression of wild-type GGPPS resulted in colonies with orange coloration. Improved GGPPS variants from the mutagenesis were identified by the improvement of lycopene production in the cell, as determined by red coloration. Fifteen ggpps variants were isolated from colonies exhibiting red coloration. To assess the potential for improving levopimaradiene production in vivo, the fifteen mutant GGPPS isolates were co-expressed with the high-producing LPS M593I/Y700F mutant in the pre-engineered E. coli strain. Five GGPPS variants did not confer a levopimaradiene increase indicating false positives obtained from the colorimetric screening. However, the co-expression of ten GGPPS mutants resulted in diterpenoid production improvement (FIG. 4b.). The expression of mutant G10 resulted in the highest diterpenoid production increase (~1.7-fold) over the pathway harboring the wild-type GGPPS and the LPS M593I/Y700F, representing a ~20-fold total increase (~19-fold levopimaradiene increase) over the pathway harboring wild-type GGPPS and LPS (FIG. 4b, Table 6).

Sequence analysis of G10 revealed that two positions were mutated, namely S239C and G295D (FIG. 4c). Amino acid alignment with GGPPS sequences from other plants[43] showed that most beneficial mutations are located in the region in between the two highly conserved aspartate-rich DDXXXXD and DDXXD domains (FIG. 4c). A structural analysis of E. coli FPP synthase suggested that the two aspartate-rich regions bound three $Mg^{2+}$ ions to facilitate the anchoring of the diphosphate groups of the IPP and DMAPP substrates[44]. Therefore due to the close proximity to the aspartate motifs and Gly295 replacement with aspartate, the mutations in G10 may affect GGPPS catalysis by improving the binding efficiency of the magnesium ions needed for substrate anchoring.

Levopimaradiene Overproduction in Controlled Culture Conditions

Figure 5A:
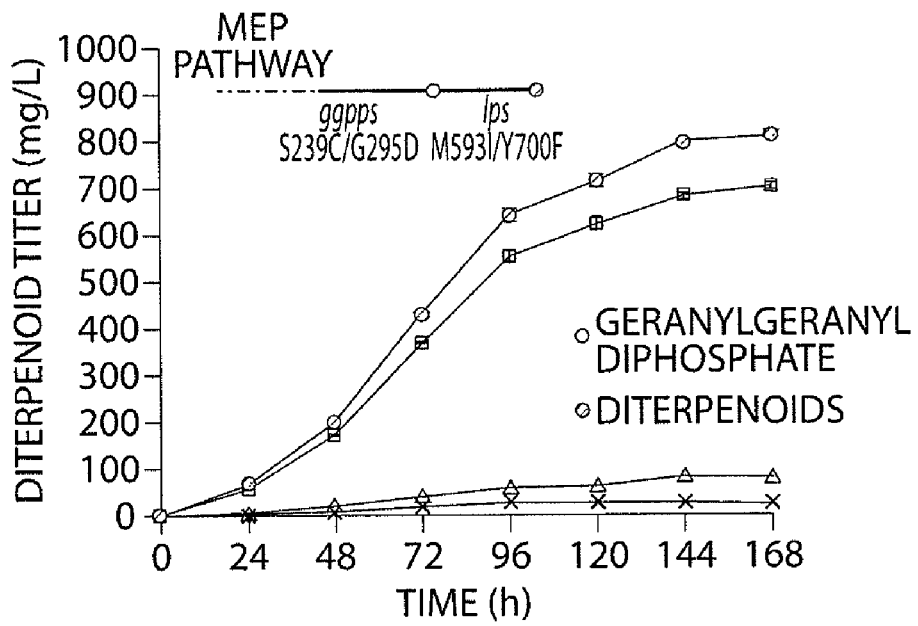
FIG. 5A presents diterpenoid production curves. Total diterpenoid, levopimaradiene, abietadiene, and sandaracopimaradiene are in circles, squares, triangles, and crosses, respectively.
Figure 5B:
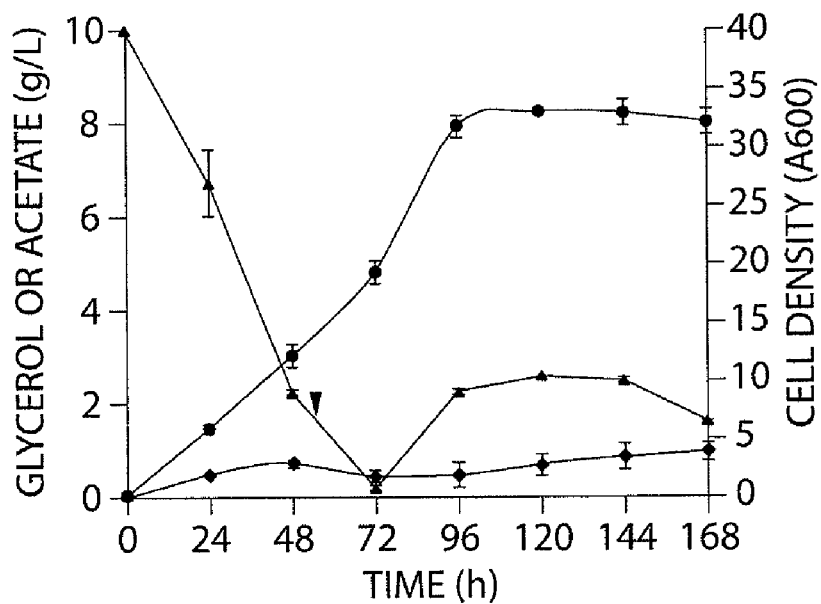
FIG. 5B depicts feed, fermentative by-product, and biomass curves. Glycerol, acetate, and cell density are in triangles, diamonds, and circles, respectively. Inverse triangle denotes the time point where 3 g of glycerol was added every 8 h.

The performance of the pre-engineered E. coli strain expressing the highest-producing levopimaradiene pathway (consisting of GGPPS S239C/G295D and LPS M593I/Y700F) was assessed in small bioreactors (1 L) under controlled conditions. The total diterpenoid titer reached a maximum of ~800 mg/L in 168 h, and levopimaradiene constituted ~700 mg/L of total diterpenoids (FIG. 5a). Using this engineered strain, 10 g/L glycerol was almost depleted after 56 h. Therefore 3 g/L glycerol was added to the culture every 8 h after this time point (FIG. 5b). Despite the relatively rapid consumption of glycerol, acetate only accumulated below 1 g/L throughout the cultivation. This suggested a significant diversion of flux from acetyl-CoA (acetate precursor) because the up-stream precursors, pyruvate and glyceraldehyde 3-phosphate were efficiently channeled by the engineered pathway for synthesizing the diterpenoid products. Overall, this experiment demonstrated that the production improvement obtained from the new pathway translated well toward a larger cultivation.

Discussion

Herein, a combination of rational and random mutational searches were used to uncover cryptic genetic variations in an engineered plant pathway that imparted levopimaradiene production changes in E. coli. Overall, the identification of as few as one to two mutations of LPS and GGPPS to generate changes in diterpenoid production or product distribution highlights the susceptibility of promiscuous secondary metabolic enzymes to new functions. Structure-guided analysis followed by saturation mutagenesis revealed several mutations in LPS that conferred diterpenoid production improvements and product selectivity changes. Notably, when M593I and Y700F mutations were combined, an additional ~6.5-fold production increase was achieved over the M593I mutation alone (FIG. 3a, 3d, and Tables 2 and 5). This result presents another example of the additivity of beneficial mutations found in laboratory evolution[33, 37, 38]. Furthermore, the combination of M593I either with Y700A or Y700C also reduced the proportion of undesired isomers, increasing selectivity for levopimaradiene up to 97%, while still maintaining improved productivity (FIG. 3d, and Table 5). In general, the strategies to search for beneficial mutations in LPS may also be applied to other important diterpenoid cyclases, such as the taxadiene synthase, because terpene cyclases have similar tertiary folds[45]. Several GGPPS variants that conferred diterpenoid production increase were identified by random mutagenesis and utilizing a lycopene pathway as a screening system. A GGPPS variant harboring S239C/G295D, when combined with LPS M593I/Y700F created a mutant pathway that improved the levopimaradiene titer by ~19-fold over wild-type. In controlled culture conditions, diterpenoid titer from the pre-engineered E. coli harboring the highest-producing mutant pathway reached ~800 mg/L, of which ~700 mg/L constituted levopimaradiene. Readily available levopimaradiene opens the possibility for utilization as a biotranformation substrate in plant tissue/cell culture to synthesize ginkgolides[7] or derivatization for developing new pharmaceuticals using synthetic chemistry[46]. Additionally, because GGPPS is required in all diterpenoid pathways, the GGPPS mutant identified in this work should also find application to for the synthesis of other precursors for other important plant diterpenoids such as Taxol (cancer chemotherapeutics), gib-berellins (plant growth hormones), and steviol glycosides (a natural sweetener that does not induce glycemic responses).

The approval of more than 100 new natural product-derived drugs for clinical trial in 2007 signifies the long-standing role of these molecules as effective therapeutics. Yet, this figure represents about a 30% drop since 2001[47]. One of the major challenges in many natural product research efforts is the reliance on bioprospecting, which typically generates low yield. This work demonstrated that by transferring and reengineering a heterologous biosynthetic pathway, the high level production of a plant-derived pharmaceutical can be achieved in a microbial host. This pathway 'reprogramming' framework should further enhance the extent of production improvement via metabolic engineering and complement a recently developed tool to mediate metabolite channeling in vivo[48]. In a broader sense, because terpenoid pathways also lead to compounds used in flavors, cosmetics, and biofuels, this strategy should also be readily extended to overproduce many commercially important compounds using microbial biotechnology.

Methods

Cloning and Pathway Construction

The sequences of ggpps[43] and lps[49] were obtained from Taxus canadensis and G. biloba, respectively (Genbank accession codes: AF081514 and AF331704). Genes were custom-synthesized (DNA 2.0) to incorporate E. coli codon bias, remove restriction sites for cloning purposes, and establish a ~50% GC-content. Nucleotides corresponding to the 98 N-terminal amino acids of GGPPS (plastid transit peptide) were removed by designing custom oligonucleotides to generate mature proteins as previously described[43]. In the case of LPS, truncation of 40 N-terminal amino acids was chosen because its incorporation into the levopimaradiene pathway gave rise to the most stable diterpenoid production in comparison to 60- and 80-amino acid truncation. In all cases, a start codon was introduced in the truncated gene fragments. For creating mutagenesis templates and sequencing purposes, ggpps and lps were individually cloned into pTrc99A (GE Healthcare) into the HindIII-EcoRI and EcoRI-SalI restriction sites, respectively.

The levopimaradiene pathways (wild type and mutants) were constructed by cloning PCR fragments of ggpps and lps into the HindIII-EcoRI and EcoRI-SalI sites of pTrcMod[50] to create pTrcGGPPS-LPS. To allow high throughput screening of GGPPS mutants, the to biosynthetic gene cluster consisting of crtB and crtI derived from plasmid pAC-LYC[16] were cloned into the EcoRI-SalI sites of pTrcMod to yield pTrc-CRT. The mutant ggpps library was subsequently cloned into pTrcCRT in between the HindIII and EcoRI sites to create pTrcGGPPS*-CRT. In all cases, E. coli MG1655 Δ (endA, recA) overexpressing the MEP pathway was used as the expression strain of the various pathways (wild-type and mutant levopimaradiene pathways, wild-type and mutant lycopene pathways). The episomal overexpression of the MEP pathway was mediated by first cloning the operon consisting of dxs, idi, and ispFD into the NcoI-KpnI of pTrcMod to yield pTrcMEP. The trc promoter and lacIq sequences were then amplified together with the MEP operon and sub-cloned into the PmeI and MluI sites of pACYC184 to create plasmid pACMEP.

Culture Growth and Library Analysis

Single transformants of pre-engineered E. coli strains harboring pACME or their mutant variants were cultivated for 18 h at 30° C. in Luria-Bertani (LB) medium. For library characterization, these preinnocula were used to seed fresh 2-mL cultures at a starting $A_{600}$ of 0.1. The medium was composed of yeast extract, 5 g/L; Trypton, 10 g/L; glycerol, 15 g/L; NaCl, 10 g/L; HEPES, 100 mM; pH was adjusted to 7.6.

Cultures were grown for 120 h at 22° C. prior to diterpenoid analysis. Scale-up experiments were done in 1-L bioreactors using. The media composition was as follow: $KH_2PO_4$, 13.3 g/L; $(NH_4)_2HPO_4$, 4 g/L; citric acid, 1.7 g/L; EDTA, 0.0084 g/L; $CoCl_2$, 0.0025 g/L; $MnCl_2$, 0.015 g/L; $CuCl_2$, 0.0015 g/L; $H_3BO_3$, 0.003 g/L; $Na_2MoO_4$, 0.0025 g/L; $Zn(CH_3COO)_2$, 0.008 g/L; Fe(III) citrate, 0.06 g/L; thiamine, 0.0045 g/L; $MgSO_4$, 1.3 g/L; yeast extract, 5 g/L; antifoam B, 3 mL/L; pH was maintained at 7.0. Glycerol was initially supplied at 10 g/L, it was intermittently fed so that the concentration did not reach below 3 g/L. The aeration level was set to 0.5 vvm, dissolved oxygen level was controlled at more than 20% during the course of fermentation by increasing agitation speed. All cultures were supplemented with 100 μg/mL ampicillin and 34 μg/mL chloramphenicol. To minimize the loss of diterpenoids due to air-stripping, 2% dodecane was added into the culture.

For analysis of small-scale cultivations (libraries), 1 mL hexane was added into 1.5 mL culture aliquots and vortexed for 30 min The mixture was centrifuged to separate the organic layer. For analysis of bioreactor cultivations, 1 μL of the dodecane layer was diluted to 200 μL with hexane. In both cases, 1 μL of hexane (containing the analytes) was analyzed by GC-MS (Varian Saturn 3800 GC attached to a Varian 2000 MS). The sample was injected to into a HP5ms column 30 m×250 μM×0.25 μM thickness (Agilent). Helium (ultra purity) at a flow rate 1.0 ml/min was used as a carrier gas. The oven temperature was first kept constant at 50° C. for 1 min, and then increased to 220° C. at the increment of 10° C./min, and finally held at this temperature for 10 min. The injector and transfer line temperatures were set at 200° C. and 250° C., respectively. Because levopimaradiene, abietadiene, and sandaracopimaradiene are not commercially available, taxadiene, a diterpenoid possessing the same molecular mass as levopimaradiene, abietadiene, sandaracopimaradiene was used to construct a calibration curve for the peak areas obtained from the GC-MS.

Molecular Modeling

The 3D structural model of LPS was built based on EAS (Protein Data Bank ID code 5EAT). Sequence alignment (FIG. 7) was performed with the clustalW method with standard gap penalties. While LPS contains 323 residues in excess of EAS, they aligned almost exclusively at the proximity of the second active side (towards the C-terminus), with a virtually gapless alignment. The CHARMM molecular modeling software with the CHARMm27 parameter set was used to mutate residues. Partial atomic charges needed for the substrate were obtained quantum mechanically with the Gaussian program using the 6-31G* basis set.

Mutant Library Generation and Screening

The introduction of point mutations and saturation mutagenesis in lps were performed using QuikChange II XL (Stratagene). Nucleotide changes were set by custom designed oligonucleotides (Table 7). Subsequent to sequencing to verify nucleotide changes, the lps variants were used to replace the wild-type lps in pTrcGGPPS-LPS and subjected to expression in the pre-engineered E. coli for production analysis. Random mutagenesis library of ggpps was created by error-prone (EP) PCR at low mutation rate using GeneMorph II (Stratagene). A pool of plasmid pTrcGGPPS*-CRT was isolated from more than ~$10^6$ transformants of E. coli DH10B. The plasmid library was then used to transform the E. coli strain overexpressing the MEP pathway for colorimetric screening. Colonies that displayed bright red coloration were isolated after incubation at 25° C. for 3 days (as visualized on Luria-Bertani solid medium containing 75 μg/mL ampicillin and 25 μg/mL chloramphenicol). Following plasmid extraction and sequencing, the mutant ggpps genes were used as a pool in the next round of EP PCR. As a control, the integration of wild-type ggpps into the lycopene pathway gave rise to orange colored transformants. The iteration of mutation and screening was stopped after the $2^{nd}$ round of mutant collection, as no colony that displayed higher red coloration was identified in the $3^{rd}$ round of EP PCR.

TABLE 1

Diterpenoid production from pre-engineered E. coli strains harboring GGPPS and LPS mutants (phylogenetically-based mutations)

| LPS mutation | Titer (mg/L) |
|---|---|
| WT | 26.5 |
| M593I | 98.6 |
| C618N | 4.0 |
| L619F | 12.7 |
| A620T | 33.9 |
| L696Q | 42.0 |
| Y700H | 11.5 |
| K723S | 48.0 |
| A727S | 0.0 |
| A729G | 0.6 |
| V731L | 2.3 |
| N769A | 0.0 |
| E777A | 0.0 |
| N838E | 58.5 |
| G854T | 36.8 |
| I855L | 17.7 |

WT, wild type LPS.
Quantification of production was determined based on sampling an average of three independent E. coli colonies harboring the mutated pathway. Standard deviations were lower than 5%.

TABLE 2

Diterpenoid production from pre-engineered E. coli strains harboring GGPPS and LPS mutants (saturation mutagenesis of Met593)

| LPS Met593 Mutation | Product Selectivity (%) | | | Titer (mg/L) |
|---|---|---|---|---|
| | 1 | 2 | 3 | |
| WT | 87 | 11 | 2 | 26.5 |
| Ala | 65 | 26 | 9 | 16.2 |
| Cys | 65 | 28 | 7 | 48.4 |
| Asp | 51 | 15 | 34 | 10.3 |
| Glu | 30 | 7 | 63 | 9.7 |
| Phe | ND | ND | 100 | 3.8 |
| Gly | 67 | 23 | 10 | 1.3 |
| His | ND | ND | ND | 0.0 |
| Ile | 84 | 12 | 5 | 98.6 |
| Lys | ND | ND | ND | 0.0 |
| Leu | 80 | 13 | 7 | 55.2 |
| Asn | 75 | 11 | 14 | 40.4 |
| Pro | 49 | 8 | 43 | 12.6 |
| Gln | 43 | TA | 57 | 8.6 |
| Arg | TA | ND | 100 | 4.6 |
| Ser | 80 | 11 | 9 | 39.8 |
| Thr | 78 | 16 | 6 | 40.2 |
| Val | 71 | 22 | 6 | 18.2 |

TABLE 2-continued

Diterpenoid production from pre-engineered E. coli strains harboring GGPPS and LPS mutants (saturation mutagenesis of Met593)

| LPS Met593 Mutation | Product Selectivity (%) | | | Titer (mg/L) |
|---|---|---|---|---|
| | 1 | 2 | 3 | |
| Trp | ND | ND | ND | 0.0 |
| Tyr | ND | ND | ND | 0.0 |

WT, wild type LPS;
TA, trace amounts (<0.1%);
ND, not detected.
Levopimaradiene, 1;
abietadiene, 2;
sandaracopimaradiene, 3.
Neoabietadiene is not included in the table because it was only produced in trace amounts in all strains.
Quantification of production was determined based on sampling an average of three independent E. coli colonies harboring the mutated pathway. Standard deviations were lower than 5%.

TABLE 3

Diterpenoid production from pre-engineered E. coli strains harboring GGPPS and LPS mutants (saturation mutagenesis of Ala620)

| LPS Ala620 Mutation | Product Selectivity (%) | | | Titer (mg/L) |
|---|---|---|---|---|
| | 1 | 2 | 3 | |
| WT | 87 | 11 | 2 | 26.5 |
| Cys | 87 | 10 | 3 | 40.0 |
| Asp | 97 | 2 | 1 | 1.7 |
| Glu | ND | ND | ND | 0.0 |
| Phe | ND | ND | ND | 0.0 |
| Gly | 86 | 12 | 2 | 29.2 |
| His | 100 | ND | ND | 0.9 |
| Ile | ND | ND | ND | 0.0 |
| Lys | ND | ND | ND | 0.0 |
| Leu | 97 | 2 | 1 | 7.3 |
| Met | ND | ND | ND | 0.0 |
| Asn | 97 | 2 | 1 | 2.6 |
| Pro | ND | ND | ND | 0.0 |
| Gln | ND | ND | ND | 0.0 |
| Arg | ND | ND | ND | 0.0 |
| Ser | 92 | 8 | TA | 42.2 |
| Thr | 87 | 11 | 2 | 33.9 |
| Val | 92 | 8 | TA | 42.5 |
| Trp | ND | ND | ND | 0.0 |
| Tyr | ND | ND | ND | 0.0 |

WT, wild type LPS;
TA, trace amounts (<0.1%);
ND, not detected.
Levopimaradiene, 1;
abietadiene, 2;
sandaracopimaradiene, 3.
Neoabietadiene is not included in the table because it was only produced in trace amounts in all strains.
Quantification of production was determined based on sampling an average of three independent E. coli colonies harboring the mutated pathway. Standard deviations were lower than 5%.

TABLE 4

Diterpenoid production from pre-engineered E. coli strains harboring GGPPS and LPS mutants (saturation mutagenesis of Tyr700)

| LPS Tyr700 Mutation | Product Selectivity (%) | | | Titer (mg/L) |
|---|---|---|---|---|
| | 1 | 2 | 3 | |
| WT | 87 | 11 | 2 | 26.5 |
| Ala | 81 | 9 | 10 | 75.6 |

TABLE 4-continued

Diterpenoid production from pre-engineered E. coli strains harboring GGPPS and LPS mutants (saturation mutagenesis of Tyr700)

| LPS Tyr700 Mutation | Product Selectivity (%) | | | Titer (mg/L) |
|---|---|---|---|---|
| | 1 | 2 | 3 | |
| Cys | 76 | 7 | 17 | 59.1 |
| Asp | 81 | ND | 19 | 13.3 |
| Glu | 64 | 7 | 29 | 46.3 |
| Phe | 79 | 16 | 5 | 133.5 |
| Gly | 79 | 6 | 15 | 36.1 |
| His | 74 | ND | 26 | 6.2 |
| Ile | 60 | 6 | 34 | 31.5 |
| Lys | TA | ND | 100 | 4.3 |
| Leu | 72 | 7 | 21 | 48.2 |
| Met | 80 | 13 | 7 | 132.8 |
| Asn | 70 | 9 | 21 | 60.2 |
| Pro | 56 | ND | 44 | 8.3 |
| Gln | 59 | 6 | 35 | 41.2 |
| Arg | 33 | ND | 67 | 5.0 |
| Ser | 78 | 7 | 15 | 84.9 |
| Thr | 72 | 7 | 21 | 65.4 |
| Val | 56 | 6 | 38 | 31.3 |
| Trp | 84 | 6 | 10 | 100.7 |

WT, wild type LPS;
TA, trace amounts (<0.1%);
ND, not detected.
Levopimaradiene, 1;
abietadiene, 2;
sandaracopimaradiene, 3.
Neoabietadiene is not included in the table because it was only produced in trace amounts in all strains.
Quantification of production was determined based on sampling an average of three independent E. coli colonies harboring the mutated pathway. Standard deviations were lower than 5%.

TABLE 5

Diterpenoid production from pre-engineered E. coli strains harboring GGPPS and LPS M593I mutants (saturation mutagenesis of Tyr700)

| LPS (M593I) Tyr700 mutation | Product Selectivity (%) | | | Titer (mg/L) |
|---|---|---|---|---|
| | 1 | 2 | 3 | |
| WT | 87 | 11 | 2 | 26.5 |
| Ala | 91 | 2 | 7 | 167.8 |
| Cys | 97 | 1 | 2 | 155.7 |
| Asp | 85 | TA | 15 | 66.1 |
| Glu | 60 | TA | 40 | 92.4 |
| Phe | 84 | 9 | 7 | 273.8 |
| Gly | 80 | TA | 20 | 59.2 |
| His | 70 | TA | 30 | 63.8 |
| Ile | 65 | TA | 35 | 78.6 |
| Lys | ND | ND | ND | 0.0 |
| Leu | 73 | 2 | 25 | 97.4 |
| Met | 89 | 2 | 9 | 132.1 |
| Asn | 79 | TA | 21 | 93.7 |
| Pro | 0 | TA | ND | 0.0 |
| Gln | 60 | TA | 40 | 26.9 |
| Arg | ND | ND | ND | 0.0 |
| Ser | 84 | TA | 16 | 48.1 |
| Thr | 73 | TA | 27 | 22.7 |

TABLE 5-continued

Diterpenoid production from pre-engineered E. coli strains harboring GGPPS and LPS M593I mutants (saturation mutagenesis of Tyr700)

| LPS (M593I) | Product Selectivity (%) | | | |
|---|---|---|---|---|
| Tyr700 mutation | 1 | 2 | 3 | Titer (mg/L) |
| Val | 91 | TA | 9 | 83.5 |
| Trp | 63 | TA | 37 | 51.6 |

WT, wild-type LPS;
TA, trace amounts (<0.1%);
ND, not detected.
Levopimaradiene, 1;
abietadiene, 2;
sandaracopimaradiene, 3.
Neoabietadiene is not included in the table because it was only produced in trace amounts in all strains.
Quantification of production was determined based on sampling an average of three independent E. coli colonies harboring the mutated pathway. Standard deviations were lower than 5%.

TABLE 6

Diterpenoid production from pre-engineered E. coli strains harboring isolated GGPPS mutants and the LPS M593I/Y700F variant

| GGPPS mutation | Titer (mg/L) |
|---|---|
| WT | 273.8 |
| G1 | 261.3 |
| G2 | 396.2 |
| G3 | 343.2 |
| G4 | 316.8 |
| G5 | 257.1 |
| G6 | 242.4 |
| G7 | 380.9 |
| G8 | 351.0 |
| G9 | 350.7 |
| G10 | 468.7 |
| G11 | 211.8 |
| G12 | 366.8 |
| G13 | 411.1 |
| G14 | 287.2 |
| G15 | 406.7 |

WT, wild type GGPPS.
Quantification of production was determined based on sampling an average of three independent E. coli colonies harboring the mutated pathway. Standard deviations were lower than 5%.

TABLE 7

Custom oligonucleotides used for LPS mutagenesis

| Mutation | 5'-3' Sequence |
|---|---|
| F-C618N | CGTACGCAAAAACCTCTAACCTGGCCGTAATCCTGG (SEQ ID NO: 5) |
| R-C618N | CCAGGATTACGGCCAGGTTAGAGGTTTTTGCGTACG (SEQ ID NO: 6) |
| F-L619F | GCAAAACCTCTTGCTTCGCCGTAATCCTGGACGATC (SEQ ID NO: 7) |
| R-L619F | GATCGTCCAGGATTACGGCGAAGCAAGAGGTTTTGC (SEQ ID NO: 8) |
| F-L696Q | GTAAAGTTTGGGAGGGCCAGCTGGCCTCCTATAC (SEQ ID NO: 9) |
| R-L696Q | GTATAGGAGGCCAGCTGGCCCTCCCAAACTTTAC (SEQ ID NO: 10) |
| F-K723S | GTATGTCGAGAACGCTAGTGTTAGCATCGCGCTGG (SEQ ID NO: 11) |
| R-K723S | CCAGCGCGATGCTAACACTAGCGTTCTCGACATAC (SEQ ID NO: 12) |
| F-A727S | CTAAAGTTAGCATCTCGCTGGCGACCGTTGTTCTG (SEQ ID NO: 13) |
| R-A727S | CAGAACAACGGTCGCCAGCGAGATGCTAACTTTAG (SEQ ID NO: 14) |
| F-A729G | CTAAAGTTAGCATCGCGCTGGGGACCGTTGTTCTG (SEQ ID NO: 15) |
| R-A729G | CAGAACAACGGTCCCCAGCGCGATGCTAACTTTAG (SEQ ID NO: 16) |
| F-V731L | CATCGCGCTGGCGACCCTTGTTCTGAACTC (SEQ ID NO: 17) |
| R-V731L | GAGTTCAGAACAAGGGTCGCCAGCGCGATG (SEQ ID NO: 18) |
| F-N769A | CCGGCCGTCTGATTGCCGACACCAAAACCTATCAG (SEQ ID NO: 19) |
| R-N769A | CTGATAGGTTTTGGTGTCGGCAATCAGACGGCCGG (SEQ ID NO: 20) |
| F-E777A | CCAAAACCTATCAGGCTGCACGTAACCGTGG (SEQ ID NO: 21) |
| R-E777A | CCACGGTTACGTGCAGCCTGATAGGTTTTGG (SEQ ID NO: 22) |
| F-N838E | CGTCGTCTGCTGTTCGAGACCGCGCGTGTAATGC (SEQ ID NO: 23) |
| R-N838E | GCATTACACGCGCGGTCTCGAACAGCAGACGACG (SEQ ID NO: 24) |
| F-G854T | GTACCGCGATGGCTTCACCATCAGCGATAAAGAAATG (SEQ ID NO: 25) |
| R-G854T | CATTTCTTTATCGCTGATGGTGAAGCCATCGCGGTAC (SEQ ID NO: 26) |
| F-I855L | CCGCGATGGCTTCGGCCTCAGCGATAAAG (SEQ ID NO: 27) |
| R-I855L | CTTTATCGCTGAGGCCGAAGCCATCGCGG (SEQ ID NO: 28) |
| F-M593A | GTCAGCGCCCGGTTGAAGCGTACTTTTCTGTTGCAG (SEQ ID NO: 29) |
| R-M593A | CTGCAACAGAAAAGTACGCTTCAACCGGGCGCTGAC (SEQ ID NO: 30) |
| F-M593C | GTCAGCGCCCGGTTGAATGTTACTTTTCTGTTGCAG (SEQ ID NO: 31) |
| R-M593C | CTGCAACAGAAAAGTAACATTCAACCGGGCGCTGAC (SEQ ID NO: 32) |
| F-M593D | GTCAGCGCCCGGTTGAAGACTACTTTTCTGTTGCAG (SEQ ID NO: 33) |
| R-M593D | CTGCAACAGAAAAGTAGTCTTCAACCGGGCGCTGAC (SEQ ID NO: 34) |
| F-M593E | GTCAGCGCCCGGTTGAAGAGTACTTTTCTGTTGCAG (SEQ ID NO: 35) |

TABLE 7-continued

Custom oligonucleotides used for LPS mutagenesis

| Mutation | 5'-3' Sequence |
|---|---|
| R-M593E | CTGCAACAGAAAAGTACTCTTCAACCGGGCGCTGAC (SEQ ID NO: 36) |
| F-M593F | GTCAGCGCCCGGTTGAATTTTACTTTTCTGTTGCAG (SEQ ID NO: 37) |
| R-M593F | CTGCAACAGAAAAGTAAAATTCAACCGGGCGCTGAC (SEQ ID NO: 38) |
| F-M593G | GTCAGCGCCCGGTTGAAGGGTACTTTTCTGTTGCAG (SEQ ID NO: 39) |
| R-M593G | CTGCAACAGAAAAGTACCCTTCAACCGGGCGCTGAC (SEQ ID NO: 40) |
| F-M593H | FGTCAGCGCCCGGTTGAACACTACTTTTCTGTTGCAG (SEQ ID NO: 41) |
| R-M593H | CTGCAACAGAAAAGTAGTGTTCAACCGGGCGCTGAC (SEQ ID NO: 42) |
| F-M593I | GTCAGCGCCCGGTTGAAATCTACTTTTCTGTTGCAG (SEQ ID NO: 43) |
| R-M593I | CTGCAACAGAAAAGTAGATTTCAACCGGGCGCTGAC (SEQ ID NO: 44) |
| F-M593K | GTCAGCGCCCGGTTGAAAAATACTTTTCTGTTGCAG (SEQ ID NO: 45) |
| R-M593K | CTGCAACAGAAAAGTATTTTTCAACCGGGCGCTGAC (SEQ ID NO: 46) |
| F-M593L | GTCAGCGCCCGGTTGAATTGTACTTTTCTGTTGCAG (SEQ ID NO: 47) |
| R-M593L | CTGCAACAGAAAAGTACAATTCAACCGGGCGCTGAC (SEQ ID NO: 48) |
| F-M593N | GTCAGCGCCCGGTTGAAAACTACTTTTCTGTTGCAG (SEQ ID NO: 49) |
| R-M593N | CTGCAACAGAAAAGTAGTTTTCAACCGGGCGCTGAC (SEQ ID NO: 50) |
| F-M593Q | GTCAGCGCCCGGTTGAACAGTACTTTTCTGTTGCAG (SEQ ID NO: 51) |
| R-M593Q | CTGCAACAGAAAAGTACTGTTCAACCGGGCGCTGAC (SEQ ID NO: 52) |
| F-M593P | GTCAGCGCCCGGTTGAACCGTACTTTTCTGTTGCAG (SEQ ID NO: 53) |
| R-M593P | CTGCAACAGAAAAGTACGGTTCAACCGGGCGCTGAC (SEQ ID NO: 54) |
| F-M593R | GTCAGCGCCCGGTTGAAAGGTACTTTTCTGTTGCAG (SEQ ID NO: 55) |
| R-M593R | CTGCAACAGAAAAGTACCTTTCAACCGGGCGCTGAC (SEQ ID NO: 56) |
| F-M593S | GTCAGCGCCCGGTTGAATCGTACTTTTCTGTTGCAG (SEQ ID NO: 57) |
| R-M593S | CTGCAACAGAAAAGTACGATTCAACCGGGCGCTGAC (SEQ ID NO: 58) |
| F-M593T | GTCAGCGCCCGGTTGAAACGTACTTTTCTGTTGCAG (SEQ ID NO: 59) |
| R-M593T | CTGCAACAGAAAAGTACGTTTCAACCGGGCGCTGAC (SEQ ID NO: 60) |
| F-M593V | GTCAGCGCCCGGTTGAAGTGTACTTTTCTGTTGCAG (SEQ ID NO: 61) |
| R-M593V | CTGCAACAGAAAAGTACACTTCAACCGGGCGCTGAC (SEQ ID NO: 62) |
| F-M593W | GTCAGCGCCCGGTTGAATGGTACTTTTCTGTTGCAG (SEQ ID NO: 63) |
| R-M593W | CTGCAACAGAAAAGTACCATTCAACCGGGCGCTGAC (SEQ ID NO: 64) |
| F-M593Y | GTCAGCGCCCGGTTGAATATTACTTTTCTGTTGCAG (SEQ ID NO: 65) |
| R-M593Y | CTGCAACAGAAAAGTAATATTCAACCGGGCGCTGAC (SEQ ID NO: 66) |
| F-A620C | CCTCTTGCCTGTGCGTAATCCTGGACG (SEQ ID NO: 67) |
| R-A620C | CGTCCAGGATTACGCACAGGCAAGAGG (SEQ ID NO: 68) |
| F-A620D | CCTCTTGCCTGGACGTAATCCTGGACG (SEQ ID NO: 69) |
| R-A620D | CGTCCAGGATTACGTCCAGGCAAGAGG (SEQ ID NO: 70) |
| F-A620E | CCTCTTGCCTGGAAGTAATCCTGGACG (SEQ ID NO: 71) |
| R-A620E | CGTCCAGGATTACTTCCAGGCAAGAGG (SEQ ID NO: 72) |
| F-A620F | CCTCTTGCCTGTTCGTAATCCTGGACG (SEQ ID NO: 73) |
| R-A620F | CGTCCAGGATTACGAACAGGCAAGAGG (SEQ ID NO: 74) |
| F-A620G | CCTCTTGCCTGGGCGTAATCCTGGACG (SEQ ID NO: 75) |
| R-A620G | CGTCCAGGATTACGCCCAGGCAAGAGG (SEQ ID NO: 76) |
| F-A620H | CCTCTTGCCTGCACGTAATCCTGGACG (SEQ ID NO: 77) |
| R-A620H | CGTCCAGGATTACGTGCAGGCAAGAGG (SEQ ID NO: 78) |
| F-A620I | CCTCTTGCCTGATCGTAATCCTGGACG (SEQ ID NO: 79) |
| R-A620I | CGTCCAGGATTACGATCAGGCAAGAGG (SEQ ID NO: 80) |
| F-A620K | CCTCTTGCCTGAAAGTAATCCTGGACG (SEQ ID NO: 81) |
| R-A620K | CGTCCAGGATTACTTTCAGGCAAGAGG (SEQ ID NO: 82) |
| F-A620L | CCTCTTGCCTGCTCGTAATCCTGGACG (SEQ ID NO: 83) |
| R-A620L | CGTCCAGGATTACGAGCAGGCAAGAGG (SEQ ID NO: 84) |
| F-A620M | CCTCTTGCCTGATGGTAATCCTGGACG (SEQ ID NO: 85) |

TABLE 7-continued

Custom oligonucleotides used for LPS mutagenesis

| Mutation | 5'-3' Sequence |
|---|---|
| R-A620M | CGTCCAGGATTACCATCAGGCAAGAGG (SEQ ID NO: 86) |
| F-A620N | CCTCTTGCCTGAACGTAATCCTGGACG (SEQ ID NO: 87) |
| R-A620N | CGTCCAGGATTACGTTCAGGCAAGAGG (SEQ ID NO: 88) |
| F-A620P | CCTCTTGCCTGCCCGTAATCCTGGACG (SEQ ID NO: 89) |
| R-A620P | CGTCCAGGATTACGGGCAGGCAAGAGG (SEQ ID NO: 90) |
| F-A620Q | CCTCTTGCCTGCAAGTAATCCTGGACG (SEQ ID NO: 91) |
| R-A620Q | CGTCCAGGATTACTTGCAGGCAAGAGG (SEQ ID NO: 92) |
| F-A620R | CCTCTTGCCTGCGCGTAATCCTGGACG (SEQ ID NO: 93) |
| R-A620R | CGTCCAGGATTACGCGCAGGCAAGAGG (SEQ ID NO: 94) |
| F-A620S | CCTCTTGCCTGTCCGTAATCCTGGACG (SEQ ID NO: 95) |
| R-A620S | CGTCCAGGATTACGGACAGGCAAGAGG (SEQ ID NO: 96) |
| F-A620T | CCTCTTGCCTGACCGTAATCCTGGACG (SEQ ID NO: 97) |
| R-A620T | CGTCCAGGATTACGGTCAGGCAAGAGG (SEQ ID NO: 98) |
| F-A620V | CCTCTTGCCTGGTCGTAATCCTGGACG (SEQ ID NO: 99) |
| R-A620V | CGTCCAGGATTACGACCAGGCAAGAGG (SEQ ID NO: 100) |
| F-A620W | CCTCTTGCCTGTGGGTAATCCTGGACG (SEQ ID NO: 101) |
| R-A620W | CGTCCAGGATTACCCACAGGCAAGAGG (SEQ ID NO: 102) |
| F-A620Y | CCTCTTGCCTGTACGTAATCCTGGACG (SEQ ID NO: 103) |
| R-A620Y | CGTCCAGGATTACGTACAGGCAAGAGG (SEQ ID NO: 104) |
| F-Y700A | GGCCTGCTGGCCTCCGCTACCAAGGAAGCG (SEQ ID NO: 105) |
| R-Y700A | CGCTTCCTTGGTAGCGGAGGCCAGCAGGCC (SEQ ID NO: 106) |
| F-Y700C | GGCCTGCTGGCCTCCTGTACCAAGGAAGCG (SEQ ID NO: 107) |
| R-Y700C | CGCTTCCTTGGTACAGGAGGCCAGCAGGCC (SEQ ID NO: 108) |
| F-Y700D | GGCCTGCTGGCCTCCGATACCAAGGAAGCG (SEQ ID NO: 109) |
| R-Y700D | CGCTTCCTTGGTATCGGAGGCCAGCAGGCC (SEQ ID NO: 110) |
| F-Y700E | GGCCTGCTGGCCTCCGAAACCAAGGAAGCG (SEQ ID NO: 111) |
| R-Y700E | CGCTTCCTTGGTTTCGGAGGCCAGCAGGCC (SEQ ID NO: 112) |
| F-Y700F | GGCCTGCTGGCCTCCTTTACCAAGGAAGCG (SEQ ID NO: 113) |
| R-Y700F | CGCTTCCTTGGTAAAGGAGGCCAGCAGGCC (SEQ ID NO: 114) |
| F-Y700G | GGCCTGCTGGCCTCCGGTACCAAGGAAGCG (SEQ ID NO: 115) |
| R-Y700G | CGCTTCCTTGGTACCGGAGGCCAGCAGGCC (SEQ ID NO: 116) |
| F-Y700H | GGCCTGCTGGCCTCCCATACCAAGGAAGCG (SEQ ID NO: 117) |
| R-Y700H | CGCTTCCTTGGTATGGGAGGCCAGCAGGCC (SEQ ID NO: 118) |
| F-Y700I | GGCCTGCTGGCCTCCATTACCAAGGAAGCG (SEQ ID NO: 119) |
| R-Y700I | CGCTTCCTTGGTAATGGAGGCCAGCAGGCC (SEQ ID NO: 120) |
| F-Y700K | GGCCTGCTGGCCTCAAAACCAAGGAAGCG (SEQ ID NO: 121) |
| R-Y700K | CGCTTCCTTGGTTTTGGAGGCCAGCAGGCC (SEQ ID NO: 122) |
| F-Y700L | GGCCTGCTGGCCTCCTTAACCAAGGAAGCG (SEQ ID NO: 123) |
| R-Y700L | CGCTTCCTTGGTTAAGGAGGCCAGCAGGCC (SEQ ID NO: 124) |
| F-Y700M | GGCCTGCTGGCCTCCATGACCAAGGAAGCG (SEQ ID NO: 125) |
| R-Y700M | CGCTTCCTTGGTCATGGAGGCCAGCAGGCC (SEQ ID NO: 126) |
| F-Y700N | GGCCTGCTGGCCTCCAATACCAAGGAAGCG (SEQ ID NO: 127) |
| R-Y700N | CGCTTCCTTGGTATTGGAGGCCAGCAGGCC (SEQ ID NO: 128) |
| F-Y700P | GGCCTGCTGGCCTCCCCTACCAAGGAAGCG (SEQ ID NO: 129) |
| R-Y700P | CGCTTCCTTGGTAGGGGAGGCCAGCAGGCC (SEQ ID NO: 130) |
| F-Y700Q | GGCCTGCTGGCCTCCGAAACCAAGGAAGCG (SEQ ID NO: 131) |
| R-Y700Q | CGCTTCCTTGGTTTCGGAGGCCAGCAGGCC (SEQ ID NO: 132) |
| F-Y700R | GGCCTGCTGGCCTCCCGTACCAAGGAAGCG (SEQ ID NO: 133) |
| RY700R | CGCTTCCTTGGTACGGGAGGCCAGCAGGCC (SEQ ID NO: 134) |
| F-Y700S | GGCCTGCTGGCCTCCTCTACCAAGGAAGCG (SEQ ID NO: 135) |

TABLE 7-continued

Custom oligonucleotides used for LPS mutagenesis

| Mutation | 5'-3' Sequence |
|---|---|
| R-Y700S | CGCTTCCTTGGTAGAGGAGGCCAGCAGGCC (SEQ ID NO: 136) |
| F-Y700T | GGCCTGCTGGCCTCCACTACCAAGGAAGCG (SEQ ID NO: 137) |
| R-Y700T | CGCTTCCTTGGTAGTGGAGGCCAGCAGGCC (SEQ ID NO: 138) |
| F-Y700V | GGCCTGCTGGCCTCCGTTACCAAGGAAGCG (SEQ ID NO: 139) |
| R-Y700V | CGCTTCCTTGGTAACGGAGGCCAGCAGGCC (SEQ ID NO: 140) |
| F-Y700W | GGCCTGCTGGCCTCCTGGACCAAGGAAGCG (SEQ ID NO: 141) |
| R-Y700W | CGCTTCCTTGGTCCAGGAGGCCAGCAGGCC (SEQ ID NO: 142) |

The letter F and R in the beginning of each mutagenic oligonucleotide indicates 'forward' and 'reverse' sequence, respectively.

REFERENCES 1. van Beek, T. A. & Montoro, P. Chemical analysis and quality control of *Ginkgo biloba* leaves, extracts, and phytopharmaceuticals. J Chromatogr A 1216, 2002-32 (2009).
2. Aponte, M. et al. Activation of platelet-activating factor receptor and pleiotropic effects on to tyrosine phospho-EGFR/Src/FAK/paxillin in ovarian cancer. Cancer Res 68, 5839-48 (2008).
3. Heads, J. A., Hawthorne, R. L., Lynagh, T. & Lynch, J. W. Structure-activity analysis of ginkgolide binding in the glycine receptor pore. J Neurochem 105, 1418-27 (2008).
4. Ivic, L. et al. Terpene trilactones from *Ginkgo biloba* are antagonists of cortical glycine and GABA(A) receptors. J Biol Chem 278, 49279-85 (2003).
5. Jensen, A. A. et al. Probing the pharmacophore of ginkgolides as glycine receptor antagonists. J Med Chem 50, 1610-7 (2007).
6. Ye, B. et al. *Ginkgo biloba* and ovarian cancer prevention: epidemiological and biological evidence. Cancer Lett 251, 43-52 (2007).
7. Kang, S. M. et al. Effect of supplementing terpenoid biosynthetic precursors on the accumulation of bilobalide and ginkgolides in *Ginkgo biloba* cell cultures. J Biotechnol 123, 85-92 (2006).
8. Crimmins, M. T. et al. The total synthesis of (+/−)-ginkgolide B. Journal of the American Chemical Society 122, 8453-8463 (2000).
9. Carter, O. A., Peters, R. J. & Croteau, R. Monoterpene biosynthesis pathway construction in *Escherichia coli*. Phytochemistry 64, 425-33 (2003).
10. Engels, B., Dahm, P. & Jennewein, S. Metabolic engineering of taxadiene biosynthesis in yeast as a first step towards Taxol (Paclitaxel) production. Metab Eng 10, 201-6 (2008).
11. Huang, Q., Roessner, C. A., Croteau, R. & Scott, A. I. Engineering *Escherichia coli* for the synthesis of taxadiene, a key intermediate in the biosynthesis of taxol. Bioorg Med Chem 9, 2237-42 (2001).
12. Reiling, K. K. et al. Mono and diterpene production in *Escherichia coli*. Biotechnol Bioeng 87, 200-12 (2004).
13. Ro, D. K. et al. Production of the antimalarial drug precursor artemisinic acid in engineered yeast. Nature 440, 940-3 (2006).
14. Leonard, E., Runguphan, W., O'Connor, S. & Prather, K. J. Opportunities in metabolic engineering to facilitate scalable alkaloid production. Nat Chem Biol 5, 292-300 (2009).
15. Roberts, S. C. Production and engineering of terpenoids in plant cell culture. Nat Chem Biol 3, 387-95 (2007).
16. Alper, H., Miyaoku, K. & Stephanopoulos, G. Construction of lycopene-overproducing *E. coli* strains by combining systematic and combinatorial gene knockout targets. Nat Biotechnol 23, 612-6 (2005).
17. Conrado, R. J., Varner, J. D. & DeLisa, M. P. Engineering the spatial organization of metabolic enzymes: mimicking nature's synergy. Curr Opin Biotechnol 19, 492-9 (2008).
18. Fong, S. S., Nanchen, A., Palsson, B. O. & Sauer, U. Latent pathway activation and increased pathway capacity enable *Escherichia coli* adaptation to loss of key metabolic enzymes. J Biol Chem 281, 8024-33 (2006).
19. Copley, S. D. Evolution of efficient pathways for degradation of anthropogenic chemicals. Nat Chem Biol 5, 559-66 (2009).
20. Fischbach, M. A. & Clardy, J. One pathway, many products. Nat Chem Biol 3, 353-5 (2007).
21. Jensen, R. A. Enzyme recruitment in evolution of new function. Annu Rev Microbiol 30, 409-25 (1976).
22. Le Rouzic, A. & Carlborg, O. Evolutionary potential of hidden genetic variation. Trends Ecol Evol 23, 33-7 (2008).
23. Sniegowski, P. D. & Murphy, H. A. Evolvability. Curr Biol 16, R831-4 (2006).
24. Aharoni, A. et al. The 'evolvability' of promiscuous protein functions. Nat Genet 37, 73-6 (2005).
25. Tracewell, C. A. & Arnold, F. H. Directed enzyme evolution: climbing fitness peaks one amino acid at a time. Curr Opin Chem Biol 13, 3-9 (2009).
26. O'Maille, P. E. et al. Quantitative exploration of the catalytic landscape separating divergent plant sesquiterpene synthases. Nat Chem Biol 4, 617-23 (2008).
27. Ohnuma, S. et al. A pathway where polyprenyl diphosphate elongates in prenyltransferase. Insight into a common mechanism of chain length determination of prenyltransferases. J Biol Chem 273, 26705-13 (1998).
28. Peters, R. J. et al. Abietadiene synthase from grand fir (*Abies grandis*): characterization and mechanism of action of the "pseudomature" recombinant enzyme. Biochemistry 39, 15592-602 (2000).
29. Ravn, M. M., Coates, R. M., Flory, J. E., Peters, R. J. & Croteau, R. Stereochemistry of the cyclization-rearrangement of (+)-copalyl diphosphate to (−)-abietadiene catalyzed by recombinant abietadiene synthase from *Abies grandis*. Org Lett 2, 573-6 (2000).
30. Starks, C. M., Back, K., Chappell, J. & Noel, J. P. Structural basis for cyclic terpene biosynthesis by tobacco 5-epi-aristolochene synthase. Science 277, 1815-20 (1997).
31. Keeling, C. I., Weisshaar, S., Lin, R. P. & Bohlmann, J. Functional plasticity of paralogous diterpene synthases involved in conifer defense. Proc Natl Acad Sci USA 105, 1085-90 (2008).
32. Peters, R. J. & Croteau, R. B. Abietadiene synthase catalysis: mutational analysis of a prenyl diphosphate ionization-initiated cyclization and rearrangement. Proc Natl Acad Sci USA 99, 580-4 (2002).
33. Yoshikuni, Y., Ferrin, T. E. & Keasling, J. D. Designed divergent evolution of enzyme function. Nature 440, 1078-82 (2006).

34. Greenhagen, B. T., O'Maille, P. E., Noel, J. P. & Chappell, J. Identifying and manipulating structural determinates linking catalytic specificities in terpene synthases. Proc Natl Acad Sci USA 103, 9826-31 (2006).
35. Kyte, J. & Doolittle, R. F. A simple method for displaying the hydropathic character of a protein. J Mol Biol 157, 105-32 (1982).
36. Monera, O. D., Sereda, T. J., Zhou, N. E., Kay, C. M. & Hodges, R. S. Relationship of sidechain hydrophobicity and alpha-helical propensity on the stability of the single-stranded to amphipathic alpha-helix. J Pept Sci 1, 319-29 (1995).
37. Bloom, J. D. & Arnold, F. H. In the light of directed evolution: pathways of adaptive protein evolution. Proc Natl Acad Sci USA 106 Suppl 1, 9995-10000 (2009).
38. Li, Y. et al. A diverse family of thermostable cytochrome P450s created by recombination of stabilizing fragments. Nat Biotechnol 25, 1051-6 (2007).
39. Bloom, J. D., Romero, P. A., Lu, Z. & Arnold, F. H. Neutral genetic drift can alter promiscuous protein functions, potentially aiding functional evolution. Biol Direct 2, 17 (2007).
40. Nims, E., Dubois, C. P., Roberts, S. C. & Walker, E. L. Expression profiling of genes involved in paclitaxel biosynthesis for targeted metabolic engineering. Metab Eng 8, 385-94 (2006).
41. Kloer, D. P., Welsch, R., Beyer, P. & Schulz, G. E. Structure and reaction geometry of geranylgeranyl diphosphate synthase from *Sinapis alba*. Biochemistry 45, 15197-204 (2006).
42. Liao, Z. et al. A new geranylgeranyl diphosphate synthase gene from *Ginkgo biloba*, which intermediates the biosynthesis of the key precursor for ginkgolides. DNA Seq 15, 153-8 (2004).
43. Hefner, J., Ketchum, R. E. B. & Croteau, R. Cloning and functional expression of a cDNA encoding geranylgeranyl diphosphate synthase from *Taxus canadensis* and assessment of the role of this prenyltransferase in cells induced for Taxol production. Archives of Biochemistry and Biophysics 360, 62-74 (1998).
44. Hosfield, D. J. et al. Structural basis for bisphosphonate-mediated inhibition of isoprenoid biosynthesis. J Biol Chem 279, 8526-9 (2004).
45. Trapp, S. C. & Croteau, R. B. Genomic organization of plant terpene synthases and molecular evolutionary implications. Genetics 158, 811-32 (2001).
46. Gonzalez, M. A., Correa-Royero, J., Agudelo, L., Mesa, A. & Betancur-Galvis, L. Synthesis and biological evaluation of abietic acid derivatives. Eur J Med Chem 44, 2468-72 (2009).
47. Li, J. W. & Vederas, J. C. Drug discovery and natural products: end of an era or an endless frontier? Science 325, 161-5 (2009).
48. Dueber, J. E. et al. Synthetic protein scaffolds provide modular control over metabolic flux. Nat Biotechnol 27, 753-9 (2009).
49. Schepmann, H. G., Pang, J. & Matsuda, S. P. Cloning and characterization of *Ginkgo biloba* levopimaradiene synthase which catalyzes the first committed step in ginkgolide to biosynthesis. Arch Biochem Biophys 392, 263-9 (2001).
50. Leonard, E. & Koffas, M. A. Engineering of artificial plant cytochrome P450 enzymes for synthesis of isoflavones by *Escherichia coli*. Appl Environ Microbiol 73, 7246-51 (2007).
51. Cyr, A., Wilderman, P. R., Determan, M. & Peters, R. J. A modular approach for facile biosynthesis of labdane-related diterpenes. J Am Chem Soc 129, 6684-5 (2007).
52. Martin, D. M., Faldt, J. & Bohlmann, J Functional characterization of nine Norway Spruce TPS genes and evolution of gymnosperm terpene synthases of the TPS-d subfamily Plant Physiol 135, 1908-27 (2004).
53. Facchini, P. J. & Chappell, J. Gene family for an elicitor-induced sesquiterpene cyclase in tobacco. Proc Natl Acad Sci USA 89, 11088-92 (1992).
54. Hill, A. M., Cane, D. E., Mau, C. J. & West, C. A. High level expression of *Ricinus communis* casbene synthase in *Escherichia coli* and characterization of the recombinant enzyme. Arch Biochem Biophys 336, 283-9 (1996).
55. Huang, K. X., Huang, Q. L., Wildung, M. R., Croteau, R. & Scott, A. I. Overproduction, in *Escherichia coli*, of soluble taxadiene synthase, a key enzyme in the Taxol biosynthetic pathway. Protein Expr Purif 13, 90-6 (1998).
56. Morrone, D. et al. An unexpected diterpene cyclase from rice: functional identification of a stemodene synthase. Arch Biochem Biophys 448, 133-40 (2006).
57. Toyomasu, T. Recent advances regarding diterpene cyclase genes in higher plants and fungi. Biosci Biotechnol Biochem 72, 1168-75 (2008).
58. Dairi, T. et al. Eubacterial diterpene cyclase genes essential for production of the isoprenoid antibiotic terpentecin. J Bacteriol 183, 6085-94 (2001).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the to specific purpose mentioned herein.

What is claimed is:

1. A microbial cell that overexpresses one or more components of the non-mevalonate (MEP) pathway, wherein the microbial cell recombinantly expresses a functional levopimaradiene synthase (LPS) enzyme as set forth in SEQ ID NO: 2 containing a mutation at position M593, and a geranylgeranyl diphosphate synthase (GGPPS) enzyme.

2. The microbial cell of claim 1, wherein the LPS enzyme further contains a mutation at one or more of the residues selected from the group consisting of: C618, A620, L696, Y700, K723, A729, V731, N838, and I855.

3. The microbial cell of claim 2, wherein the LPS enzyme further contains one or more mutations selected from the group consisting of: M593I, M593L, C618N, L696Q, K723S, V731L, N838E, I855L, A729G, Y700H, Y700A, Y700C, Y700F, Y700M, Y700W, A620C, A620G, A620S, A620T and A620V.

4. The microbial cell of claim 1, wherein the GGPPS enzyme as set forth in SEQ ID NO: 4 contains a mutation at residue S239 and/or G295, optionally wherein the GGPPS enzyme contains the mutation S239C and/or G295D.

5. The microbial cell of claim 4, wherein the LPS enzyme contains the mutation M593I and/or Y700F, and the GGPPS enzyme contains the mutation S239C and/or G295D.

6. The microbial cell of claim 1, wherein the cell produces a terpenoid, optionally wherein the terpenoid has one or more cyclic structures.

7. The microbial cell of claim 6, wherein the terpenoid is a diterpenoid, optionally wherein the diterpenoid is levopimaradiene.

8. The microbial cell of claim 1, wherein the cell produces a Taxol®, a gibberellin, and/or a steviol glycoside.

9. A microbial cell that recombinantly expresses a functional levopimaradiene synthase (LPS) enzyme as set forth in SEQ ID NO: 2 containing a mutation at position M593, optionally wherein the LPS enzyme further contains a mutation at one or more of the residues selected from the group consisting of: C618, A620, L696, Y700, K723, A729, V731, N838, and I855.

10. The microbial cell of claim 9, wherein the LPS enzyme contains one or more mutations selected from the group consisting of: M593I, M593L, C618N, L696Q, K723S, V731 L, N838E, I855L, A729G, Y700H, Y700A, Y700C, Y700F, Y700M, Y700W, A620C, A620G, A620S, A620T and A620V.

11. The microbial cell of claim 9, wherein the LPS enzyme contains the mutation M593I and one of the mutations selected from the group consisting of Y700A, Y700C and Y700F.

12. A microbial cell that recombinantly expresses a functional geranylgeranyl diphosphate synthase (GGPPS) enzyme as set forth in SEQ ID NO: 4 containing a mutation at residue S239 and/or G295, optionally wherein the GGPPS enzyme contains the mutation S239C and/or G295D.

13. A method of recombinantly expressing a levopimaradiene synthase (LPS) enzyme and a geranylgeranyl diphosphate synthase (GGPPS) enzyme in a microbial cell comprising: recombinantly expressing a LPS enzyme and a GGPPS enzyme using the microbial cell of claim 1 that overexpresses one or more components of the non-mevalonate (MEP) pathway.

14. The method of claim 13, further comprising culturing the microbial cell.

15. The method of claim 14, further comprising recovering the terpenoid from the cell culture.

* * * * *